US008575428B2

(12) United States Patent
Kondo et al.

(10) Patent No.: US 8,575,428 B2
(45) Date of Patent: Nov. 5, 2013

(54) METHOD FOR INCREASING THE PRODUCTION OF PLANT BIOMASS AND/OR SEEDS AND METHOD FOR PRODUCING PLANT CAPABLE OF PRODUCING INCREASED AMOUNT OF BIOMASS AND/OR SEEDS

(75) Inventors: Satoshi Kondo, Miyoshi (JP); Chikara Ohto, Toyota (JP); Kenichi Ogawa, Kyoto (JP)

(73) Assignee: Toyota Jidosha Kabushiki Kaisha, Aichi-ken (JP)

( * ) Notice: Subject to any disclaimer, the term of this patent is extended or adjusted under 35 U.S.C. 154(b) by 250 days.

(21) Appl. No.: 12/879,581

(22) Filed: Sep. 10, 2010

(65) Prior Publication Data

US 2011/0065583 A1   Mar. 17, 2011

(30) Foreign Application Priority Data

Sep. 11, 2009   (JP) ................................ 2009-210621

(51) Int. Cl.
*C12N 15/82* (2006.01)

(52) U.S. Cl.
USPC ........................................................ 800/290

(58) Field of Classification Search
None
See application file for complete search history.

(56) References Cited

U.S. PATENT DOCUMENTS

| | | | |
|---|---|---|---|
| 5,872,216 A | 2/1999 | Hannah et al. | |
| 6,166,293 A | 12/2000 | Doerner et al. | |
| 6,559,358 B1 | 5/2003 | Murray | |
| 6,864,405 B1 | 3/2005 | Coruzzi et al. | |
| 2005/0114925 A1 | 5/2005 | Kisaka et al. | |
| 2006/0123505 A1 | 6/2006 | Kikuchi et al. | |
| 2008/0271200 A1 | 10/2008 | Dudits et al. | |
| 2010/0016166 A1* | 1/2010 | Ogawa et al. | 504/320 |
| 2011/0078818 A1* | 3/2011 | Kondo et al. | 800/278 |

FOREIGN PATENT DOCUMENTS

| | | | |
|---|---|---|---|
| JP | 9-503389 A | 4/1997 | |
| JP | 2000-515020 A | 11/2000 | |
| JP | 2001-505410 A | 4/2001 | |
| JP | 2001-519659 A | 10/2001 | |
| JP | 2005-052114 A | 3/2005 | |
| JP | 2005-130770 A | 5/2005 | |
| JP | 2007-530063 A | 11/2007 | |
| WO | 02/10210 A2 | 2/2002 | |
| WO | 2008/082602 A2 | 7/2008 | |

OTHER PUBLICATIONS

Schweighofer et al, Trends in Plant Sci. (2004) 9:236-243.*
Umbarasaite et al., Methods in Mol. Bio. (2011) 779:149-161.*
Meinhard and Grill, FEBS Letters (2001) 508:443-446.*
Office Action issued in related Australian Patent Application No. 2009224235 on Dec. 16, 2011.
E. Koesema et al., "*Arabidopsis* cDNA Clones", Accession No. AAK91405, dated Aug. 20, 2001 (Unpublished), http://www.ncbi.nlm.nih.gov/sviewer/viewer.fcgi?tool=portal&sendto=on&log$-seqv . . . (dated Jan. 20, 2012).
C.J. Kim et al., "*Arabidopsis* ORF Clones", Accession No. AAM10415, dated Apr. 13, 2002 (Unpublished), ncbi.nlm.nih.gov/sviewer/viewer.fcgi?tool=portal&sendto=on&log$-seqv . . . (dated Jan. 20, 2012).
X. Lin et al., "*Arabidopsis thaliana* chromosome III BAC F18C1 Genomic Sequence", Accession No. AAF26133, dated Oct. 30, 2002 (Unpublished), ncbi.nlm.nih.gov/sviewer/viewer.fcgi?tool=portal&sendto=on&log$-seqv . . . (dated Jan. 20, 2012).
Y. Totoki et al., "Large-Scale Analysis of RIKEN *Arabidopsis* Full-length (RAFL) cDNAs", Accession No. BAF00337, dated Jul. 27, 2006 (Unpublished), ncbi.nlm.nih.gov/sviewer/viewer.fcgi?tool=portal&sendto=on&log$-seqv . . . (dated Jan. 20, 2012).
S. Sato et al., "Structural Analysis of *Arabidopsis thaliana* Chromosomes 3. I. Sequence Features of the Regions of 4,504,864 bp Covered by Sixty P1 and TAC Clones", Accession No. BAA95773, dated Feb. 14, 2004, DNA Res, 7(2):131-135, ncbi.nlm.nih.gov/sviewer/viewer.fcgi?tool=portal&sendto=on&log$-seqv . . . (dated Jan. 20, 2012).
Angela Saez et al., "Gain-of-function and loss-of-function phenotypes of the protein phosphatase 2C HAB1 reveal its role as a negative regulator of abscisic acid signalling", The Plant Journal, 2004, 37: 354-369.
David Reyes et al., "Overexpression of a Protein Phosphatase 2C from Beech Seeds in *Arabidopsis* Shows Phenotypes Related to Abscisic Acid Responses and Gibberellin Biosynthesis", Plant Physiology, 2006, 141: 1414-1424.
Mary Paz González-Garcia et al., "Negative Regulation of Abscisic Acid Signaling by the *Fagus sylvatica* FsPP2C1 Plays a Role in Seed Dormancy Regulation and Promotion of Seed Germination", Plant Physiology, 2003, 133: 135-144.

* cited by examiner

*Primary Examiner* — David H Kruse
*Assistant Examiner* — Mykola Kovalenko
(74) *Attorney, Agent, or Firm* — Sughrue Mion, PLLC

(57) ABSTRACT

The present invention provides, inter alia, methods for increasing the production of biomass and/or seeds, and plants for use in such methods. The production of biomass and/or seeds by a plant can be increased by supplying glutathione to a plant into which a gene encoding a protein phosphatase 2C having characteristic consensus sequences has been introduced.

6 Claims, 12 Drawing Sheets

Fig. 1-1

CLUSTAL W (1.83) multiple sequence alignment

```
AT5G26010       MGHCFSLPS------SQSEIHEDNEHGDGNVVCYGEEFGLDQDLPVH---------------
AT4G32950       MGFCFCLSSG----GSTDKSQIYEITDYGQENAVLYSDHHVVPQN------------------
AT1G16220       MGLCHSKIDKTTRKETG-ATSTATT--TVERQS-SGRLRRPRDLYSGG---------------
AT1G79630       MGLCYS-VDRTTGKEPGEASSTATTAETVEERSGSGRWRRPRDLKGGG---------------
At1g03590       --------MHRPCLGMGCCGS--KMGKRGFSDRMVSLHNLVS---------------------
AT3G02750       MGSCLSAE------SRSPRPGSPCSPAFSVRKRKNSKKRPGSRNSSFDYR-------------
AT5G36250       MGSCLSSSGGGGSRRSLHGSPHVPGPGRRKRP-PKRRPGSCSSSFDNT---------------
AT5G01700       MGVCCS---------KGTGIIVEHGADDQNECGDGEAEVRDTNDG------------------
AT3G05640       MGHFSS---MFNGIARSFSIKKAKNINSSKSYAKEATDEMAREAK------------------
AT5G27930       MGHFSS---MFNGLARSFSIKKVKNNNGN-CDAKEAADEMASEAK------------------
AT3G16800       MVLLPA---FLDGLARTVSTKKGKKLSEDEDGGREIAKSMIKDSK------------------
AT2G20050       MGCAYSKTCIGQICATKENSIRQTHQQAPSRGGTRATAAAAAVEEDNPVFNFSSDAVDDV
AT3G06270       MGCVQCKCCS---------RYPSSSSDGDSRGPLEANGVLK---------------------

AT5G26010       -----------------------RLGSVCSIQGTKV--------------------------
AT4G32950       -------------------------LGSVSSLAGGKG-------------------------
AT1G16220       ---------------EISEIQQVVGRLVGNGSSEIACLYTQQGKKG-----------------
AT1G79630       ---------------DIEGIPQVLGRLVSNGSSKIACLYTQQGKKG-----------------
At1g03590       ---------------------IPNRIIGNGKSRSSCIFTQQGRKG-----------------
AT3G02750       ---------------REEPLNQVPGRMFLNGSTEVACIYTQQGKKG-----------------
AT5G36250       ---------------EEPLLHRIPGRMFLNGSTDVSLFSQQGKKG-----------------
AT5G01700       -----------------AVVRTRGSSKHVSMSIKQGKKG-----------------------
AT3G05640       ---------------KKELILRSSGCINADGSNNLASVFSRRGEKG-----------------
AT5G27930       ---------------KKELILKSSGYVNVQGSNNLASLFSKRGEKG-----------------
AT3G16800       ---------------KNSTLLGTSQFVSSESSKRFTSICSNRGEKG-----------------
AT2G20050       DNDEIHQLGLSRDQEWGITRLSRVSSQFLPPDGSRVVKVPSCNYELRCSFLSQRGYYPDA
AT3G06270       --GKDQ---------------KPLGS---IHVPSPNFDMVYSVLSQRGYYPDS

|
AT5G26010       ----LNQDHAVLYQGYGTR-DTELCGVFDGHGKNGHMVSKMVRNRLPSVLLALKEELNQES
AT4G32950       ----LNQDAAILHLGYGTE-EGALCGVFDGHGPRGAFVSKNVRNQLPSILLG----HMNNHS
AT1G16220       ----TNQDAMLVWENFCSRSDTVLCGVFDGHGPFGHMVSKRVRDMLPFTLSTQLKTTSGTE
AT1G79630       ----TNQDAMLVFENFCSRDDTVFCGVFDGHGPFGHMVAKKVRDTLPFTLLTQLKMTSESD
At1g03590       ----INQDAMIVWEDFMSK-DVTFCGVFDGHGPHGHLVARKVRDSLPVKLLSLLNSIK-SK
AT3G02750       ----PNQDAMVVWENFGSRTDTIFCGVFDGHGPYGHMVAKRVRDNLPLKLSAYWEAKVPVE
AT5G36250       ----PNQDAMIVWENFGSMEDTVFCGVFDGHGPYGHIVAKRVRDLLPLKLGSHLESYVSPE
AT5G01700       ----INQDAMTVWENFGGEEDTIFCGVFDGHGPMGHKISRHVCENLPSRVHSKIRSSKSAG
AT3G05640       ----VNQDCAIVWEGYGCQEDMIFCGIFDGHGPWGHFVSKQVRNSMPISLLCNWKETLSQT
AT5G27930       ----VNQDCALVWEGFGCQEDMIFCGIFDGHGPWGHYVAKQVRNSMPLSLLCNWQKILAQA
AT3G16800       ----INQDRAIVWEGFGCQEDITFCGMFDGHGPWGHVIAKRVKKSFPSSLLCQWQQTLASL
AT2G20050       LDKANQDSFAIHTPFGSNSDDHFFGVFDGHGEFGAQCSQFVKRRLCENLLRHGRFRVDPA
AT3G06270       PDKENQDTYCIKTELQGNPNVHFFGVFDGHGVLGTQCSNFVKERVVEMLSEDPTLLEDPE
                    ***  :       :    :*:*****  *   :  *        :       :

AT5G26010       NVCEEEAS---------------------------------------------------K
AT4G32950       -VTRDWKL---------------------------------------------------I
AT1G16220       QSSSKNGLNSAPTCVDEE---------------------QWCELQLCEKDEKLFPEMYLP
AT1G79630       QSSLVGANGFQIKCTEEEEVQTTESEQVQKTESVTTMDEQWCELNPNVNND-ELPEMYLP
At1g03590       QNGPIGTRASKSDSLEAE------------------------KEESTEED------KLNFL
AT3G02750       GVLKAITTDTVNNVTNINNPEDAAAAAFVTAE-----EEPRTSADMEEENTETQPELFQT
AT5G36250       EVLKEISLNTDD---------RKISEDLVHISAN----GESRVYN----KDYVKDQ-DMIQM
AT5G01700       DENIENNSSQSQE----------------------------------------------ELFRE
AT3G05640       TIA------EPDKELQR------------------------------------------FAI
AT5G27930       TLEPELDLEGSNKKISR------------------------------------------FDI
AT3G16800       SSS--------PECSSP------------------------------------------FDL
AT2G20050       -----------------------------------------------------------
AT3G06270       -----------------------------------------------------------
```

```
AT5G26010  WKKRLKYTKVDDITVICLFLQNKEQPS------------------------------------
AT4G32950  WIQKFPTVKIDDISVVCLSLNKKHNPQPQI----------------------------------
AT1G16220  WRLKYPTSKNDDCAVVCLFLEDTSAGGTVEVSETVNHSHEESTESVTITSSKDADKKEEA
AT1G79630  WRIKYPTSKNDDCTVVCLFLQDSSVAMEVSTNVKKDSPKEESIESVTNSTSKEED-----
At1g03590  WKLKYPTSKMDDCAVVCLFLDG-----RMDSETSDNEEQCFSSATNAVESDESQGAEP---
AT3G02750  WRYKYPTSKVDDCAAVCLYLDSSNTNAISTASSISKLEDGEEEELKATTEDDDASG-----
AT5G36250  WRMKFPTSKVDDCAVVCLFLDS--EPNRLSTAS-------------------------
AT5G01700  WRTKFPASKADDCAVVVLYLNHRPYPREGNVS---------------------------
AT3G05640  WNRKRRGIAMDDISAVCLFFHSSSSSPSL-----------------------------
AT5G27930  WKKKRRGYSMDDMSVVCLFLHSSSSS-SLSQHHHAMTILK-------------------
AT3G16800  WRRKRRSIAMDDISVLCLFFRPS----------------------------------
AT2G20050  WLQY---ETRTDDITIIVVHIDGLKDDAPRQLSSTGTQLQPPIPQVVELTGSESPSTFGWN
AT3G06270  WLEH---ENRTDDITIIIVQIKKLSNE------------------------------
             *          **   . : :

AT5G26010  ----------------------------------------------------------------
AT4G32950  ----------------------------------------------------------------
AT1G16220  STETNETVPVWEIKEEKTPESCRIESKKT----TLAECISVK--DDEEWSALEGLTRVNSLLS
AT1G79630  -------EIVP------VKDEKIPESCGIESKMMTMTLAECISVAQDDEEWSALEGLTRVNSLLS
At1g03590  ---CLQRNVTVRSLSTDQENNSYGKVIAEA---DNAEKEKTREGEQNWSGLEGVTRVNSLVQ
AT3G02750  -PSGLGRSSTVRSGKEIALDESETEKLIK------EADNLDSEPGTEYSALEGVARVNTLLN
AT5G36250  -----------FSKEKHINNGVTEPEPD-------TASSSTPDSGTGSPELNGVNRIDTLVN
AT5G01700  ---------------RAISTISWRSNKS----------NNECYGAAPLSPLGLSQRVS-----
AT3G05640  ----------------------------------------------------------------
AT5G27930  ----------------------------------------------------------------
AT3G16800  ----------------------------------------------------------------
AT2G20050  SKNQRVRHDLSRARIRAIENSLENGHAWVPPSPAHRKTWEEEVRVLVCFVFAQPIRNASS
AT3G06270  ----------------------------------------------------------------

AT5G26010  ----------------------
AT4G32950  ----------------------
AT1G16220  IPRFFSGELRSSSWRKWL
AT1G79630  IPRFLSGELRSTSWRKWL
At1g03590  LPRFPGEEPKT-------
AT3G02750  LPRFVPGK----------
AT5G36250  LPVYVPTKE---------
AT5G01700  ------------------
AT3G05640  ------------------
AT5G27930  ------------------
AT3G16800  ------------------
AT2G20050  HSYIRRLNAGFSRAGTH-
AT3G06270  ------------------
```

Fig. 2-1

CLUSTAL W (1.83) multiple sequence alignment

```
AT1G16220    MGLCHSKIDKTTRKETG-ATSTATT----TVERQS-SGRLRRPRDLYSGGEISEIQGVVGRL
AT1G79630    MGLCYS-VDRTTGKEPGEASSTATTAETVEERSGSGRWRRPRDLKGGGDIEGIPQVLGRL
At1g03590    -------MHRPCLGMGCCGS----KMGKRGFSDRMVSLHNLVS---------IPNRI
AT3G02750    MGSCLSAE-------SRSPRPGSPCSPAFSVRKRKNSKKRPGSRNSSFDYRREEPLNQVPGRM
AT5G36250    MGSCLSSSGGGGSRRSLHGSPHVPGPGRRKRP-PKRRPGSCSSSFDNTEEPLLHRIPGRM
AT5G26010    MGHCFSLPS------SGSEIHEDNEHGDG-NVVCYGEEFGLDQDLPVH---------
AT4G32950    MGFCFCLSSGGSTDKSQIYEITDYGQE-NAVLYSDHHVVPQN---------
AT5G01700    MGVCCSKGTG-IIVEHGADDGNECGDGEAEVRDTNDGAVVRTRGSS---------
AT3G05640    MGHFSSMFNGIARSFSIKKAKNINSSKSYAKEATDEMAREAKKKELILR------SSGCI
AT5G27930    MGHFSSMFNGLARSFSIKKVKNMNNGN-CDAKEAADEMASEAKKKELILK------SSGYV
AT3G16800    MVLLPAFLDGLARTVSTKKGKKLSEDEDGGREIAKSMIKDSKKNSTLLG------TSGFV

AT1G16220    VGNGSSEIACLYTQGGKKGTNQDAMLVWENFCSRSDTVLCGVFDGHGPFGHMVSKRVRDM
AT1G79630    VSNGSSKIACLYTQGGKKGTNQDAMLVFENFCSRDDTVFCGVFDGHGPFGHMVAKKVRDT
At1g03590    IGNGKSRSSCIFTQGGRKGINQDAMIVWEDFMCK-DVTFCGVFDGHGPHCHLVARKVRDS
AT3G02750    FLNGSTEVACIYTQGGKKGPNQDAMVVWENFGSRTDTIFCGVFDGHGPYGHMVAKRVRDN
AT5G36250    FLNGSTDTVSLFSQQGKKGPNQDAMIVWENFGSMEDTVFCGVFDGHGPYGHIVAKRVRDL
AT5G26010    -------RLGSVCSIQGTKVLNQDHAVLYQGYG-TRDTELCGVFDGHGKNGHMVSKMVRNR
AT4G32950    -------LGSVSSLAGGKGLNQDAAILHLGYG-TEEGALCGVFDGHGPRGAFVSKNVRNQ
AT5G01700    -------KHVSMSIKGGKKGINQDAMTVWENFGGEEDTIFCGVFDGHGPMGHKISRHVCEN
AT3G05640    NADGSNNLASVFSRRGEKGVNQDCAIVWEGYGCQEDMIFCGIFDGHGPWGHFVSKQVRNS
AT5G27930    NVQGSNNLASLFSKRGEKGVNQDCALVWEGFGCQEDMIFCGIFDGHGPWGHYVAKQVRNS
AT3G16800    SSESSKRFTSICSNRGEKGINQDRAIVWEGFGCQEDITFCGMFDGHGPWGHVIAKRVKKS
                            :  * * ***   : :   :** :*****  *   :  : *

AT1G16220    LPFTLSTQLKTTSGTEQSSSKNGLNSAPTCVDEE-----------QWCEL
AT1G79630    LPFTLLTQLKMTSESDGSSLVGANGFQIKCTEEEEVQTTESEQVQKTESVTTMDEQWCEL
At1g03590    LPVKLLSLLNSIK-SKQNGPIGTRASKSDSLEAE-----------K
AT3G02750    LPLKLSAYWEAKVPVEGVLKAITTDTVNNVTNINNPEDAAAAAAFVTAEEEPRTSADMEE
AT5G36250    LPLKLGSHLESYVSPEEVLKEISLNTDD---------RKISEDLVHISANGESRVYN---K
AT5G26010    LPSVLLALK---------EELNQESNVCE-
AT4G32950    LPSILLG---------HMNNHS-VTR-
AT5G01700    LPSRVHSKIRSSKSAGDENIENNSSQSQE-
AT3G05640    MPISLLCNWK---------ETLSQTTIA-
AT5G27930    MPLSLLCNWQ---------KILAQATLEPE-
AT3G16800    FPSSLLCQWD---------QTLASLSSS-
               :*  :                               ::

AT1G16220    QLCEKDEKLFPEMYLPLKRALLKTCQQMDKELKMHPTINCFCSGTTSVTVIKQGKDLVVG
AT1G79630    NPNVNND-ELPEMYLPLKHAMLKSCQQIDKELKMHPTIDCFCSGTTSVTLIKQGEDLVVG
At1g03590    EESTEED------KLNFLWEEAFLKSFNAMDKELRSHPNLECFCSGCTAVTIIKQGSNLYMG
AT3G02750    ENTETQP------ELFQTLKESFLKAFKVMDRELKFHGSVDCFCSGTTAVTLIKQGQYLVVG
AT5G36250    DYVKDQ------DMIQMLIGSIVKAYRFMDKELKMQVDVDCFCSGTTAVTMVKQGQHLVIG
AT5G26010    --------EEASKWEKACGFTAFRLIDRELNL-QVFNCSFSGSTGVVAITQGDDLVIA
AT4G32950    --------DWKLICETSCLEMDKRILKVK----KIHDCSASGTTAVLAVKHGNQVMVA
AT5G01700    --------ELFREFEDILVTFFKQIDSELGLDSPYDSFCSGTTAVTVFKQADCLVIA
AT3G05640    --------EPDKELQRFAIWKYSFLKTCEAVDLELEHHRKIDSFNSGTTALTIVROGDVIYIA
AT5G27930    -LDLEGSNKKISRFDIWKQSYLKTCATVDQELEHHRKIDSYYSGTTALTIVROGEVIYVA
AT3G16800    --------PECSSPFDLWKQACLKTFSIIDLDLKISPSIDSYCSGCTALTAVLQGDHLVIA
                                              ** *:   :  :  :
```

Fig. 2-2

```
AT1G16220    NIGDSRAVLATRDQDNA-LVAVQLTIDLKPDLP----------------------------
AT1G79630    NIGDSRAVLATRDEDNA-LLAVQLTIDLKPDLP----------------------------
At1g03590    NIGDSRAILGSKDSNDS-MIAVQLTVDLKPDLP----------------------------
AT3G02750    NVGDSRAVMGTRDSENT-LVAVQLTVDLKPNLPGWIILCECMMMLSCGCMMMDPLIMFIGFF
AT5G36250    NIGDSRAVLGVRNKDNK-LVPFQLTEDLKPDVP----------------------------
AT5G26010    NLGDSRAVLGTMTEDGE-IKAVQLTSDLTPDVP----------------------------
AT4G32950    NLGDSRAVMIGTSEDGE-TKVAQLTNDLKPSVP----------------------------
AT5G01700    NLGHSRAVLGTRSKNS---FKAVQLTVDLKPCVQ----------------------------
AT3G05640    NVGDSRAVLATVSDEGS-LVAVQLTVDFKPNLP----------------------------
AT5G27930    NVGDSRAVLAMESDEGS-LVAVQLTLDFKPNLP----------------------------
AT3G16800    NAGDSRAVIATTSDDGNGLVPVQLSVDFKPNIP----------------------------
              * *.***::    ::   **: *:.*  :                    III

AT1G16220    ----------SESARIHRCKGRVFALQDEPEVARVWLPNSDSPGLAMARAFGDFCLKDYGLI
AT1G79630    ----------GESARIQKCKGRVFALQDEPEVARVWLPNSDSPGLAMARAFGDFCLKDYGLI
At1g03590    ----------REAERIKQCKGRVFALQDEPEVSRVWLPFDNAPGLAMARAFGDFCLKDYGVI
AT3G02750    FIPSIELAAEEAERIRKCRGRVFALRDEPEVCRVWLPNCDSPGLAMARAFGDFCLKDFGLI
AT5G36250    ----------AEAERIKRCRGRIFALRDEPGVARLWLPNHNSPGLAMARAFGDFCLKDFGLI
AT5G26010    ----------SEAERIRMCKGRVFAMKTEPSSQRVWLPNQNIPGLAMSRAFGDFRLKDHGVI
AT4G32950    ----------SEAERIRKRNGRVLALESEPHILRVWLPTENRPGLAMSRAFGDFLLKSYGVI
AT5G01700    ----------REAERIVSCKGRVFAMEEEPDVYRVWMPDDDCPGLAMSRAFGDFCLKDYGLV
AT3G05640    ----------QEEERIIGCNGRVFCLQDEPGVHRVWQPVDESPGLAMSRAFGDYCIKDYGLV
AT5G27930    ----------QEKERIIGCKGRVFCLDDEPGVHRVWQPDAETPGLAMSRAFGDYCIKEYGLV
AT3G16800    ----------EEAERIKQSDGRLFCLDDEPGVYRVGMPNGGSLGLAVSRAFGDYCLKDFGLV
                 *  **   **:*.  **   *: *    ***:*****: :*.,*:*

AT1G16220    SVPDINYHRLTERDQYIILATDGVWDVLSNKEAVDIVASAPS-RDTAARAVVDTAVRAWR
AT1G79630    SVPDINYRRLTERDQFIILASDGVWDVLSNKEAVDIVASAPS-RSTAARALVDTAVRSWR
At1g03590    SIPEFSHRVLTDRDQFIVLASDGVWDVLSNEEVVEVVASATS-RASAARLVVDSAVREWK
AT3G02750    SVPDVSFRQLTEKDEFIVLATDGIWDVLSNEDVVAIVASAPS-RSSAARALVESAVRAWR
AT5G36250    SVPDVSYRRLTEKDEFVVLATDGIWDALTNEEVVKIVAKAPT-RSSAGRALVEAAVRNWR
AT5G26010    AVPEISQHRITSKDQFLVLATDGVWDMLSNDEVVSLIWSSGKKQASAAKMVAEAAEAAWK
AT4G32950    ATPQVSTHQITSSDQFLLLASDGVWDVLSNEEVATVVMKSAS-EAGAANEVAEAATNAWI
AT5G01700    CIPDVFCRKVSREDEFVVLATDGIWDVLSNEEVVKVVGSCKD-RSVAAEMLVQRAARTWR
AT3G05640    SVPEVTQRHISIRDQFIILATDGVWDVISNQEAIDIVSSTAE-RAKAAKRLVQQAVRAWN
AT5G27930    SVPEVTQRHISTKDHFIILASDGIWDVISNQEAIEIVSSTAE-RPKAAKRLVEQAVRAWK
AT3G16800    SEPEVTYRKITDKDQFLILATDGMWDVMTNNEAVEIVRGVKE-RRKSAKRLVERAVTLWR
              .*:      :: *:: **:**:** :.*::.  :  :       :.*:.  *   *

AT1G16220    LKYPTSKNDDCAVVCLFLEDTSAGGTVEVSETVNHSHEESTESVTIISSKDADKKEEAST
AT1G79630    IKYPTSKNDDCTVVCLFLQDSSVAMEVSTNVKKDSPKEESIESVTNSTSKEED-------
At1g03590    LKYPTSKMDDCAVVCLFLDG---RMDSETSDNEEQCFSSATNAVESDESQGAEP-------
AT3G02750    YKYPTSKVDDCAAVCLYLDSSNTNAISTASSISKLEDGEEEELKATTEDDDASG-------P
AT5G36250    WKFPTSKVDDCAVVCLFLDS-EPNRLSTAS-----------------------------
AT5G26010    KRLKYTKVDDITVIGLFLQN---------------------------------------
AT4G32950    QKFPTVKIDDISVVCLSLNK---------------------------------------
AT5G01700    TKFPASKADDCAVVVLYLNH---------------------------------------
AT3G05640    RKRRGIAMDDISAVGLFFHSSSSSPSL--------------------------------
AT5G27930    KKRRGYSMDDMSVVCLFLHSSSSS-SLSQHHHAMTILK---------------------
AT3G16800    RKRRSIAMDDISVLGLFFRPS--------------------------------------
               :  **::.::  :
```

Fig. 2-3

```
AT1G16220   ETNETVPVWEIKEEKTPESCRIESKKT--TLAECISVK-DDEEWSALEGLTRVNSLLSIP
AT1G79630   ----EIVP----VKDEKIPESCGIESKMMTMTLAECISVAQDDEEWSALEGLTRVNSLLSIP
At1g03590   CLQRNVTVRSLSTDQENNSYGKVIAEA--DNAEKEKTREGEQNWSGLEGVTRVNSLVQLP
AT3G02750   SGLGRSSTVRSGKEIALDESETEKLIK----EADNLDSEPGTEYSALEGVARVNTLLNLP
AT5G36250   ------------FSKEKHINNGVTEPEPD----TASSSTPDSGTGSPELNGVNRIDTLVNLP
AT5G26010   ------------KEGPS---------------------------------------------
AT4G32950   ------------KHNPQPQI------------------------------------------
AT5G01700   ------------RPYPREGNVSRAIS----------TISWRSNKSNNECYGAAPLSPLQLSQ
AT3G05640   --------------------------------------------------------------
AT5G27930   --------------------------------------------------------------
AT3G16800   --------------------------------------------------------------

AT1G16220   RFFSGELRSSSWRKWL
AT1G79630   RFLSGELRSTSWRKWL
At1g03590   RFPGEEPKT-------
AT3G02750   RFVPGK----------
AT5G36250   VYVPTKE---------
AT5G26010   ----------------
AT4G32950   ----------------
AT5G01700   RVS-------------
AT3G05640   ----------------
AT5G27930   ----------------
AT3G16800   ----------------
```

METHOD FOR INCREASING THE PRODUCTION OF PLANT BIOMASS AND/OR SEEDS AND METHOD FOR PRODUCING PLANT CAPABLE OF PRODUCING INCREASED AMOUNT OF BIOMASS AND/OR SEEDS

BACKGROUND OF THE INVENTION

1. Field of the Invention

The present invention relates to: a method for further increasing the production of biomass and/or seeds by a plant that produces an increased amount of biomass and/or seeds as a result of introduction of a given gene into the plant; and a method for producing such plant capable of producing an increased amount of biomass and/or seeds.

2. Background Art

The term "biomass" generally refers to the total amount of organisms that inhabit or exist in a given area. When such term is used with regard to plants, in particular, it refers to dry weight per unit area. Biomass units are quantified in terms of mass or energy. The expression "biomass" is synonymous with "Seibutsutairyo" or "Seibutsuryo." In the case of plant biomass, the term "standing crop" is occasionally used for "biomass." Since plant biomass is generated by fixing atmospheric carbon dioxide with the use of solar energy, it can be regarded as so-called "carbon-neutral energy." Accordingly, an increase of plant biomass is effective for global environmental preservation, the prevention of global warming, and mitigation of greenhouse gas emissions. Thus, technologies for increasing the production of plant biomass have been industrially significant.

Plants are cultivated for the purpose of using some tissues thereof (e.g., seeds, roots, leaves, or stems) or for the purpose of producing various materials, such as fats and oils. Examples of fats and oils produced from plants that have been heretofore known include soybean oil, sesame oil, olive oil, coconut oil, rice oil, cottonseed oil, sunflower oil, corn oil, safflower oil, palm oil, and rapeseed oil. Such fats and oils are extensively used for household and industrial applications. Also, fats and oils produced from plants are used as raw materials for biodiesel fuel or bioplastic, and the applicability thereof is increasing for alternative energy to petroleum.

In particular, an energy crop such as sugar cane can be used as a raw material for biofuel. Hence, the increased production of the total mass of a plant itself (the amount of plant biomass) is expected. Under such circumstances, improvement in productivity per unit of cultivation area is required in order to increase the production of the amount of plant biomass. It has been found that if the number of cultivated plants is assumed to be constant per unit of cultivation area, improvement in the amount of biomass per plant would be necessary.

However, it is thought that since many genes are involved in the amount of plant biomass (a so-called "kind of quantitative trait"), individual gene introduction or individual genetic modification cannot lead to an effective increase in production. Meanwhile, a great deal of difficulties are associated with introduction of many genes in a desired state into a plant. Such gene introduction is also problematic in that if successful introduction takes place, desirable traits cannot always be acquired.

Various gene introduction techniques are known as techniques for increasing the production of plant biomass, as disclosed in Patent Documents 1-7, for example. However, none of these techniques can be said to exert sufficient effects of increasing the production of biomass.

Patent Documents

Patent Document 1: JP Patent Publication (Kohyo) No. 2001-505410 A
Patent Document 2: JP Patent Publication (Kohyo) No. 2001-519659 A
Patent Document 3: JP Patent Publication (Kohyo) No. 2007-530063 A
Patent Document 4: JP Patent Publication (Kokai) No. 2005-130770 A
Patent Document 5: JP Patent Publication (Kohyo) No. 2000-515020 A
Patent Document 6: JP Patent Publication (Kohyo) No. 9-503389 A
Patent Document 7: JP Patent Publication (Kokai) No. 2005-52114 A

SUMMARY OF THE INVENTION

The present inventors have searched for genes having novel functions of drastically improving the amount of plant biomass and have identified genes capable of drastically increasing the production of plant biomass (PCT/JP2009/054983). The present inventors have further examined plants into which such genes have been introduced. As a result, an object of the present invention is to provide a technique for further increasing the production of biomass and/or seeds.

As a result of intensive studies to achieve the above object, the present inventors have made the novel finding that the production of biomass and/or seeds can be further increased by supplying glutathione to a plant into which a gene encoding a protein phosphatase 2C having characteristic consensus sequences has been introduced. Thus, they have completed the present invention.

Specifically, the method for increasing the production of biomass and/or seeds according to the present invention comprises a step of supplying glutathione to a plant into which a gene encoding protein phosphatase 2C having 3 consensus sequences comprising the amino acid sequences shown in SEQ ID NOS: 1-3 in such order from the N-terminal side has been introduced.

Also, the method for producing a plant according to the present invention comprises a step of supplying glutathione to a plant into which a gene encoding the protein phosphatase 2C having 3 consensus sequences comprising the amino acid sequences shown in SEQ ID NOS: 1-3 in such order from the N-terminal side has been introduced.

In the present invention, the above gene encoding protein phosphatase 2C can be at least one type of gene selected from the group consisting of At1g03590-AtPP2C6-6, At1g16220, At1g79630, At5g01700, At3g02750, At5g36250, At5g26010, At4g32950, At3g16800, At3g05640, At5g27930-AtPP2C6-7, At2g20050, and At3g06270, or a gene functionally equivalent thereto.

In the present invention, the above gene encoding protein phosphatase 2C preferably encodes any one of the following proteins (a) to (c):
(a) a protein comprising the amino acid sequence shown in SEQ ID NO: 5;
(b) a protein comprising an amino acid sequence that has a deletion, a substitution, an addition, or an insertion of one or a plurality of amino acids with respect to the amino acid sequence shown in SEQ ID NO: 5 and has protein phosphatase 2C activity; and
(c) a protein that is encoded by a polynucleotide hybridizing under stringent conditions to a polynucleotide comprising a nucleotide sequence complementary to the nucleotide sequence shown in SEQ ID NO: 4 and has protein phosphatase 2C activity.

Also, in the present invention, an example of the above functionally equivalent gene is a protein phosphatase 2C gene from an organism other than *Arabidopsis thaliana*. Another example of an organism other than *Arabidopsis thaliana* is an organism selected from the group consisting of rice (*Oryza sativa*), Black cottonwood (*Populus trichocarpa*), European grape (*Vitis vinifera*), *Medicago truncatula* (*Medicago truncatula*), alfalfa (*Medicago sativa*), *Physcomitrella patens* (*Physcomitrella patens*), ice plant (*Mesembryanthemum crystallinum*), *Chlamydomonas reinhardtii* (*Chlamydomonas reinhardtii*), corn (*Zea mays*), rapeseed (*Brassica rapa*), tomato (*Solanum lycopersicum*), Monkey flower (*Mimulus guttatus*), and monocellular red alga (*Cyanidioschyzon merolae*).

Examples of plants to be subjected to the present invention include dicotyledons such as plants of the family Brassicaceae. Examples of plants of the family Brassicaceae include *Arabidopsis thaliana* and rapeseed. Other examples of plants to be subjected to the present invention include monocotyledons such as plants of the family Gramineae. Examples of plants of the family Gramineae include rice and sugarcane.

According to the method for increasing the production of biomass and/or seeds according to the present invention, further increased production of biomass and/or seeds becomes possible through very convenient and low cost treatment of a plant that produces an increased amount of biomass and/or seeds as a result of introduction of a given gene into the plant.

Also, according to the method for producing a plant according to the present invention, a plant capable of producing a further increased amount of biomass and/or seeds can be obtained through very convenient and low cost treatment of the plant that produces an increased amount of biomass and/or seeds as a result of introduction of a given gene into the plant.

BRIEF DESCRIPTION OF THE DRAWINGS

FIG. 1-1 is a characteristic diagram showing the results of alignment analysis using a CLUSTAL W (1.83) multiple sequence alignment program for amino acid sequences encoded by At1g03590-AtPP2C6-6, At1g16220, At1g79630, At5g01700, At3g02750, At5g36250, At5g26010, At4g32950, At3g16800, At3g05640, At5g27930-AtPP2C6-7, At2g20050, and At3g06270.

FIG. 1-2 is a characteristic diagram showing the results of alignment analysis using a CLUSTAL W (1.83) multiple sequence alignment program for amino acid sequences encoded by At1g03590-AtPP2C6-6, At1g16220, At1g79630, At5g01700, At3g02750, At5g36250, At5g26010, At4g32950, At3g16800, At3g05640, At5g27930-AtPP2C6-7, At2g20050, and At3g06270.

FIG. 1-3 is a characteristic diagram showing the results of alignment analysis using a CLUSTAL W (1.83) multiple sequence alignment program for amino acid sequences encoded by At1g03590-AtPP2C6-6, At1g16220, At1g79630, At5g01700, At3g02750, At5g36250, At5g26010, At4g32950, At3g16800, At3g05640, At5g27930-AtPP2C6-7, At2g20050, and At3g06270.

FIG. 2-1 is a characteristic diagram showing the results of alignment analysis using a CLUSTAL W (1.83) multiple sequence alignment program for amino acid sequences encoded by At1g03590-AtPP2C6-6, At1g16220, At1g79630, At5g01700, At3g02750, At5g36250, At5g26010, At4g32950, At3g16800, At3g05640, and At5g27930-AtPP2C6-7.

FIG. 2-2 is a characteristic diagram showing the results of alignment analysis using a CLUSTAL W (1.83) multiple sequence alignment program for amino acid sequences encoded by At1g03590-AtPP2C6-6, At1g16220, At1g79630, At5g01700, At3g02750, At5g36250, At5g26010, At4g32950, At3g16800, At3g05640, and At5g27930-AtPP2C6-7.

FIG. 2-3 is a characteristic diagram showing the results of alignment analysis using a CLUSTAL W (1.83) multiple sequence alignment program for amino acid sequences encoded by At1g03590-AtPP2C6-6, At1g16220, At1g79630, At5g01700, At3g02750, At5g36250, At5g26010, At4g32950, At3g16800, At3g05640, and At5g27930-AtPP2C6-7.

FIG. 3 is a photo showing the above ground parts of wild-type plants and transformed plants into which a fragment containing ORF of the PP2C (protein phosphatase 2C) gene (At3g05640) was introduced.

DESCRIPTION OF THE PREFERRED EMBODIMENTS

Figure 3:
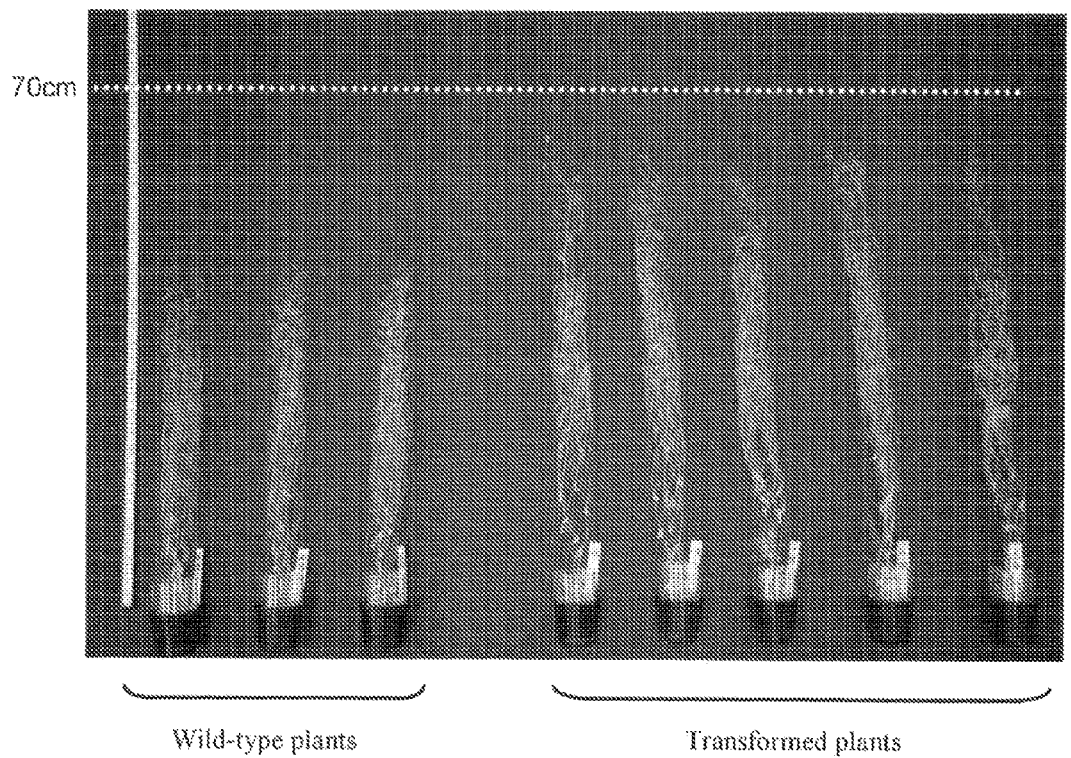

The present invention will be described in detail as follows.

The method according to the present invention comprises supplying glutathione to a plant into which a given gene has been introduced. Here, the term "supplying glutathione" refers to growing a plant in the presence of glutathione during at least one of the periods of all growth stages following sowing. Examples of a method for supplying glutathione include a method that involves spraying a glutathione solution over the surface of soil in which plant seeds are sowed and a method that involves mixing soil with a carrier (e.g., bentonite, clay, talc, or vermiculite) containing glutathione.

As glutathione to be used herein, either reduced glutathione or oxidized glutathione, or both thereof, may be used. In view of the effects of increasing the production of biomass and/or seeds, oxidized glutathione is preferably used. The above-defined amount of glutathione to be supplied may be supplied in a single supply or in divided supplies.

A plant to which the method according to the present invention is applied is produced by introducing a gene encoding protein phosphatase 2C having characteristic consensus sequences. The thus produced plants produce a significantly improved (increased) amount of biomass compared with wild-type plants. Such plant may be produced by introducing the protein phosphatase 2C gene for expression into all plant tissues or introducing the same for expression into at least some of the plant tissues. Here, the term "plant tissue(s)" refers to plant organ(s) such as leaves, stems, seeds, roots, and flowers. The term "introducing a gene" is used herein in reference to a situation in which the expression level of a target gene is determined to significantly increase compared with the expression level in a wild-type organism. Therefore, the term "introducing a gene" as used herein refers to both a form whereby a target gene is introduced from the outside and a form whereby the expression level is improved by altering an expression control region of an endogenous gene.

Protein Phosphatase 2C Gene

The protein phosphatase 2C gene to be introduced into a plant encodes protein phosphatase 2C that has 3 consensus sequences comprising the amino acid sequences shown in SEQ ID NOS: 1-3 in such order from the N-terminal side. In addition, a gene group classified as Group E as in FIG. 1 of Topographic cladogram (on page 237 of Reference: TRENDS in Plant Science Vol. 9 No. 5 May 2004 pages 236-243) encodes protein phosphatase 2C having 3 consensus sequences comprising the amino acid sequences shown in SEQ ID NOS: 1-3 in such order from the N-terminal side. In addition, the reference predicts the presence of 76 protein phosphatase 2C genes in *Arabidopsis thaliana* and discloses the results of producing a phylogenetic tree of these genes using T-Coffee software (reference; Notredame, C. et al. 2000 T-Coffee: a novel method for fast and accurate multiple sequence alignment. J. Mol. Biol. 302, 205-247) as in FIG. 1. In this phylogenetic tree, protein phosphatase 2C genes classified as members of Group E encode protein phosphatase 2C that has 3 consensus sequences comprising the amino acid sequences shown in SEQ ID NOS: 1-3 in such order from the N-terminal side. The 3 consensus sequences comprising the amino acid sequences shown in SEQ ID NOS: 1-3 are characteristic sequences in Group E in the above-mentioned classification and serve as a basis for clear differentiation from other groups.

Group E in the above classification includes protein phosphatase 2C genes specified by *Arabidopsis thaliana*-derived At1g03590-AtPP2C6-6, At1g16220, At1g79630, At5g01700, At3g02750, At5g36250, At5g26010, At4g32950, At3g16800, At3g05640, At5g27930-AtPP2C6-7, At2g20050, and At3g06270. FIG. 1 shows the results of alignment analysis using a CLUSTAL W (1.83) multiple sequence alignment program (which can be used with the DDBJ of the National Institute of Genetics (http://clustalw.ddbj.nig.ac.jp/top-j.html)) for the amino acid sequences encoded by these *Arabidopsis thaliana*-derived protein phosphatase 2C genes, At1g03590-AtPP2C6-6, At1g16220, At1g79630, At5g01700, At3g02750, At5g36250, At5g26010, At4g32950, At3g16800, At3g05640, At5g27930-AtPP2C6-7, At2g20050, and At3g06270 (with the amino acid (sequence) substitution matrix used herein being a default matrix known as BLOSUM (Blocks of Amino Acid Substitution Matrix)). As shown in FIG. 1, these protein phosphatase 2C genes classified as members of Group E have consensus sequences characteristic in the regions denoted as I to III. These regions denoted as I to III are subjected with a rice-derived protein phosphatase 2C gene (described later) to alignment analysis, so that the 3 consensus sequences comprising the amino acid sequences shown in SEQ ID NOS: 1-3 can be defined.

Herein, in the amino acid sequence shown in SEQ ID NO: 1, which is an amino acid residue denoted as "Xaa," may be any amino acid, and it is not limited to any particular amino acid. However, the 1$^{st}$ amino acid residue from the N-terminal side in the amino acid sequence shown in SEQ ID NO: 1 is preferably leucine (three character code: Leu and single character code: L; the same applies to the following) or phenylalanine (Phe, F). The 4$^{th}$ amino acid residue from the N-terminal side in the amino acid sequence shown in SEQ ID NO: 1 is preferably valine (Val, V), isoleucine (Ile, I), or methionine (Met, M). The 16$^{th}$ amino acid residue from the N-terminal side in the amino acid sequence shown in SEQ ID NO: 1 is preferably serine (Ser, S) or alanine (Ala, A). The 17$^{th}$ amino acid residue from the N-terminal side in the amino acid sequence shown in SEQ ID NO: 1 is preferably lysine (Lys, K), arginine (Arg, R), glutamine (Gln, Q), or asparagine (Asn, N). That is, a consensus sequence comprising the amino acid sequence shown in SEQ ID NO: 1 is preferably (L/F)XG(V/I/M)FDGHGXXGXXX(S/A)(K/R/Q/N)XV. In such amino acid sequence, pluralities of amino acids in parentheses represent possible variations of amino acid residues at the relevant positions. Also, in the amino acid sequences, "X" means that any amino acid residue may be present at the relevant position.

Also, such a consensus sequence may be a sequence containing the following 3 amino acid residues on the N-terminal side of Region I in FIG. 1: (D/E/N)XX.

Here, in the amino acid sequence shown in SEQ ID NO: 2, an amino acid residue denoted as "Xaa," may be any amino acid, and it is not limited to any particular amino acid. However, the 5$^{th}$ amino acid residue from the N-terminal side in the amino acid sequence shown in SEQ ID NO: 2 is preferably glycine (Gly, G), alanine (Ala, A), or serine (Ser, S). The 6$^{th}$ amino acid residue from the N-terminal side in the amino acid sequence shown in SEQ ID NO: 2 is preferably valine (Val, V), leucine (Leu, L), or isoleucine (Ile, I). The 9$^{th}$ amino acid residue from the N-terminal side in the amino acid sequence shown in SEQ ID NO: 2 is preferably isoleucine (Ile, I), valine (Val, V), phenylalanine (Phe, F), methionine (Met, M), or leucine (Leu, L). The 12$^{th}$ amino acid residue from the N-terminal side in the amino acid sequence shown in SEQ ID NO: 2 is preferably glycine (Gly, G) or alanine (Ala, A). The 15$^{th}$ amino acid residue from the N-terminal side in the amino acid sequence shown in SEQ ID NO: 2 is preferably leucine (Leu, L), valine (Val, V), or isoleucine (Ile, I). The 17$^{th}$ amino acid residue from the N-terminal side in the amino acid sequence shown in SEQ ID NO: 2 is preferably isoleucine (Ile, I), valine (Val, V), or methionine (Met, M). The 18$^{th}$ amino acid residue from the N-terminal side in the amino acid sequence shown in SEQ ID NO: 2 is preferably glycine (Gly, G) or alanine (Ala, A). The 22$^{nd}$ amino acid residue from the N-terminal side in the amino acid sequence shown in SEQ ID NO: 2 is preferably aspartic acid (Asp, D) or histidine (His, H). The 26$^{th}$ amino acid residue from the N-terminal side in the amino acid sequence shown in SEQ ID NO: 2 is preferably valine (Val, V) or isoleucine (Ile, I). The 27th amino acid residue from the N-terminal side in the amino acid sequence shown in SEQ ID NO: 2 is preferably leucine (Leu, L), methionine (Met, M), or isoleucine (Ile, I). That is, a consensus sequence comprising the amino acid sequence shown in SEQ ID NO: 2 is preferably SGXT(G/A/S)(V/L/I)XX(I/V/F/M/L)XX(G/A)XX(L/V/I)X(I/V/M)(A/G) NXG(D/H)SRA(V/I)(L/M/I). In such amino acid sequence, pluralities of amino acids in parentheses represent possible variations of amino acid residues at the relevant positions. Also, in the amino acid sequences, "X" means that any amino acid residue may be present at the relevant position.

Here, the amino acid sequence shown in SEQ ID NO: 3, an amino acid residue denoted as "Xaa," may be any amino acid, and it is not limited to any particular amino acid. However, the 4th amino acid residue from the N-terminal side in the amino acid sequence shown in SEQ ID NO: 3 is preferably methionine (Met, M), valine (Val, V), or phenylalanine (Phe, F). The 5th amino acid residue from the N-terminal side in the amino acid sequence shown in SEQ ID NO: 3 is preferably serine (Ser, S), alanine (Ala, A), or threonine (Thr, T). The 7th amino acid residue from the N-terminal side in the amino acid sequence shown in SEQ ID NO: 3 is preferably alanine (Ala, A) or serine (Ser, S). The 8th amino acid residue from the N-terminal side in the amino acid sequence shown in SEQ ID NO: 3 is preferably phenylalanine (Phe, F), isoleucine (Ile, I), or valine (Val, V). The 14th amino acid residue from the N-terminal side in the amino acid sequence shown in SEQ ID NO: 3 is preferably lysine (Lys, K) or glutamic acid (Glu, E). The 18th amino acid residue from the N-terminal side in the amino acid sequence shown in SEQ ID NO: 3 is preferably valine (Val, V) or leucine (Leu, L). The 19th amino acid residue from the N-terminal side in the amino acid sequence shown in SEQ ID NO: 3 is preferably isoleucine (Ile, I) or valine (Val, V). The 23rd amino acid residue from the N-terminal side in the amino acid sequence shown in SEQ ID NO: 3 is preferably glutamic acid (Glu, E), glutamine (Gln, Q), or aspartic acid (Asp, D). The 24th amino acid residue from the N-terminal side in the amino acid sequence shown in SEQ ID NO: 3 is preferably isoleucine (Ile, I), valine (Val, V), or phenylalanine (Phe, F). The 29th amino acid residue from the N-terminal side in the amino acid sequence shown in SEQ ID NO: 3 is preferably isoleucine (Ile, I), leucine (Leu, L), or valine (Val, V). The 30th amino acid residue from the N-terminal side in the amino acid sequence shown in SEQ ID NO: 3 is preferably serine (Ser, S), threonine (Thr, T), or asparagine (Asn, N). The 33rd amino acid residue from the N-terminal side in the amino acid sequence shown in SEQ ID NO: 3 is preferably aspartic acid (Asp, D), asparagine (Asn, N), or histidine (His, H). The 35th amino acid residue from the N-terminal side in the amino acid sequence shown in SEQ ID NO: 3 is preferably phenylalanine (Phe, F) or tyrosine (Tyr, Y). The 36th amino acid residue from the N-terminal side in the amino acid sequence shown in SEQ ID NO: 3 is preferably leucine (Leu, L), isoleucine (Ile, I), valine (Val, V), phenylalanine (Phe, F), or methionine (Met, M). The 37th amino acid residue from the N-terminal side in the amino acid sequence shown in SEQ ID NO: 3 is preferably valine (Val, V), leucine (Leu, L), or isoleucine (Ile, I). The 38th amino acid residue from the N-terminal side in the amino acid sequence shown in SEQ ID NO: 3 is preferably leucine (Leu, L) or valine (Val, V). The 40th amino acid residue from the N-terminal side in the amino acid sequence shown in SEQ ID NO: 3 is preferably threonine (Thr, T) or serine (Ser, S). The 43rd amino acid residue from the N-terminal side in the amino acid sequence shown in SEQ ID NO: 3 is preferably valine (Val, V), isoleucine (Ile, I), or methionine (Met, M). The 44th amino acid residue from the N-terminal side in the amino acid sequence shown in SEQ ID NO: 3 is preferably tryptophan (Trp, W) or phenylalanine (Phe, F). The 45th amino acid residue from the N-terminal side in the amino acid sequence shown in SEQ ID NO: 3 is preferably aspartic acid (Asp, D) or glutamic acid (Glu, E). The 47th amino acid residue from the N-terminal side in the amino acid sequence shown in SEQ ID NO: 3 is preferably leucine (Leu, L), isoleucine (Ile, I), or methionine (Met, M). The 48th amino acid residue from the N-terminal side in the amino acid sequence shown in SEQ ID NO: 3 is preferably serine (Ser, S), threonine (Thr, T), or proline (Pro, P). The 49th amino acid residue from the N-terminal side in the amino acid sequence shown in SEQ ID NO: 3 is preferably asparagine (Asn, N) or serine (Ser, S). The 52nd amino acid residue from the N-terminal side in the amino acid sequence shown in SEQ ID NO: 3 is preferably valine (Val, V) or alanine (Ala, A). The 55th amino acid residue from the N-terminal side in the amino acid sequence shown in SEQ ID NO: 3 is preferably leucine (Leu, L), valine (Val, V), isoleucine (Ile, I), or methionine (Met, M). The 56th amino acid residue from the N-terminal side in the amino acid sequence shown in SEQ ID NO: 3 is preferably isoleucine (Ile, I) or valine (Val, V). That is, a consensus sequence comprising the amino acid sequence shown in SEQ ID NO: 3 is more specifically GXA(M/V/F)(S/A/T)R(A/S)(F/I/V)GDXXX(K/E)XXG(V/L)(I/V)XXP(E/Q/D) (I/V/F)XXXX(I/L/V)(T/S)XX(D/N/H)X(F/Y)(L/I/V/F)(V/L/I)(L/V)A(T/S)DG(V/I/M)(W/F)(D/E)X(L/I/M)(S/T/P)(N/S)XX(V/A)XX(L/V/I/M)(I/V). In such amino acid sequence, pluralities of amino acids in parentheses represent possible variations of amino acid residues at the relevant positions. Also, in the amino acid sequences, "X" means that any amino acid residue may be present at the relevant position.

Here, the 20th amino acid residue from the N-terminal side in the amino acid sequence shown in SEQ ID NO: 3 is more preferably alanine (Ala, A), serine (Ser, S), or cysteine (Cys, C). Also, the 50th amino acid residue from the N-terminal side in the amino acid sequence shown in SEQ ID NO: 3 is more preferably aspartic acid (Asp, D), glutamic acid (Glu, E), lysine (Lys, K), glutamine (Gln, Q), or asparagine (Asn, N).

Variations of amino acid residues that can be present at given positions are determined based on the following reasons. As described in Reference (1) ("McKee Biochemistry," 3rd ed., Chapter 5 Amino Acid•Peptide•Protein 5.1 Amino Acid; editorial supervisor: Atsushi Ichikawa; translation supervisor: Shinichi Fukuoka; publisher: Ryosuke Sone; publishing office: Kagaku-Dojin Publishing Company, INC, ISBN4-7598-0944-9), it is well known that amino acids are classified based on side chains having similar properties (e.g., chemical properties and physical sizes). Also, it is well known that molecular evolutionary substitution frequently takes place among amino acid residues classified in a given group, while retaining protein activity. Based on these concepts, a substitution (mutation) score matrix for amino acid residues (BLOSUM: Blocks of Amino Acid Substitution Matrix) is proposed in FIG. 2 of Reference (2): Henikoff S., Henikoff J. G., Amino-acid substitution matrices from protein blocks, Proc. Natl. Acad. Sci. U.S.A., 89, 10915-10919 (1992) and is broadly used. Reference (2) is based on a finding that amino acid substitutions that take place among amino acids with side chains having similar chemical properties result in less structural or functional changes in the entire protein. According to References (1) and (2) above, amino acid side chain groups to be used in multiple alignment can be considered based on indices such as chemical properties and physical sizes. They are shown as amino acid groups with a score of 0 or higher and preferably as amino acid groups with a score of 1 or higher through the use of the score matrix (BLOSUM) disclosed in Reference (2). Typical groups are the following 8 groups. Further precisely grouped amino acid groups may be amino acid groups with a score of 0 or higher, preferably a score of 1 or higher, and further preferably a score of 2 or higher.

1) Aliphatic Hydrophobic Amino Acid Group (ILMV Group)

This group is a group of amino acids having aliphatic hydrophobic side chains, among neutral nonpolar amino acids disclosed in Reference (1) above, which is composed of V (Val, valine), L (Leu, leucine), I (Ile, isoleucine), and M (Met, methionine). Among amino acids classified as neutral nonpolar amino acids according to Reference (1), FGACWP is not included in this "aliphatic hydrophobic amino acid group" because of the following reasons: G (Gly, glycine) and A (Ala, alanine) are the same size as that of or smaller in size than a methyl group and have weak non polar effects; C (Cys, cysteine) may play an important role in S—S bonds and has a property of forming a hydrogen bond with an oxygen atom or a nitrogen atom; F (Phe, phenylalanine) and W (Trp, tryptophan) have side chains with significantly large molecular weights and have strong aromatic effects; P (Pro, proline) has strong imino acid effects, so as to fix the angle of the main chain of the polypeptide.

2) Group having Hydroxymethylene Group (ST Group)

This group is a group of amino acids (from among neutral polar amino acids) having hydroxymethylene groups in side chains, which is composed of S (Ser, serine) and T (Thr, threonine). Hydroxy groups existing in the side chains of S and T constitute sugar-binding sites, so that these sites are often important for a polypeptide (protein) to have specific activity.

3) Acidic Amino Acid (DE Group)

This group is a group of amino acids having acidic carboxyl groups in side chains, which is composed of D (Asp, aspartic acid) and E (Glu, glutamic acid).

4) Basic Amino Acid (KR Group)

This group is a group of basic amino acids, which is composed of K (Lys, lysine) and R (Arg, arginine). These K and R are positively charged within a wide pH range and have basic properties. On the other hand, H (His, histidine) classified in basic amino acids is almost never ionized at pH 7, so that H is not classified in this group.

5) Methylene Group=Polar Group (DHN Group)

This group is characterized in that: in all cases, a methylene group as a side chain binds to an α-carbon element beyond which a polar group is present; and the physical sizes of methylene groups (nonpolar groups) closely resemble from each other. This group is composed of N (Asn, asparagine; polar group is an amide group), D (Asp, aspartic acid; polar groups are carboxyl groups), and H (His, histidine; polar groups are imidazole groups).

6) Dimethylene Group=Polar Group (EKQR Group)

This group is characterized in that: in all cases, linear hydrocarbon having a length longer than that of a dimethylene group binds as a side chain to an α-carbon element, beyond which a polar group is present; and the physical sizes of dimethylene groups that are nonpolar groups closely resemble from each other. This group is composed of E (Glu, glutamic acid, polar group is a carboxyl group), K (Lys, lysine; polar groups are amino groups), Q (Gln, glutamine; polar groups are amide groups), and R (Arg, arginine; polar groups are imino groups and amino groups).

7) Aromatic Series (FYW Group)

This group is a group of aromatic amino acids having benzene nuclei in the side chains and characterized by having chemical properties unique in aromatic series. This group is composed of F (Phe, phenylalanine), Y (Tyr, tyrosine), and W (Trp, tryptophan).

8) Ring & Polar (HY Group)

This group is a group of amino acids having both ring structures in the side chains and polarity, which is composed of H (H, histidine; Both ring structures and polar groups are imidazole groups), and Y (Tyr, tyrosine; Ring structures are benzene nuclei and polar groups are hydroxy groups).

As described above, it is understood that: in the given amino acid sequences shown in SEQ ID NOS: 1-3, an amino acid residue denoted as Xaa may be any amino acid; or amino acid residues denoted as Xaa may be substituted with each other within the above groups 1)-8). Hence, in the present invention, the protein phosphatase 2C gene to be introduced into a plant may be a protein phosphatase 2C gene from any plant, as long as it has the 3 consensus sequences comprising the amino acid sequences shown in SEQ ID NOS: 1-3 in such order from the N-terminal side.

More specifically, examples of an *Arabidopsis thaliana* protein phosphatase 2C-coding gene having the 3 consensus sequences (comprising the amino acid sequences shown in SEQ ID NOS: 1-3) in such order from the N-terminal side include At1g03590-AtPP2C6-6, At1g16220, At1g79630, At5g01700, At3g02750, At5g36250, At5g26010, At4g32950, At3g16800, At3g05640, At5g27930-AtPP2C6-7, At2g20050, and At3g06270. In the present invention, at least one type of gene selected from the gene group is introduced. Particularly in the present invention, it is preferable to introduce at least one type of gene selected from among At1g03590-AtPP2C6-6, At1g16220, At1g79630, At5g01700, At3g02750, At5g36250, At5g26010, At4g32950, At3g16800, At3g05640, and At5g27930-AtPP2C6-7. Particularly, in the present invention, it is more preferable to introduce at least one type of gene selected from among At3g16800, At3g05640, and At5g27930-AtPP2C6-7 and it is most preferable to introduce a gene specified by At3g05640.

In addition, FIG. 2 shows the results of alignment analysis using a CLUSTAL W (1.83) multiple sequence alignment program (that can be used with the DDBJ of the National Institute of Genetics (http://clustalw.ddbj.nig.ac.jp/top-j.html)) for amino acid sequences encoded by At1g03590-AtPP2C6-6, At1g16220, At1g79630, At5g01700, At3g02750, At5g36250, At5g26010, At4g32950, At3g16800, At3g05640, and At5g27930-AtPP2C6-7 (amino acid (sequence) substitution matrix used herein is default matrix, BLOSUM (Blocks of Amino Acid Substitution Matrix)).

That is, FIG. 2 shows the 3 consensus sequences in protein phosphatase 2C encoded by At1g03590-AtPP2C6-6, At1g16220, At1g79630, At5g01700, At3g02750, At5g36250, At5g26010, At4g32950, At3g16800, At3g05640, and At5g27930-AtPP2C6-7. Regions denoted as I-III in FIG. 2 are subjected with an ortholog of a rice-derived protein phosphatase 2C gene (described later) to alignment analysis, so that the 3 consensus sequences comprising the amino acid sequences shown in SEQ ID NOS: 1-3 above can be defined as the 3 consensus sequences comprising the amino acid sequences shown in SEQ ID NOS: 31, 32, and 33, respectively.

The consensus sequence shown in SEQ ID NO: 31 is more specifically (L/F)CG(V/I/M)FDGHGXXGXX(V/I)(S/A)(K/R)XV. The consensus sequence shown in SEQ ID NO: 32 is more specifically SGXT(G/A/S)(V/L)XX(I/V/F/L)XX(G/A)XX(L/V/I)X(I/V/M)(A/G)NX G(D/H)SRA(V/I)(L/M/I). The consensus sequence shown in SEQ ID NO: 33 is more specifically GLA(M/V)(S/A)R(A/S)(F/L)GDXX(L/I/V)KX(Y/F/H)G(V/L)(I/V)XXP(E/Q/D)(I/V/F)XXXX(I/L/V)(T/S)XXDX(F/Y)(L/I/V/M)(V/L/I)LA(T/S) DG(V/I/M)WDX(L/I/M/V)(S/T)NX(E/D)(V/A)XX(L/V/I)(I/V).

In addition, in such amino acid sequences, pluralities of amino acids in parentheses represent possible variations of amino acid residues at the relevant positions. Also, in these amino acid sequences, "X" means that any amino acid residue may be present at the relevant position.

Here, the 9$^{th}$ amino acid residue from the N-terminal side in the amino acid sequence shown in SEQ ID NO: 32 is more preferably isoleucine (Ile, I), valine (Val, V), or phenylalanine (Phe, F). Also, the 11$^{th}$ amino acid residue from the N-terminal side in the amino acid sequence shown in SEQ ID NO: 32 is more preferably glutamine (Gln, Q) or histidine (His, H). Moreover, the 13$^{th}$ amino acid residue from the N-terminal side in the amino acid sequence shown in SEQ ID NO: 32 is more preferably lysine (Lys, K), glutamic acid (Glu, E), serine (Ser, S), glutamine (Gln, Q), aspartic acid (Asp, D), or asparagine (Asn, N).

Here, the 7$^{th}$ amino acid residue from the N-terminal side in the amino acid sequence shown in SEQ ID NO: 33 is more preferably alanine (Ala, A). Also, the 8$^{th}$ amino acid residue from the N-terminal side in the amino acid sequence shown in SEQ ID NO: 33 is more preferably phenylalanine (Phe, F). Moreover, the 11$^{th}$ amino acid residue from the N-terminal side in the amino acid sequence shown in SEQ ID NO: 33 is more preferably phenylalanine (Phe, F) or tyrosine (Tyr, Y). Furthermore, the 13$^{th}$ amino acid residue from the N-terminal side in the amino acid sequence shown in SEQ ID NO: 33 is more preferably leucine (Leu, L) or isoleucine (Ile, I). Moreover, the 15$^{th}$ amino acid residue from the N-terminal side in the amino acid sequence shown in SEQ ID NO: 33 is more preferably aspartic acid (Asp, D), serine (Ser, S), or glutamic acid (Glu, E). Furthermore, the 20$^{th}$ amino acid residue from the N-terminal side in the amino acid sequence shown in SEQ ID NO: 33 is more preferably serine (Ser, S), alanine (Ala, A), or cysteine (Cys, C). Moreover, the 27$^{th}$ amino acid residue from the N-terminal side in the amino acid sequence shown in SEQ ID NO: 33 is more preferably histidine (His, H) or arginine (Arg, R). Furthermore, the 34$^{th}$ amino acid residue from the N-terminal side in the amino acid sequence shown in SEQ ID NO: 33 is more preferably glutamine (Gln, Q), glutamic acid (Glu, E), or histidine (His, H). Furthermore, the 36$^{th}$ amino acid residue from the N-terminal side in the amino acid sequence shown in SEQ ID NO: 33 is more preferably leucine (Leu, L), isoleucine (Ile, I), or valine (Val, V). Furthermore, the 47$^{th}$ amino acid residue from the N-terminal side in the amino acid sequence shown in SEQ ID NO: 33 is more preferably leucine (Leu, L), isoleucine (Ile, I), or valine (Val, V). Furthermore, the 50$^{th}$ amino acid residue from the N-terminal side in the amino acid sequence shown in SEQ ID NO: 33 is more preferably lysine (Lys, K), glutamic acid (Glu, E), glutamine (Gln, Q), aspartic acid (Asp, D), or asparagine (Asn, N).

As examples, the nucleotide sequence of the coding region in the gene specified by At3g05640 is shown in SEQ ID NO: 4 and the amino acid sequence of protein phosphatase 2C encoded by the gene specified by At3g05640 is shown in SEQ ID NO: 5. Also, the nucleotide sequence of the coding region in the gene specified by At5g27930 is shown in SEQ ID NO: 34 and the amino acid sequence of protein phosphatase 2C encoded by the gene specified by At5g27930 is shown in SEQ ID NO: 35. Moreover, the nucleotide sequence of the coding region in the gene specified by At3g02750 is shown in SEQ ID NO: 36 and the amino acid sequence of protein phosphatase 2C encoded by the gene specified by At3g02750 is shown in SEQ ID NO: 37. Furthermore, the nucleotide sequence of the coding region in the gene specified by At3g16800 is shown in SEQ ID NO: 38 and the amino acid sequence of protein phosphatase 2C encoded by the gene specified by At3g16800 is shown in SEQ ID NO: 39.

Also, in the present invention, genes functionally equivalent to genes listed above may also be introduced. Here, the term "functionally equivalent gene" refers to, for example, a gene (from an organism other than *Arabidopsis thaliana*) that: has the 3 consensus sequences (preferably, the 3 consensus sequences comprising the amino acid sequences shown in SEQ ID NOS: 31-33. The same applies to the following) comprising the amino acid sequences shown in SEQ ID NOS: 1-3 in such order from the N-terminal side; and encodes protein phosphatase 2C. Also, the term "functionally equivalent gene" refers to a gene that encodes a protein having protein phosphatase 2C activity. The term "protein phosphatase 2C activity" refers to $Mg^{2+}$- or $Mn^{2+}$-dependent serine/threonine phosphatase (Ser/Thr phosphatase) activity. Therefore, whether or not a gene encodes a protein having protein phosphatase 2C activity can be confirmed by examining whether or not the gene product has serine/threonine phosphatase activity in the presence of $Mg^{2+}$ or $Mn^{2+}$. Conventionally known techniques can be appropriately employed for determining serine/threonine phosphatase activity. For example, a commercially available activity determination kit ProFluor (registered trademark) Ser/Thr Phosphatase Assay (Promega) can be used.

Here, example of organisms is not limited to *Arabidopsis thaliana*. For example, rice (*Oryza sativa*) is included. Specifically, an example of a functionally equivalent gene is a rice Os05g0358500 gene. The nucleotide sequence of a coding region of the Os05g0358500 gene is shown in SEQ ID NO: 6 and the amino acid sequence of the protein encoded by the gene is shown in SEQ ID NO: 7. Also, examples of the above-mentioned rice-derived functionally equivalent gene include Os11g0109000 (the nucleotide sequence and the amino acid sequence are shown in SEQ ID NOS: 8 and 9, respectively), Os12g0108600 (the nucleotide sequence and the amino acid sequence are shown in SEQ ID NOS: 10 and 11, respectively), Os02g0471500 (the nucleotide sequence and the amino acid sequence are shown in SEQ ID NOS: 12 and 13, respectively), Os04g0321800 (the nucleotide sequence and the amino acid sequence are shown in SEQ ID NOS: 14 and 15, respectively), Os11g0417400 (the nucleotide sequence and the amino acid sequence are shown in SEQ ID NOS: 16 and 17, respectively), Os07g0566200 (the nucleotide sequence and the amino acid sequence are shown in SEQ ID NOS: 18 and 19, respectively), Os08g0500300 (the nucleotide sequence and the amino acid sequence are shown in SEQ ID NOS: 20 and 21, respectively), Os02g0224100 (the nucleotide sequence and the amino acid sequence are shown in SEQ ID NOS: 22 and 23, respectively), and Os02g0281000 (the nucleotide sequence and the amino acid sequence are shown in SEQ ID NOS: 40 and 41, respectively).

Moreover, examples of the above-mentioned functionally equivalent genes from plants other than *Arabidopsis thaliana* and rice include genes (UniProt data base Accession Nos. A9P973, A9PFSO, and A9P7U4) from Black cottonwood (*Populus trichocarpa*), genes (UniProt data base Accession Nos. A7PRZ8, A7Q8H4, A7PV59, A5C3B0, A5BF43, A7QFG6, A7P4H7, A5C0C9, A5AP53, A7QQF9, and A5BDP5) from European grape (*Vitis vinifera*), genes (UniProt data base Accession Nos. Q2HW33 and Q4L0F8) from *Medicago truncatula* (*Medicago truncatula*), a gene (GenBank data base Accession No. AY651248) from alfalfa (*Medicago sativa*), genes (UniProt data base Accession Nos. A9SE70, A9SE69, and A9RFU1) from *Physcomitrella patens* (*Physcomitrella patens*), a gene (UniProt data base Accession No. 2511453C) from ice plant (*Mesembryanthemum crystallinum*), a gene (UniProt data base Accession No. A8HQG8) from *Chlamydomonas reinhardtii* (*Chlamydomonas reinhardtii*), genes (GenBank data base Accession Nos. BT024031, BT017414, and BT024134) from corn (*Zea mays*), genes (GenBank data base Accession Nos. AC189312 and AC189579) from rapeseed (*Brassica rapa*), genes (GenBank data base Accession Nos. AP009550, AP009302, and AP009278) from tomato (*Solanum lycopersicum*), a gene (GenBank data base Accession No. AC182571) from monkey flower (*Mimulus guttatus*), and a gene (GenBank data base Accession No. AP006489) from monocellular red alga (*Cyanidioschyzon merolae*).

In these plants other than *Arabidopsis thaliana*, which are represented by the above examples, a gene encoding protein phosphatase 2C that has the 3 consensus sequences comprising the amino acid sequences shown in SEQ ID NOS: 1-3 in such order from the N-terminal side can be easily searched for and/or identified from a known database such as GenBank based on the above-listed nucleotide sequence of *Arabidopsis thaliana*-derived protein phosphatase 2C gene or amino acid sequence of protein phosphatase 2C.

In addition, a protein phosphatase 2C gene to be introduced in the present invention is not limited to the above described protein phosphatase 2C genes comprising the nucleotide sequences and the amino acid sequences shown in SEQ ID NOS: 4-23 and 34-39. Hence, the protein phosphatase 2C gene may be a gene that contains an amino acid sequence having a deletion, a substitution, an addition, or an insertion of one or a plurality of amino acids with respect to the amino acid sequences shown in odd numbers of SEQ ID NOS: 4-23 and 34-39, and, having protein phosphatase 2C activity. Here the term "a plurality of amino acids" refers to 1 to 20, preferably 1 to 10, more preferably 1 to 7, further preferably 1 to 5, and particularly preferably 1 to 3 amino acids, for example. In addition, amino acid deletion, substitution, or addition can be performed by altering a nucleotide sequence encoding the above protein phosphatase 2C gene by a technique known in the art. Mutation can be introduced into a nucleotide sequence by a known technique such as the Kunkel method or the Gapped duplex method or a method based thereof. For example, mutation is introduced with a mutagenesis kit using site-directed mutagenesis (e.g., Mutant-K or Mutant-G (both are trade names of TAKARA Bio)) or the like, or a LA PCR in vitro Mutagenesis series kit (trade name, TAKARA Bio). Also, a mutagenesis method may be: a method using a chemical mutation agent represented by EMS (ethyl methanesulfonate), 5-bromouracil, 2-aminopurine, hydroxylamine, N-methyl-N'-nitro-N nitrosoguanidine, or other carcinogenic compounds; or a method that involves radiation treatment or ultraviolet [UV] treatment typically using X-rays, alpha rays, beta rays, gamma rays, an ion beam, or the like.

Also, protein phosphatase 2C genes to be introduced herein may be genes homologous to the protein phosphatase 2C genes comprising the nucleotide sequences and the amino acid sequences shown in SEQ ID NOS: 4-23. Here, the term "homologous gene" generally refers to a gene that has evolutionarily branched off from a common ancestor gene, including a homologous gene (ortholog) of 2 types of species and a homologous gene (paralog) generated by overlapping branching that takes place within the same species. In other words, the above term "functionally equivalent gene" refers to a homologous gene such as an ortholog or a paralog. Furthermore, the above term "functionally equivalent gene" may also refer to a gene that does not evolve from a common gene, but simply has analogous functions.

Examples of genes analogous to the protein phosphatase 2C genes comprising the nucleotide sequences and the amino acid sequences shown in SEQ ID NOS: 4-23 and 34-39 include genes encoding proteins having: amino acid sequences that have 70% or more, preferably 80% or more, more preferably 90% or more, and most preferably 95% or more similarity to these amino acid sequences; the 3 consensus sequences comprising the amino acid sequences shown in SEQ ID NOS: 1-3 in such order from the N-terminal side; and protein phosphatase 2C activity. Here, the value of similarity refers to a value that can be found based on default setting using a computer mounted with a BLAST (Basic Local Alignment Search Tool) program and a database containing gene sequence information.

Also, genes analogous to protein phosphatase 2C genes comprising the nucleotide sequences and the amino acid sequences shown in SEQ ID NOS: 4-23 and 34-39 can be identified by, when the plant genome information remains unclarified, extracting the genome from a target plant or constructing a cDNA library for a target plant and then isolating a genomic region or cDNA hybridizing under stringent conditions to at least a portion of the protein phosphatase 2C genes comprising the nucleotide sequences shown in even numbers of SEQ ID NOS: 4-23 and 34-39. Here, the term "stringent conditions" refers to conditions under which namely a specific hybrid is formed, but a non-specific hybrid is never formed. For example, such conditions comprise hybridization at 45° C. with 6×SSC (sodium chloride/sodium citrate), followed by washing at 50° C. to 65° C. with 0.2-1× SSC and 0.1% SDS. Alternatively, such conditions comprise hybridization at 65° C. to 70° C. with 1×SSC, followed by washing at 65° C. to 70° C. with 0.3×SSC. Hybridization can be performed by a conventionally known method such as a method described in J. Sambrook et al. Molecular Cloning, A Laboratory Manual, 2nd Ed., Cold Spring Harbor Laboratory (1989).

When the present invention is applied to a plant, the plant will have a significantly improved amount of biomass and/or seeds compared with wild-type plants, as a result of introduction of a protein phosphatase 2C gene having the above described 3 consensus sequences that comprise the amino acid sequences shown in SEQ ID NOS: 1-3 from the N-terminal side in such order. Examples of a technique for introduction of such protein phosphatase 2C gene include a technique for modifying a promoter of an endogenous protein phosphatase 2C gene in a target plant, a technique for introducing an expression vector in which an exogenous protein phosphatase 2C gene is arranged under control of a promoter that enables constitutive expression, and a technique by which the two above techniques are performed simultaneously.

A preferred example is a technique for introducing an expression vector in which the above protein phosphatase 2C gene is arranged under control of a promoter that enables constitutive expression into a target plant.

Expression Vector

An expression vector is constructed to contain a promoter that enables expression within a plant and the above described protein phosphatase 2C gene. As a vector serving as a mother body for an expression vector, various conventionally known vectors can be used. For example, plasmids, phages, cosmids, or the like can be used and such vector can be appropriately selected depending on plant cells into which it is introduced and introduction methods. Specific examples of such vector include pBR322, pBR325, pUC19, pUC119, pBluescript, pBluescriptSK, and pBI vectors. Particularly, when a method for introduction of a vector into a plant uses *Agrobacterium*, a pBI binary vector is preferably used. Specific examples of such pBI binary vector include pBIG, pBIN19, pBI101, pBI121, and pBI221.

A promoter to be used herein is not particularly limited, as long as it enables expression of a protein phosphatase 2C gene within a plant. Any known promoter can be appropriately used. Examples of such promoter include a cauliflower mosaic virus 35S promoter (CaMV35S), various actin gene promoters, various ubiquitin gene promoters, a nopaline synthase gene promoter, a tobacco PR1a gene promoter, a tomato ribulose 1,5-bisphosphate carboxylase•oxidase small subunit gene promoter, a napin gene promoter, and an oleosin gene promoter. Of these, a cauliflower mosaic virus 35S promoter, an actin gene promoter, or a ubiquitin gene promoter can be more preferably used. The use of each of the above promoters enables strong expression of any gene when it is introduced into plant cells.

Also, a promoter having functions of causing site-specific expression in a plant can also be used herein. As such promoter, any conventionally known promoter can be used. When the above described protein phosphatase 2C gene is site-specifically introduced using such promoter, a plant organ in which the gene is introduced can be more increased than wild-type plant organs.

In addition, an expression vector may further contain other DNA segments in addition to a promoter and the above protein phosphatase 2C gene. Such other DNA segments are not particularly limited and examples thereof include a terminator, a selection marker, an enhancer, and a nucleotide sequence for enhancing translation efficiency. Also, the above recombinant expression vector may further have a T-DNA region. A T-DNA region can enhance efficiency for gene introduction particularly when the above recombinant expression vector is introduced into a plant using *Agrobacterium*.

A transcription terminator is not particularly limited, as long as it has functions as a transcription termination site and may be any known transcription terminator. For example, specifically, a transcription termination region (Nos terminator) of a nopaline synthase gene, a transcription termination region (CaMV35S terminator) of cauliflower mosaic virus 35S, or the like can be preferably used. Of them, the Nos terminator can be more preferably used. In the case of the above recombinant vector, a phenomenon such that an unnecessarily long transcript is synthesized and that a strong promoter decreases the number of copies of a plasmid after introduction into plant cells can be prevented by arranging a transcription terminator at an appropriate position.

As a transformant selection marker, a drug resistance gene can be used, for example. Specific examples of such drug resistance gene include drug resistance genes against hygromycin, bleomycin, kanamycin, gentamicin, chloramphenicol, and the like. Transformed plants can be easily selected by selecting plants that can grow in medium containing the above antibiotics.

An example of a nucleotide sequence for increasing translation efficiency is an omega sequence from tobacco mosaic virus. This omega sequence is arranged in an untranslated region (5'UTR) of a promoter, so that the translation efficiency of the fusion gene can be increased. As such, the recombinant expression vector may contain various DNA segments depending on purposes.

A method for constructing a recombinant expression vector is not particularly limited. To an appropriately selected vector serving as a mother body, the above promoter and the above protein phosphatase 2C gene, and if necessary, the above other DNA segments may be introduced in an predetermined order. For example, the above protein phosphatase 2C gene and a promoter (and, if necessary, a transcription terminator or the like) are linked to construct an expression cassette and then the cassette may be introduced into a vector. In construction of an expression cassette, for example, cleavage sites of DNA segments are prepared to have protruding ends complementary to each other and then performing a reaction with a ligation enzyme, making it possible to specify the order of the DNA segments. In addition, when an expression cassette contains a terminator, DNA segments may be arranged in the following order from upstream: a promoter, the above protein phosphatase 2C gene, and a terminator. Also, reagents for construction of an expression vector (that is, types of restriction enzymes, ligation enzymes, and the like) are also not particularly limited. Hence, commercially available reagents can be appropriately selected and used.

Also, a method for replicating (a method for producing) the above expression vector is not particularly limited and conventionally known replication methods can be used herein. In general, such expression vector may be replicated within *Escherichia coli* as a host. At this time, preferred types of *Escherichia coli* may be selected depending on the types of vector.

Transformation

The above-described expression vector is introduced into a target plant by a general transformation method. A method for introducing an expression vector into plant cells (transformation method) is not particularly limited. Conventionally known appropriate introduction methods can be used depending on plant cells. Specifically, a method using *Agrobacterium* or a method that involves direct introduction into plant cells can be used, for example. As a method using *Agrobacterium*, a method described in Bechtold, E., Ellis, J. and Pelletier, G. (1993) In Planta *Agrobacterium*-mediated gene transfer by infiltration of adult *Arabidopsis* plants. C.R. Acad. Sci. Paris Sci. Vie, 316, 1194-1199, or a method described in Zyprian E, Kado C1, *Agrobacterium*-mediated plant transformation by novel mini-T vectors in conjunction with a high-copy vir region helper plasmid. Plant Molecular Biology, 1990, 15(2), 245-256. can be employed, for example.

As a method for directly introducing an expression vector into plant cells, microinjection, electroporation, a polyethylene glycol method, a particle gun method, protoplast fusion, a calcium phosphate method, or the like can be employed.

Also, when a method for directly introducing DNA into plant cells is employed, DNA that can be used herein contains transcriptional units required for the expression of a target gene, such as a promoter and a transcription terminator, and a target gene. Vector functions are not essential in such case. Moreover, a DNA that contains a protein coding region alone of a target gene having no transcriptional unit may be used herein, as long as it is integrated into a host's transcriptional unit and then the target gene can be expressed.

Examples of plant cells into which the above expression vector or an expression cassette containing no expression vector, but a target gene is introduced include cells of each tissue of plant organs such as flowers, leaves, and roots, calluses, and suspension-cultured cells. At this time, an appropriate expression vector may be constructed according to the types of plant to be produced or a versatile expression vector may be constructed in advance and then introduced into plant cells.

Plants into which an expression vector is introduced or in other words, plants required to increase the production of biomass are not particularly limited. Specifically, through introduction of the above-described protein phosphatase 2C gene, effects of increasing the production of biomass can be expected for all plants. Examples of target plants include, but are not limited to, dicotyledons and monocotyledons, such as plants (see below) belonging to the families Brassicaceae, Gramineae, Solanaceae, Leguminosae, Salicaceae, and the like.

Family Brassicaceae: *Arabidopsis thaliana* (*Arabidopsis thaliana*), rapeseed (*Brassica rapa, Brassica napus, Brassica campestris*), cabbage (*Brassica oleracea* var. *capitata*), napa (*Brassica rapa* var. *pekinensis*), ging-geng-cai (*Brassica rapa* var. *chinensis*), turnip (*Brassica rapa* var. *rapa*), turnip greens (*Brassica rapa* var. *hakabura*), potherb mustard (*Brassica rapa* var. *lancinifolia*), Komatsuna (*Brassica rapa* var. *peruviridis*), pak choi (*Brassica rapa* var. *chinensis*), daikon (*Raphanus sativus*), Japanese horseradish (*Wasabia japonica*), and the like.

Family Solanaceae: tobacco (*Nicotiana tabacum*), eggplant (*Solanum melongena*), potato (*Solaneum tuberosum*), tomato (*Lycopersicon lycopersicum*), chile pepper (*Capsicum annuum*), petunia, and the like.

Family Leguminosae: soy (*Glycine max*), pea (*Pisum sativum*), broad bean (*Vicia faba*), Wisteria (*Wisteria floribunda*), peanuts (*Arachis hypogaea*), bird's foot trefoil (*Lotus corniculatus* var. *japonicus*), common bean (*Phaseolus vulgaris*), azuki bean (*Vigna angularis*), Acacia, and the like.

Family Asteraceae: florists' daisy (*Chrysanthemum morifolium*), sunflower (*Helianthus annuus*), and the like.

Family Arecaceae: oil palm (*Elaeis guineensis, Elaeis oleifera*), coconut (*Cocos nucifera*), date palm (*Phoenix dactylifera*), copernicia, and the like.

Family Anacardiaceae: wax tree (*Rhus succedanea*), cashew nut (*Anacardium occidentale*), lacquer tree (*Toxicodendron vernicifluum*), mango (*Mangifera indica*), pistachio (*Pistacia vera*), and the like.

Family Cucurbitaceae: pumpkin (*Cucurbita maxima, Cucurbita moschata, Cucurbita pepo*), cucumber (*Cucumis sativus*), snake gourd (*Trichosanthes cucumeroides*), gourd (*Lagenaria siceraria* var. *gourda*), and the like.

Family Rosaceae: almond (*Amygdalus communis*), rose (*Rosa*), strawberry (*Fragaria*), cherry (*Prunus*), apple (*Malus pumila* var. *domestica*), and the like.

Family Caryophyllaceae: carnation (*Dianthus caryophyllus*) and the like.

Family Salicaceae: poplar (*Populus trichocarpa, Populus nigra*, or *Populus tremula*) and the like.

Family Gramineae: corn (*Zea mays*), rice (*Oryza sativa*), barley (*Hordeum vulgare*), wheat (*Triticum aestivum*), bamboo (*Phyllostachys*), sugarcane (*Saccharum officinarum*), napier grass (*Pennisetum pupureum*), erianthus (*Erianthus ravenae*), miscanthus (Japanese silver grass) (*Miscanthus virgatum*), sorghum (*Sorghum*) and switch grass (*Panicum*), and the like.

Family Liliaceae: tulip (*Tulipa*), lily (*Lilium*), and the like.

Of these examples, energy crops such as sugarcane, corn, rapeseed, and sunflower, which can serve as raw materials for biofuel, may be preferable targets. This is because the costs for biofuel such as bioethanol, biodiesel, biomethanol, bioDME, bioGTL (BTL), and biobutanol can be reduced by increasing the production of biomass using energy crops.

Also, as described above, protein phosphatase 2C genes that can be used in the present invention can be isolated from various plants and used. Such protein phosphatase 2C genes can be appropriately selected and used, depending on the types of target plant required to increase the biomass production. Specifically, when a plant required to increase the biomass production is a monocotyledon, a protein phosphatase 2C gene that is isolated from a monocotyledon is preferably introduced. In particular, when a plant required to increase the biomass production is rice, the rice-derived protein phosphatase 2C gene (SEQ ID NO: 6) is preferably introduced.

In addition, in the present invention, even when a plant required to increase the biomass production is a monocotyledon, a dicotyledon-derived protein phosphatase 2C gene may be introduced. Specifically, for example, the *Arabidopsis thaliana*-derived protein phosphatase 2C gene (SEQ ID NO: 4) may be introduced into not only dicotyledons, but also a variety of plants that are classified as monocotyledons.

Other Steps and Methods

After the above transformation, a step of selecting proper transformants from plants can be performed by a conventionally known method. Such selection method is not particularly limited. For example, selection can be made based on drug resistance such as hygromycin resistance. Alternatively, after the growth of transformants, plants are directly weighed or the any organs or tissues thereof are weighed, the weights are compared with those of wild-type plants, and then plants with significantly increased weights thereof may be selected.

Also, progeny plants can be obtained from transformed plants obtained by transformation according to a conventional method. Progeny plants retaining a trait such that the expression level of the above protein phosphatase 2C gene is significantly improved compared with wild-type plants are selected based on the amount of biomass. Therefore, a stable plant line capable of producing an increased amount of biomass because of having the above trait can be produced. Also, plant cells or reproductive materials, such as seeds, fruits, stocks, calluses, tubers, cut ears, or lumps, may be obtained from a transformed plant or an offspring plant thereof. A stable plant line capable of producing an increased amount of biomass because of having the above trait can be mass-produced therefrom based on such materials.

As explained above, according to the present invention, the production of the biomass and/or seeds of plants (already capable of exerting significantly increased production of biomass and/or seeds per plant) can be further increased compared with wild-type plants through introduction of the above described protein phosphatase 2C gene. Specifically, when glutathione is supplied to a plant into which the above protein phosphatase 2C gene has been introduced, the production of biomass and/or seeds per plant is significantly increased, compared with a case in which no glutathione has been supplied to the plant. Here, the term "significantly increased production of biomass" refers to a situation in which the total weight of each plant is statistically significantly increased when glutathione is supplied to the plant into which the above protein phosphatase 2C gene has been introduced. In this case, even when some plant tissues become specifically large and the sizes of the other tissues are equivalent to those of plants to which no glutathione has been supplied, it is concluded that the amount of biomass is increased if the total weight of the entire plant is large. Also, the term "significantly increased production of seeds" refers to a situation in which the total amount and/or total number of seeds harvested from a plant is statistically significantly high compared with plants to which no glutathione has been supplied. That is, the term "significantly increased production of seeds" may refer to any of: a case in which the size of each seed is improved; a case where the size per seed is equivalent but the number of seeds is improved; or a case in which the size per seed is improved and the number of seeds is also improved.

According to the present invention, the production of biomass and/or seeds by plants is increased. Hence, improvement in productivity can be achieved in both of the following cases: a case in which a purpose is to produce the whole plant; and a case in which a purpose is to produce some plant tissues (e.g., seeds) or components contained in plants. For example, when a purpose is to produce fats and oils contained in plant seeds, the amounts of fats and oils that can be harvested per area under cultivation can be greatly improved. Here, examples of fats and oils include, but are not particularly limited to, plant-derived fats and oils such as soybean oil, sesame oil, olive oil, coconut oil, rice oil, cottonseed oil, sunflower oil, corn oil, safflower oil, and rapeseed oil. Also, the thus produced fats and oils can be broadly used for household uses or industrial uses and can be further used as raw materials for biodiesel fuel. Hence, according to the present invention, the above fats and oils for household uses or industrial uses, biodiesel fuel, and the like can be produced at low cost by supplying glutathione to plants expressing the above protein phosphatase 2C gene.

EXAMPLES

The present invention will be specifically described in the following reference examples and examples. However, the examples are not intended to limit the technical scope of the present invention.

Reference Example 1

Preparation of Transformants (*Arabidopsis thaliana*) Through Introduction of the PP2C (Protein Phosphatase 2C) gene (At3g05640)
1. Materials and Methods
1-1. Experimental Materials
As experimental materials, seeds of *Arabidopsis thaliana* mutants (Activation-tag T-DNA lines: Weigel T-DNS lines, Total of 20072 lines) were used. In addition, the seeds were purchased from the Nottingham *Arabidopsis* Stock Centre (NASC). Regarding the seeds used as experimental materials, Weigel, D. et al., 2000, Plant Physiol. 122, 1003-1013 can be referred to.
1-2. Methods
1-2-1. Selection of Salt-Resistant Mutants
Seeds of Weigel T-DNA lines were aseptically sowed on 125 mM or 150 mM NaCl-containing modified MS agar (1%) medium [vitamins in B5 medium, 10 g/l sucrose, and 8 g/L agar (for bacterial medium; Wako Pure Chemical Industries, Ltd.)] and then cultured at 22° C. under 30-100 µmol/m²/sec illumination (a cycle of 16 hours in the light/8 hours in the dark). Two to 4 weeks after sowing, salt-resistant mutant candidates were selected. In addition, regarding MS medium, see Murashige, T. et al., 1962, Physiol. Plant. 15, 473-497. Also, regarding the B5 medium, see Gamborg, O. L. et al., 1968, Experimental Cell Research 50, 151-158.
1-2-2. DNA Preparation
A site for insertion of T-DNA into the genome of the thus selected salt-resistant *Arabidopsis thaliana* line was determined by a TAIL-PCR method. First, young leaves were harvested from the cultivated *Arabidopsis thaliana* plants and then crushed under liquid nitrogen freezing. DNA was prepared using a DNA preparation kit (DNeasy Plant Mini Kit, QIAGEN) according to the standard protocols included with the kit.
1-2-3. TAIL-PCR Method and Presumption of T-DNA Insertion Site
Three (3) types of specific primer, TL1, TL2, and TL3, were determined to be located near the left T-DNA sequence (T-DNA left border) of an activation-tagging vector (pSKI015: GenBank accession No. AF187951) used in Weigel T-DNA lines. With the use of an arbitrary primer P1 and the following PCR reaction solutions and reaction conditions, TAIL-PCR (supervisors, Isao Shimamoto and Takuji Sasaki, New Edition, Plant PCR Experimental Protocols, 2000, pp. 83-89, Shujunsha, Tokyo, Japan; Liu, Y. G. and Whttier, R. F., 1995, Genomics 25, 674-681; Liu, Y. G. et al., Plant J., 8, 457-463, 1995) was performed, so that genomic DNA adjacent to T-DNA was amplified.

The specific sequences of the primers TL1, TL2, TL3, and P1 are as follows.

(SEQ ID NO: 24)
TL1:    5'-TGC TTT CGC CAT TAA ATA GCG ACG G-3'

(SEQ ID NO: 25)
TL2:    5'-CGC TGC GGA CAT CTA CAT TTT TG-3'

(SEQ ID NO: 26)
TL3:    5'-TCC CGG ACA TGA AGC CAT TTA C-3'

(SEQ ID NO: 27)
P1:     5'-NGT CGA SWG ANA WGA A-3'

In addition, in SEQ ID NO: 25, "n" represents "a," "g," "c," or "t" (location: 1 and 11), "s" represents "g" or "c" (location: 7), and "w" represents "a" or "t" (location: 8 and 13).

The 1$^{st}$ PCR reaction solution composition and reaction conditions are shown in Table 1 and Table 2, respectively.

TABLE 1

| Template (genomic DNA) | 10 ng |
|---|---|
| 10 × PCR buffer (Takara Bio) | 2 µl |
| 2.5 mM dNTPs (Takara Bio) | 1.6 µl |
| 1$^{st}$ specific primer (TL1: SEQ ID NO: 24) | 0.5 pmol |
| Arbitrary primer 1 (SEQ ID NO: 27) | 100 pmol |
| TaKaRa Ex Taq (Takara Bio) | 1.0 unit |
| Total | 20 µl |

TABLE 2

| #1: | 94° C. (30 seconds)/95° C. (30 seconds) |
|---|---|
| #2: | 5 cycles of 94° C. (30 seconds)/65° C. (30 seconds)/72° C. (1 minute) |
| #3: | 1 cycle of 94° C. (30 seconds)/25° C. (1 minute)→raised to 72° C. within 3 minutes/72° C. (3 minutes) |
| #4: | 94° C. (15 seconds)/65° C. (30 seconds)/72° C. (1 minute), 94° C. (15 seconds)/68° C. (30 seconds)/72° C. (1 minute), and 15 cycles of 94° C. (15 seconds)/44° C. (30 seconds)/72° C. (1 minute) |
| #5: | 72° C. (3 minutes) |

The 2$^{nd}$ PCR reaction solution composition and reaction conditions are shown in Table 3 and Table 4, respectively.

TABLE 3

| Template (50-fold dilution of the 1$^{st}$ PCR product) | 1 µl |
|---|---|
| 10 × PCR buffer (Takara Bio) | 2 µl |
| 2.5 mM dNTPs (Takara Bio) | 1.5 µl |
| 2$^{nd}$ specific primer (TL2: SEQ ID NO: 25) | 5 pmol |
| Arbitrary primer 1 (SEQ ID NO: 27) | 100 pmol |
| TaKaRa Ex Taq (Takara Bio) | 0.8 unit |
| Total | 20 µl |

TABLE 4

| | |
|---|---|
| #6: | 94° C. (15 seconds)/64° C. (30 seconds)/72° C. (1 minute), 94° C. (15 seconds)/64° C. (30 seconds)/72° C. (1 minute), and 12 cycles of 94° C. (15 seconds)/44° C. (30 seconds)/72° C. (1 minute) |
| #5: | 72° C. (5 minutes) |

The 3$^{rd}$ PCR reaction solution composition and reaction conditions are shown in Table 5 and Table 6, respectively.

TABLE 5

| | |
|---|---|
| Template (50-fold dilution of the 2$^{nd}$ PCR product) | 1 μl |
| 10 × PCR buffer (Takara Bio) | 5 μl |
| 2.5 mM dNTPs (Takara Bio) | 0.5 μl |
| 3$^{rd}$ specific primer (TL3: SEQ ID NO: 26) | 10 pmol |
| Arbitrary primer 1 (SEQ ID NO: 27) | 100 pmol |
| TaKaRa Ex Taq (Takara Bio) | 1.5 unit |
| Total | 50 μl |

TABLE 6

| | |
|---|---|
| #7: | 20 cycles of 94° C. (30 seconds)/44° C. (30 seconds)/72° C. (1 minute) |
| #5: | 72° C. (3 minutes) |

Subsequently, the 2$^{nd}$ and the 3$^{rd}$ reaction products were subjected to agarose gel electrophoresis and then the presence or the absence of amplification and the specificity of reaction products were confirmed. Also, the 3$^{rd}$ amplification products were subjected to a sequencing reaction directly using a Big-Dye Terminator Cycle Sequencing Kit Ver. 3. 1 (Applied Biosystems) and the specific primer TL3. Thus, a nucleotide sequence was determined using an ABI PRISM 3100 Genetic Analyzer (Applied Biosystems). As a result, 498-bp sequence information was obtained (SEQ ID NO: 28).

The *Arabidopsis* Information Resource (TAIR: http://www.arabidopsis.org/) was subjected to a BLAST search for the thus obtained sequence. Thus, the insertion site was found to be the gene of [AGI (*Arabidopsis* Genome Initiative gene code) code: At3g05630] of *Arabidopsis thaliana* chromosome 3.

1-2-4. Prediction of Activated Genes

Activated genes were predicted from the sequence of a presumed open reading frame (ORF) gene existing within a 10-Kb range near the T-DNA insertion site (At3g05630) revealed in 1-2-3.

1-2-5. Obtainment of Predicted Genes

For amplification of a fragment containing the ORF region of PP2C (protein phosphatase 2C) gene (At3g05640) predicted to be activated in 1-2-4, PCR primers 5640PF1 and 5640PR1 were designed and synthesized based on the sequence information disclosed at the TAIR (http://www.arabidopsis.org/home.html). In addition, these primers were designed, so that a restriction enzyme site (BsrG I or Sal I) required for introduction into expression vectors was added to the terminus of each primer.

```
5640PF1 (SEQ ID NO: 29):
5'-ACG CGT CGA CAT GGG ACA TTT CTC TTC CAT GTT
CAA CGG-3'

5640PR1 (SEQ ID NO: 30):
5'-TGT ACA TGT ACA CTA TAG AGA TGG CGA CGA CGA
TGA AGA ATG G-3'
```

According to the method described in 1-2-2, a template DNA was prepared from wild-type *Arabidopsis thaliana* (eco-type Col-0). Phusion High-Fidelity DNA Polymerase (New England BioLabs: NEB) was used as an enzyme and the above 5640PF1 and 5640PR1 were used as primers. The relevant PCR reaction solution composition and reaction conditions are shown in Table 7 and Table 8, respectively.

TABLE 7

| | |
|---|---|
| Template (genomic DNA) | 60 ng |
| 10 × HF buffer (NEB) | 5 μl |
| 10 mM dNTPs (NEB) | 1.0 μl |
| Each primer | 20 pmol |
| Phusion High-Fidelity DNA Polymerase | 1.0 unit |
| Total | 50 μl |

TABLE 8

| | |
|---|---|
| #1: | 98° C. (30 seconds) |
| #2: | 15 cycles of 98° C. (10 seconds)/55° C. (30 seconds)/72° C. (30 seconds) |
| #5: | 72° C. (10 minutes) |

PCR amplification products were subjected to electrophoresis with 2% agarose gel (TAE buffer) and then fragments were stained with ethidium bromide. A gel containing target fragments was excised using a scalpel. Target DNA fragments were eluted and purified using GFX PCR DNA and a GEL Band Purification Kit (Amersham). Adenin was added to the thus obtained DNA fragment using an A-Addition Kit (QIAGEN). The amplified DNA to which adenine had been added was ligated to a TA-Cloning pCR2.1 vector using a TOPO TA Cloning Kit (Invitrogen) and then transformed into competent cells (*E. coli* TOP 10) included with the kit. After transformation, cells were cultured in LB medium supplemented with 50 μl/ml kanamycin and then transformants were selected. Colonies that had appeared were subjected to liquid culture in LB medium supplemented with 50 μl/ml kanamycin. Plasmid DNA was prepared from the thus obtained microorganisms using a Plasmid Mini Kit (QIAGEN). The thus obtained fragment containing ORF of the PP2C (protein phosphatase 2C) gene (At3g05640) was cloned into a vector, followed by determination of the nucleotide sequence and sequence analysis.

1-2-6. Construction of Plant Expression Vector

A fragment containing ORF of the PP2C (protein phosphatase 2C) gene (At3g05640) was inserted into a plant expression vector pBI121 containing an omega sequence from tobacco mosaic virus. Thus, a construct was prepared.

First, the pCR2.1 vector, in which a fragment containing ORF of the PP2C (protein phosphatase 2C) gene (At3g05640) had been cloned in 1-2-5, was treated with restriction enzymes Sal I and BsrG I.

Next, similarly pBI121 containing an omega sequence was treated with restriction enzymes Sal I and BsrG I. The products digested with these restriction enzymes were subjected to 0.8% agarose gel electrophoresis. A fragment of about 1600 bp containing ORF of the PP2C (protein phosphatase 2C) gene (At3g05640) and pBI121 containing the omega sequence were each fractioned and purified from the gel using GFX PCR DNA and a GEL Band Purification Kit (Amersham).

For introduction of a fragment containing ORF of the PP2C (protein phosphatase 2C) gene (At3g05640) using a pBI121 fragment containing the omega sequence as a vector, the vector and the insert were mixed at a ratio of 1:10, followed by an overnight ligation reaction at 16° C. using an equivalent amount of a TaKaRa Ligation kit ver. 2 (Takara Bio Inc.).

The total amount of the reaction solution was added to 100 µl of competent cells (*E. coli* strain DH5α, TOYOBO), so that transformation was performed according to protocols included with the kit. Cells were applied to LB agar medium containing 50 µg/ml kanamycin and then cultured overnight. Colonies that had appeared were subjected to liquid culture in LB medium supplemented with 50 µg/ml kanamycin. Plasmid DNA was prepared from the thus obtained microorganisms using a Plasmid Mini Kit (QIAGEN).

The thus obtained fragment containing ORF of the PP2C (protein phosphatase 2C) gene (At3g05640) was subcloned into an expression vector, followed by determination of the nucleotide sequence and sequence analysis.

1-2-7. Gene Introduction into *Arabidopsis thaliana* Using *Agrobacterium* Method The plant expression vector constructed in 1-2-6 was introduced into *Agrobacterium tumefaciens* C58C1 strain by electroporation (Plant Molecular Biology Mannal, Second Edition, B. G. Stanton and A. S. Robbert, Kluwer Acdemic Publishers 1994). Subsequently, *Agrobacterium tumefaciens* in which the plant expression vector had been introduced was introduced into wild-type *Arabidopsis thaliana* (eco-type Col-0) by an infiltration method described by Clough et al. (Steven J. Clough and Andrew F. Bent, 1998, The Plant Journal 16, 735-743).

Transformants were selected using kanamycin-containing medium. T1 generation plants were produced by self-pollination from the transformants, so that T2 seeds were obtained.

1-2-8. Confirmation of the Phenotype of Transformant

T2 seeds produced in 1-2-7 were aseptically sowed and then the resulting plants were transplanted into pots (each with a diameter of 50 mm) containing vermiculite mixed soil. As control plants for comparison, *Arabidopsis thaliana* plants that had not undergone recombination were transplanted. They were cultivated under conditions of 22° C. and 16 hours in the light/8 hours in the dark, and with a light intensity ranging from about 30 to 45 µmol/m²/sec, for a total of 11 weeks after transplantation. After cultivation, above ground parts of the plants were placed in paper bags and dried under conditions of 22° C. and humidity of 60% for 2 weeks. The total amounts of biomass and seeds were weighed using an electronic balance.

1-3. Results

Regarding the results of 1-2-8, FIG. 3 shows a photo of the above ground parts of wild-type plants and transformed plants into which a fragment containing ORF of the PP2C (protein phosphatase 2C) gene (At3g05640) had been introduced. Also, FIG. 4 and FIG. 5 show the results of measuring the total amounts of biomass and seeds of the above ground parts of the plants.

Figure 4:
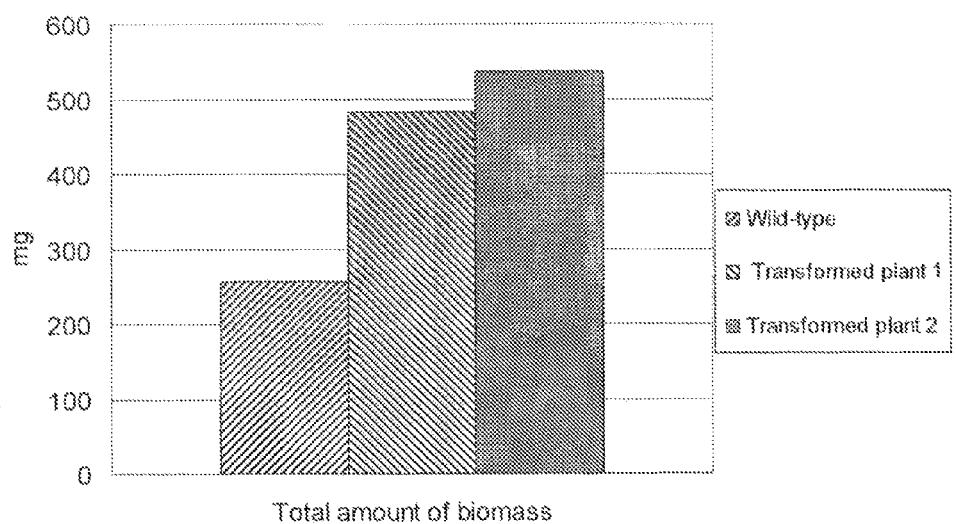
FIG. 4 is a characteristic diagram showing the results of measuring the amounts of biomass of the above ground parts of wild-type plants and transformed plants into which a fragment containing ORF of the PP2C (protein phosphatase 2C) gene (At3g05640) was introduced. The result for the wild-type plants is the average value for 12 individual wild-type plants and each result for the transformed plants is the average value for 5 individual transformed plants.
Figure 5:
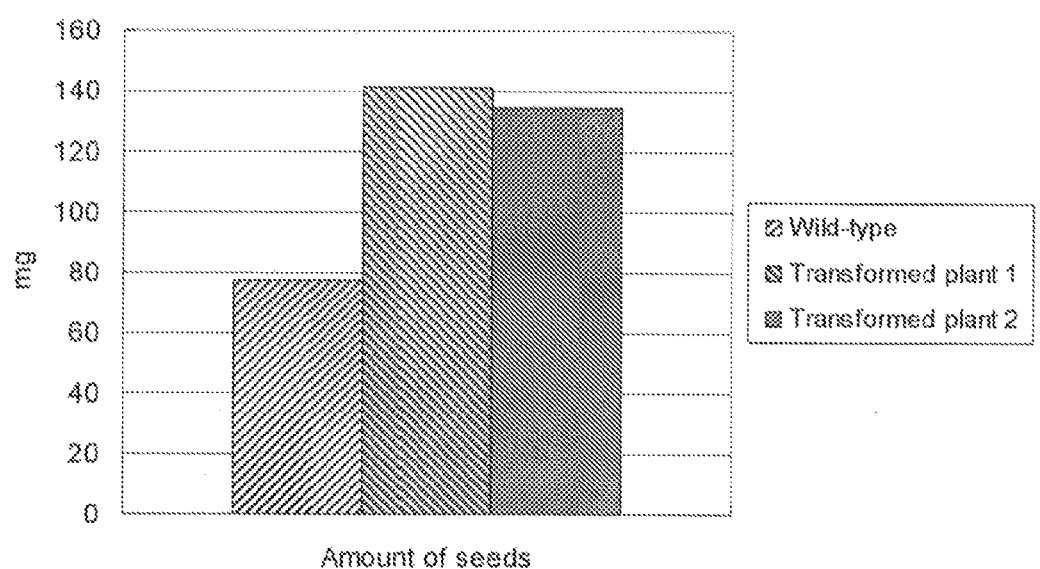
FIG. 5 is a characteristic diagram showing the results of measuring the amounts of seeds of wild-type plants and transformed plants into which a fragment containing ORF of the PP2C (protein phosphatase 2C) gene (At3g05640) was introduced. The result for wild-type plants is the average value for 12 individual wild-type plants and each result for the transformed plants is the average value for 5 individual transformed plants.

As shown in FIGS. 3, 4, and 5, it was revealed that in the case of transformed plants into which the fragment containing ORF of the PP2C (protein phosphatase 2C) gene (At3g05640) had been introduced, the total amounts of biomass of the above ground parts were much higher (about 1.9 to 2.1 times) than the amounts of the same in the cases of wild-type plants. In addition, the amounts of seeds were much more greater (by about 1.7 to 1.8 times) than the same in the cases of wild-type plants.

Reference Example 2

In this Reference example, transformed plants were prepared by introducing a glutathione-binding plastid-type fructose-1,6-bisphosphate aldolase gene (hereafter, FBA1 gene). In addition, the Examples of WO 2007-091634 A1 can be referred to.

2. Materials and Methods 2-1. Experimental Materials

An experimental material used herein was wild-type *Arabidopsis thaliana* (ecotype Col-0). *Arabidopsis* seeds were sowed in square-shaped plastic pots (6.5×6.5×5 cm) containing soil of the following three layers: vermiculite (Asahi Kogyo); KUREHA culture soil (KUREHA horticultural soil, KUREHA CORPORATION; and vermiculite; from the bottom, at a ratio of 2:2:1. Plants were then grown under conditions of a growth temperature of 22° C. and a long day (a cycle of 16 hours in the light/8 hours in the dark).

2-2. Methods 2-2-1. Obtainment of FBA1 Gene (At2g01140)

Total RNA was isolated from 4-week-old *Arabidopsis thaliana* wild-type Columbia (Col-0). RT-PCR (amount of template RNA: 5.0 µg) was performed using a Prost arfirst-strand RT-PCR kit (Stratagene), so that cDNA was prepared.

Two fragments of full-length cDNA were amplified by PCR using the following specific primers that had been designed based on the cDNA sequence (SEQ ID NO: 42) of the FBA1 gene (At2g01140). Each fragment was TA-cloned into a pGEM-T vector (Promega).

```
1F-1:
5'-GGATCCTATGGCGTCTGCTAG-3'      (SEQ ID NO: 43)

1R-1:
5'-ATCTGCAACGGTCTCGGGAGA-3'      (SEQ ID NO: 44)

1F-2:
5'-GTGTGGTCCGAGGTGTTCTTCT-3'     (SEQ ID NO: 45)

1R-2:
5'-GAGCTCGAGTAGGTGTAACCCTTG-3'   (SEQ ID NO: 46)
```

The 2 fragments were fused at the Bstp I site and then a vector (pGEM-FBA1) containing the full-length cDNA was constructed. For production of transformed plants, pGEM-FBA1 was treated with restriction enzymes BamH I and Sac I and then the fragment was introduced into a pBI121 vector.

2-2-2. Construction of Plant Expression Vector

A construct was prepared by inserting the fragment containing the FBA1 gene (At2g01140) (obtained in 2-2-1) into a plant expression vector pMAT137-HM (Matsuoka K. and Nakamura K., 1991, Proc. Natl. Acad. Sci. U.S.A. 88, 834-838).

First, the fragment containing the FBA1 gene and a NOS terminator, which had been incorporated into the pBI121 vector, was excised with Xba I and EcoR I. The resultant was incorporated into a pBluscriptII (SK+) vector (Stratagene) treated with Xba I and EcoR I. Subsequently, the fragment containing the FBA1 gene and the NOS terminator was excised with Xba I and Kpn I and then incorporated into a pMAT137-Hm vector that had been treated with Xba I and Kpn I.

2-2-3. Gene Introduction into *Arabidopsis thaliana* Using *Agrobacterium* Method The plant expression vector pMAT137-Hm constructed in 2-2-2 was introduced by electroporation (Plant Molecular Biology Mannal, Second Edition, B. G. Stanton and A. S. Robbert, Kluwer Acdemic Publishers 1994) into an *Agrobacterium tumefaciens* C58C1 strain. Next, *Agrobacterium tumefaciens* into which the plant expression vector had been introduced was introduced by the infiltration method described by Clough et al., (Steven J. Clough and Andrew F.

Bent, 1998, The Plant Journal 16, 735-743) into wild-type *Arabidopsis thaliana* (ecotype Col-0).

Selection was repeated using agar medium (Murashige-Skoog medium with a ½ concentration) containing Kanamycin as a selection marker. At the stage at which all seeds can grow in medium containing kanamycin (at a generation stably retaining traits), the expression levels of the transgene were confirmed by RT-PCR analysis, so that production of transformed plants was confirmed.

Example 1

In Example 1, the effects of oxidized glutathione (GSSG) treatment were examined for the transformed plants (hereinafter, PP2C transformed plants) prepared in Reference example 1 by introducing a fragment containing ORF of the PP2C (protein phosphatase 2C) gene (At3g05640); the transformed plants (hereinafter, FBA1 transformed plants) prepared in Reference example 2 by introducing a glutathione-binding plastid-type fructose-1,6-bisphosphate aldolase gene; and wild-type *Arabidopsis thaliana*.

3. Materials and Methods
3-1. Experimental Materials

Experimental materials used herein were seeds of the T3 generation and the following generations of the PP2C transformed plants prepared in 1-2-7, seeds of the FBA1 transformed plants prepared in 2-2-3, and seeds of wild-type *Arabidopsis thaliana* (ecotype Col-0).

Seeds of each plant type were sowed in a square-shaped plastic pot (6.5×6.5×5 cm) containing soil of the following three layers; vermiculite (Asahi Kogyo); KUREHA culture soil (KUREHA horticultural soil, KUREHA CORPORATION); and vermiculite; from the bottom, at a ratio of 2:2:1. Plants were then grown under conditions of 100 µmol/m²/sec light intensity, a growth temperature of 22° C., and a long day (a cycle of 16 hours in the light/8 hours in the dark).

3-2. Methods

Effects of Oxidized Glutathione (GSSG) on the Growth of Each Plant

Each plant (3 plants per pot) was treated 5 times in total with water alone (control) or a 1 mM GSSG solution at intervals of 1 week from the 1$^{st}$ week after planting. The growth state of each plant was observed. Treatment was performed by placing 4 pots (6.5×6.5×5 cm) on a weighing dish and adding a treatment solution (25 ml/pot/treatment) thereto. Plants were cultivated for 15 weeks after sowing. After cultivation, the above ground parts of the plants were placed in paper bags and dried under conditions of 22° C. and humidity of 60% for 2 weeks. The total amounts of biomass and seeds were weighed using an electronic balance.

3-3. Results

Figure 6:
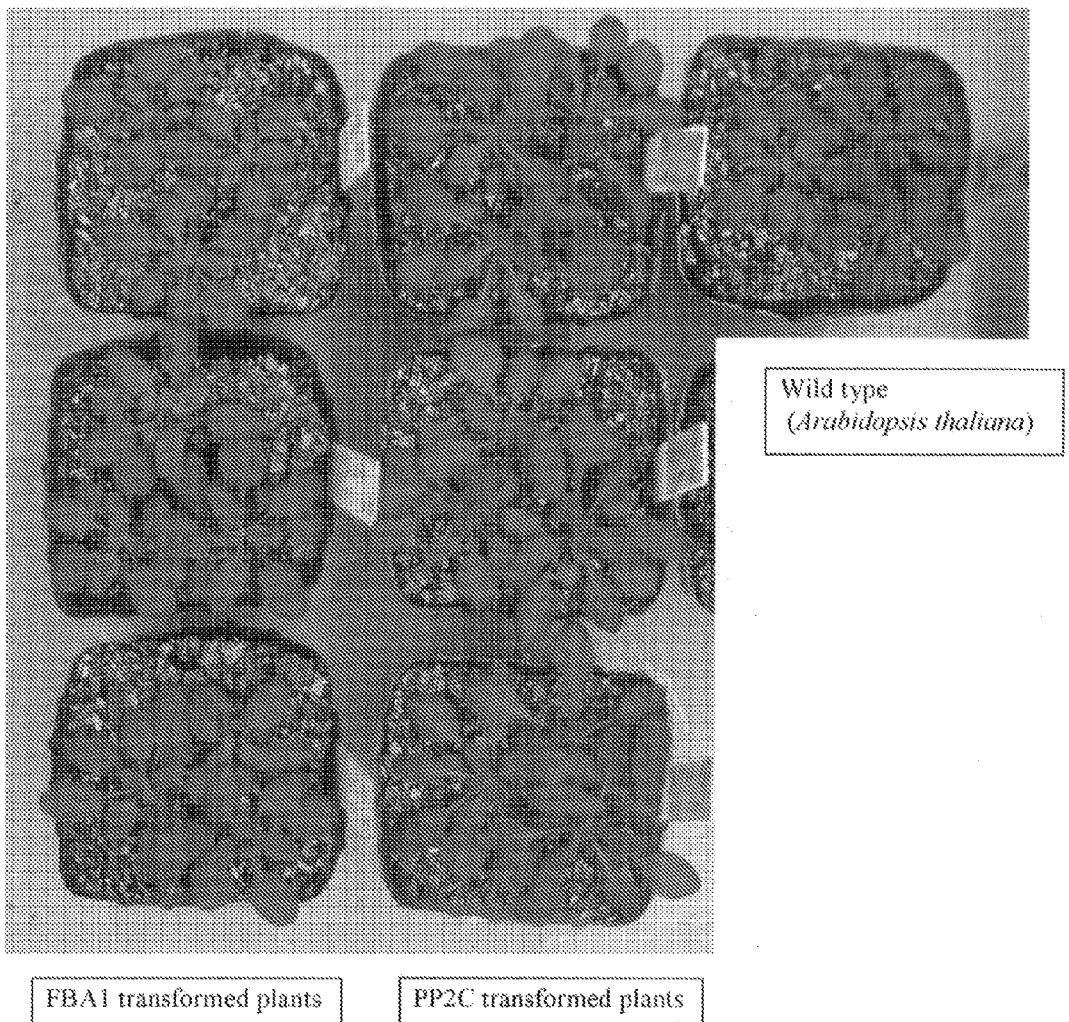
FIG. 6 is a photo showing the above ground parts of wild-type plants, transformed plants into which a PP2C gene was introduced, and transformed plants into which an FBA1 gene was introduced, which were treated with glutathione and then cultivated.

FIG. 6 shows the results of 3-2 above. Specifically, FIG. 6 shows a photo taken 3 weeks after sowing, showing the above ground parts of the PP2C transformed plants, the FBA1 transformed plants, and wild-type *Arabidopsis thaliana*, which were treated with a 1 mM GSSG solution. As shown in FIG. 6, it was revealed that in the case of PP2C transformed plants, the growth of rosette leaves was more improved compared with the FBA1 transformed plants and wild-type *Arabidopsis thaliana*.

Figure 7:
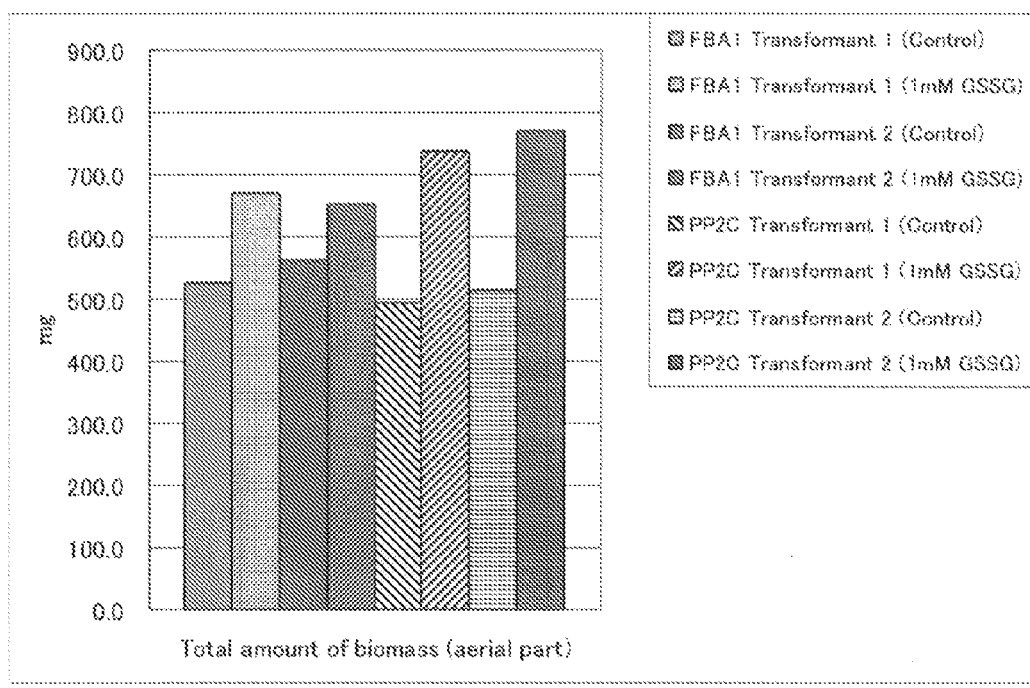
FIG. 7 is a characteristic diagram showing the results of measuring the amounts of biomass of the above ground parts of: transformed plants into which a PP2C gene was introduced therein and transformed plants into which an FBA1 gene was introduced, which were treated with glutathione and then cultivated; and the same transformed plants serving as control plants, which were treated with water.
Figure 8:
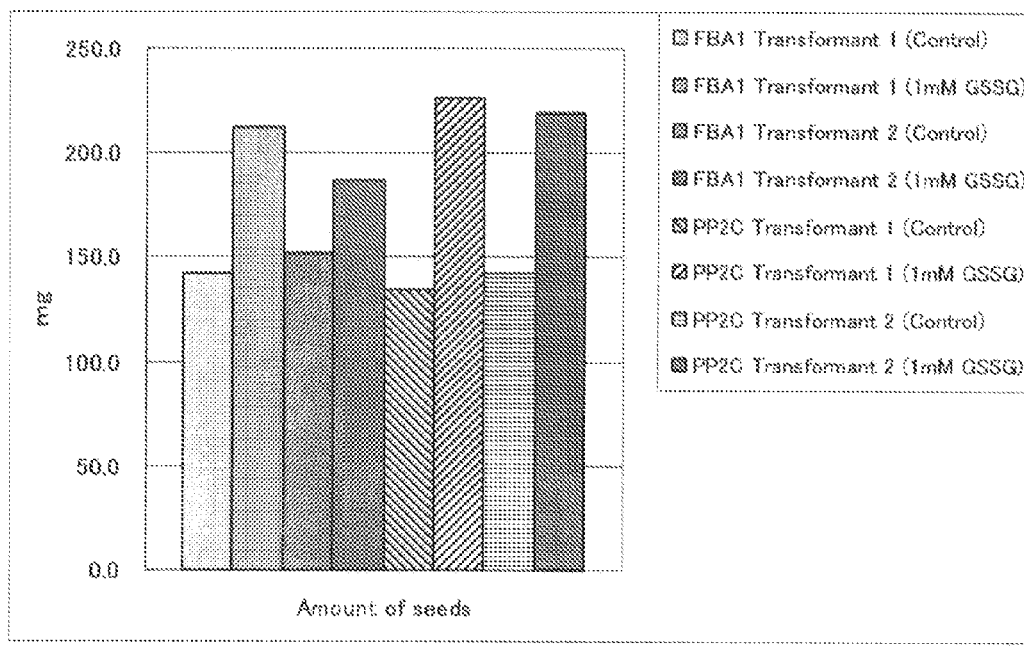
FIG. 8 is a characteristic diagram showing the results of measuring the amounts of seeds of: transformed plants into which a PP2C gene was introduced and transformed plants into which an FBA1 gene was introduced, which were treated with glutathione and then cultivated; and the same transformed plants serving as control plants, which were treated with water.

Also, FIG. 7 shows the results of measuring the total amounts of biomass of the above ground parts and FIG. 8 shows the results of measuring the amounts of seeds. In addition, the amounts of biomass and the amounts of seeds shown in FIGS. 7 and 8 were both average values found by measuring the amounts of biomass of 6 pots (each pot containing 3 plants) and then calculating the average value. As shown in FIG. 7, it was revealed that in the case of PP2C transformed plants treated with glutathione, the total amount of biomass of the above ground parts was improved by about 49% compared with the same in cases involving treatment with water alone (control). It was also revealed that in the case of FBA1 transformed plants treated with glutathione, the total amount of biomass of the above ground parts was improved by about 17% to 27% compared with the same in cases involving treatment with water alone (control).

Meanwhile, as shown in FIG. 8, it was revealed that in the case of the PP2C transformed plants treated with glutathione, the amount of seeds was improved by about 54% to 69% compared with the same in cases involving treatment with water alone (control). Also, it was revealed that in the case of the FBA1 transformed plants treated with glutathione, the amount of seeds was improved by about 23% to 49% compared with the same in cases involving treatment with water alone (control).

As described above, it could be confirmed that in the case of the PP2C transformed plants, the effects of increasing the production of biomass and seeds by glutathione treatment were further enhanced in comparison with the FBA1 transformed plants.

What is claimed is:

1. A method for increasing production of a plant biomass and/or seeds, comprising a step of supplying glutathione to a plant into which an exogenous gene encoding a protein phosphatase 2C has been introduced,
wherein said protein phosphatase 2C is selected from the group consisting of (a) and (b):
(a) a protein comprising the amino acid sequence of SEQ ID NO: 5; and
(b) a protein comprising an amino acid sequence having at least 95% identity to the amino acid sequence of SEQ ID NO: 5, having protein phosphatase 2C activity,
and wherein said step of supplying glutathione increases plant biomass and/or seed production in comparison to when the plant into which the gene encoding the protein phosphatase 2C has been introduced is not supplied with the glutathione.

2. The method according to claim 1, wherein the glutathione is oxidized glutathione.

3. The method according to claim 1, whereby a solution containing the glutathione is supplied to soil in which seeds of the plant have been sowed.

4. A method for producing a plant, comprising a step of supplying glutathione to a plant into which an exogenous gene encoding a protein phosphatase 2C has been introduced,
wherein said protein phosphatase 2C is selected from the group consisting of (a) and (b):
(a) a protein comprising the amino acid sequence of SEQ ID NO: 5; and (b) a protein comprising an amino acid sequence having at least 95% identity to the amino acid sequence of SEQ ID NO: 5, having protein phosphatase 2C activity.

5. The production method according to claim 4, wherein the glutathione is oxidized glutathione.

6. The method according to claim 4, whereby a solution containing the glutathione is supplied to soil in which seeds of the plant have been sowed.

* * * * *

SEQUENCE LISTING

```
<160> NUMBER OF SEQ ID NOS: 46

<210> SEQ ID NO 1
<211> LENGTH: 19
<212> TYPE: PRT
<213> ORGANISM: Artificial
<220> FEATURE:
<223> OTHER INFORMATION: A consensus sequence in a protein phosphatase
<220> FEATURE:
<221> NAME/KEY: misc_feature
<222> LOCATION: (1)..(1)
<223> OTHER INFORMATION: Xaa can be any naturally occurring amino acid,
      or preferably L or F
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
```

-continued

```
<223> OTHER INFORMATION: Xaa can be any naturally occurring amino acid,
      or preferably V, I or M
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid,
      or preferably S or A
<220> FEATURE:
<221> NAME/KEY: misc_feature
<222> LOCATION: (17)..(17)
<223> OTHER INFORMATION: Xaa can be any naturally occurring amino acid,
      or preferably K, R, Q or N
<220> FEATURE:
<221> NAME/KEY: misc_feature
<222> LOCATION: (18)..(18)
<223> OTHER INFORMATION: Xaa can be any naturally occurring amino acid

<400> SEQUENCE: 1

Xaa Xaa Gly Xaa Phe Asp Gly His Gly Xaa Xaa Gly Xaa Xaa Xaa Xaa
1               5                   10                  15

Xaa Xaa Val

<210> SEQ ID NO 2
<211> LENGTH: 27
<212> TYPE: PRT
<213> ORGANISM: Artificial
<220> FEATURE:
<223> OTHER INFORMATION: A consensus sequence in a protein phosphatase
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid,
      or preferably G, A or S
<220> FEATURE:
<221> NAME/KEY: misc_feature
<222> LOCATION: (6)..(6)
<223> OTHER INFORMATION: Xaa can be any naturally occurring amino acid,
      or preferably V, L or I
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid,
      or preferably I, V, F, M or L
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid,
      or preferably G or A
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid,
      or preferably L, V or I
```

```
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid,
      or preferably I, V or M
<220> FEATURE:
<221> NAME/KEY: misc_feature
<222> LOCATION: (18)..(18)
<223> OTHER INFORMATION: Xaa can be any naturally occurring amino acid,
      or preferably A or G
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid,
      or preferably D or H
<220> FEATURE:
<221> NAME/KEY: misc_feature
<222> LOCATION: (26)..(26)
<223> OTHER INFORMATION: Xaa can be any naturally occurring amino acid,
      or preferably V or I
<220> FEATURE:
<221> NAME/KEY: misc_feature
<222> LOCATION: (27)..(27)
<223> OTHER INFORMATION: Xaa can be any naturally occurring amino acid,
      or preferably L, M or I

<400> SEQUENCE: 2

Ser Gly Xaa Thr Xaa Xaa Xaa Xaa Xaa Xaa Xaa Xaa Xaa Xaa Xaa
1               5                   10                  15

Xaa Xaa Asn Xaa Gly Xaa Ser Arg Ala Xaa Xaa
            20                  25

<210> SEQ ID NO 3
<211> LENGTH: 56
<212> TYPE: PRT
<213> ORGANISM: Artificial
<220> FEATURE:
<223> OTHER INFORMATION: A consensus sequence in a protein phosphatase
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid,
      or preferably M, V or F
<220> FEATURE:
<221> NAME/KEY: misc_feature
<222> LOCATION: (5)..(5)
<223> OTHER INFORMATION: Xaa can be any naturally occurring amino acid,
      or preferably S, A or T
<220> FEATURE:
<221> NAME/KEY: misc_feature
<222> LOCATION: (7)..(7)
<223> OTHER INFORMATION: Xaa can be any naturally occurring amino acid,
      or preferably A or S
<220> FEATURE:
<221> NAME/KEY: misc_feature
<222> LOCATION: (8)..(8)
<223> OTHER INFORMATION: Xaa can be any naturally occurring amino acid,
      or preferably F, I or V
<220> FEATURE:
<221> NAME/KEY: misc_feature
<222> LOCATION: (11)..(13)
<223> OTHER INFORMATION: Xaa can be any naturally occurring amino acid
<220> FEATURE:
<221> NAME/KEY: misc_feature
<222> LOCATION: (14)..(14)
```

-continued

```
<223> OTHER INFORMATION: Xaa can be any naturally occurring amino acid,
      or preferably K or E
<220> FEATURE:
<221> NAME/KEY: misc_feature
<222> LOCATION: (15)..(16)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid,
      or preferably V or L
<220> FEATURE:
<221> NAME/KEY: misc_feature
<222> LOCATION: (19)..(19)
<223> OTHER INFORMATION: Xaa can be any naturally occurring amino acid,
      or preferably I or V
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid,
      or preferably E, Q or D
<220> FEATURE:
<221> NAME/KEY: misc_feature
<222> LOCATION: (24)..(24)
<223> OTHER INFORMATION: Xaa can be any naturally occurring amino acid,
      or preferably I, V or F
<220> FEATURE:
<221> NAME/KEY: misc_feature
<222> LOCATION: (25)..(28)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid,
      or preferably I, L or V
<220> FEATURE:
<221> NAME/KEY: misc_feature
<222> LOCATION: (30)..(30)
<223> OTHER INFORMATION: Xaa can be any naturally occurring amino acid,
      or preferably T or S
<220> FEATURE:
<221> NAME/KEY: misc_feature
<222> LOCATION: (31)..(32)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid,
      or preferably D, N or H
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid,
      or preferably F or Y
<220> FEATURE:
<221> NAME/KEY: misc_feature
<222> LOCATION: (36)..(36)
<223> OTHER INFORMATION: Xaa can be any naturally occurring amino acid,
      or preferably L, I, V or F
<220> FEATURE:
<221> NAME/KEY: misc_feature
<222> LOCATION: (37)..(37)
<223> OTHER INFORMATION: Xaa can be any naturally occurring amino acid,
      or preferably V, L or I
<220> FEATURE:
<221> NAME/KEY: misc_feature
<222> LOCATION: (38)..(38)
<223> OTHER INFORMATION: Xaa can be any naturally occurring amino acid,
```

```
          or preferably L or V
<220> FEATURE:
<221> NAME/KEY: misc_feature
<222> LOCATION: (40)..(40)
<223> OTHER INFORMATION: Xaa can be any naturally occurring amino acid,
      or preferably T or S
<220> FEATURE:
<221> NAME/KEY: misc_feature
<222> LOCATION: (43)..(43)
<223> OTHER INFORMATION: Xaa can be any naturally occurring amino acid,
      or preferably V, I or M
<220> FEATURE:
<221> NAME/KEY: misc_feature
<222> LOCATION: (44)..(44)
<223> OTHER INFORMATION: Xaa can be any naturally occurring amino acid,
      or preferably W or F
<220> FEATURE:
<221> NAME/KEY: misc_feature
<222> LOCATION: (45)..(45)
<223> OTHER INFORMATION: Xaa can be any naturally occurring amino acid,
      or preferably D or E
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid,
      or preferably L, I or M
<220> FEATURE:
<221> NAME/KEY: misc_feature
<222> LOCATION: (48)..(48)
<223> OTHER INFORMATION: Xaa can be any naturally occurring amino acid,
      or preferably S, T or P
<220> FEATURE:
<221> NAME/KEY: misc_feature
<222> LOCATION: (49)..(49)
<223> OTHER INFORMATION: Xaa can be any naturally occurring amino acid,
      or preferably N or S
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid,
      or preferably V or A
<220> FEATURE:
<221> NAME/KEY: misc_feature
<222> LOCATION: (53)..(54)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid,
      or preferably L, V, I or M
<220> FEATURE:
<221> NAME/KEY: misc_feature
<222> LOCATION: (56)..(56)
<223> OTHER INFORMATION: Xaa can be any naturally occurring amino acid,
      or preferably I or V

<400> SEQUENCE: 3

Gly Xaa Ala Xaa Xaa Arg Xaa Xaa Gly Asp Xaa Xaa Xaa Xaa Xaa Xaa
1               5                   10                  15

Gly Xaa Xaa Xaa Xaa Pro Xaa Xaa Xaa Xaa Xaa Xaa Xaa Xaa Xaa Xaa
            20                  25                  30

Xaa Xaa Xaa Xaa Xaa Xaa Ala Xaa Asp Gly Xaa Xaa Xaa Xaa Xaa Xaa
        35                  40                  45

Xaa Xaa Xaa Xaa Xaa Xaa Xaa Xaa
```

<210> SEQ ID NO 4
<211> LENGTH: 1077
<212> TYPE: DNA
<213> ORGANISM: Arabidopsis thaliana
<220> FEATURE:
<221> NAME/KEY: CDS
<222> LOCATION: (1)..(1077)

<400> SEQUENCE: 4

| | | | | | | | | | | | | | | | | |
|---|---|---|---|---|---|---|---|---|---|---|---|---|---|---|---|---|
| atg | gga | cat | ttc | tct | tcc | atg | ttc | aac | ggt | ata | gct | aga | tcc | ttc | tcg | 48 |
| Met | Gly | His | Phe | Ser | Ser | Met | Phe | Asn | Gly | Ile | Ala | Arg | Ser | Phe | Ser | |
| 1 | | | | 5 | | | | | 10 | | | | | 15 | | |
| atc | aag | aaa | gcg | aag | aac | atc | aac | agc | agc | aaa | agc | tac | gct | aag | gaa | 96 |
| Ile | Lys | Lys | Ala | Lys | Asn | Ile | Asn | Ser | Ser | Lys | Ser | Tyr | Ala | Lys | Glu | |
| | | | 20 | | | | | 25 | | | | | 30 | | | |
| gcc | aca | gat | gaa | atg | gcg | aga | gag | gcg | aag | aag | aag | gaa | ctt | att | ttg | 144 |
| Ala | Thr | Asp | Glu | Met | Ala | Arg | Glu | Ala | Lys | Lys | Lys | Glu | Leu | Ile | Leu | |
| | 35 | | | | | 40 | | | | | 45 | | | | | |
| aga | tcc | tct | ggt | tgc | att | aat | gca | gat | gga | tct | aat | aac | ttg | gct | tct | 192 |
| Arg | Ser | Ser | Gly | Cys | Ile | Asn | Ala | Asp | Gly | Ser | Asn | Asn | Leu | Ala | Ser | |
| 50 | | | | | 55 | | | | | 60 | | | | | | |
| gtt | ttc | tct | aga | cgc | ggt | gag | aaa | ggc | gtt | aat | cag | gac | tgt | gcc | atc | 240 |
| Val | Phe | Ser | Arg | Arg | Gly | Glu | Lys | Gly | Val | Asn | Gln | Asp | Cys | Ala | Ile | |
| 65 | | | | | 70 | | | | | 75 | | | | | 80 | |
| gtc | tgg | gag | gga | tat | ggg | tgt | caa | gaa | gac | atg | ata | ttc | tgt | ggg | ata | 288 |
| Val | Trp | Glu | Gly | Tyr | Gly | Cys | Gln | Glu | Asp | Met | Ile | Phe | Cys | Gly | Ile | |
| | | | | 85 | | | | | 90 | | | | | 95 | | |
| ttc | gat | gga | cat | ggt | ccc | tgg | gga | cac | ttt | gtt | tct | aaa | caa | gtc | aga | 336 |
| Phe | Asp | Gly | His | Gly | Pro | Trp | Gly | His | Phe | Val | Ser | Lys | Gln | Val | Arg | |
| | | | 100 | | | | | 105 | | | | | 110 | | | |
| aac | tca | atg | cct | ata | tct | ttg | ctc | tgt | aac | tgg | aaa | gag | act | ctt | tct | 384 |
| Asn | Ser | Met | Pro | Ile | Ser | Leu | Leu | Cys | Asn | Trp | Lys | Glu | Thr | Leu | Ser | |
| | 115 | | | | | 120 | | | | | 125 | | | | | |
| cag | acc | aca | ata | gca | gaa | ccc | gat | aaa | gag | cta | cag | cgg | ttt | gca | atc | 432 |
| Gln | Thr | Thr | Ile | Ala | Glu | Pro | Asp | Lys | Glu | Leu | Gln | Arg | Phe | Ala | Ile | |
| 130 | | | | | 135 | | | | | 140 | | | | | | |
| tgg | aaa | tac | tca | ttc | ctc | aaa | acc | tgt | gaa | gct | gtt | gat | ctg | gag | ctt | 480 |
| Trp | Lys | Tyr | Ser | Phe | Leu | Lys | Thr | Cys | Glu | Ala | Val | Asp | Leu | Glu | Leu | |
| 145 | | | | | 150 | | | | | 155 | | | | | 160 | |
| gag | cat | cac | cga | aag | ata | gat | tct | ttc | aac | agc | ggt | acg | acc | gct | cta | 528 |
| Glu | His | His | Arg | Lys | Ile | Asp | Ser | Phe | Asn | Ser | Gly | Thr | Thr | Ala | Leu | |
| | | | | 165 | | | | | 170 | | | | | 175 | | |
| acc | att | gtg | aga | cag | ggt | gat | gtt | att | tat | ata | gca | aac | gtc | ggg | gat | 576 |
| Thr | Ile | Val | Arg | Gln | Gly | Asp | Val | Ile | Tyr | Ile | Ala | Asn | Val | Gly | Asp | |
| | | | 180 | | | | | 185 | | | | | 190 | | | |
| tca | cgt | gcg | gta | ttg | gcc | aca | gtt | tca | gac | gaa | gga | agc | ttg | gtc | gcg | 624 |
| Ser | Arg | Ala | Val | Leu | Ala | Thr | Val | Ser | Asp | Glu | Gly | Ser | Leu | Val | Ala | |
| | 195 | | | | | 200 | | | | | 205 | | | | | |
| gtt | cag | ctc | acc | gta | gat | ttc | aag | cca | aac | ctg | cct | cag | gag | gaa | gag | 672 |
| Val | Gln | Leu | Thr | Val | Asp | Phe | Lys | Pro | Asn | Leu | Pro | Gln | Glu | Glu | Glu | |
| 210 | | | | | 215 | | | | | 220 | | | | | | |
| cgg | ata | atc | gga | tgc | aac | ggg | aga | gta | ttt | tgc | ctt | caa | gat | gag | cca | 720 |
| Arg | Ile | Ile | Gly | Cys | Asn | Gly | Arg | Val | Phe | Cys | Leu | Gln | Asp | Glu | Pro | |
| 225 | | | | | 230 | | | | | 235 | | | | | 240 | |
| ggg | gtc | cac | cgt | gta | tgg | caa | cca | gta | gat | gaa | tct | ccg | ggg | ctc | gca | 768 |
| Gly | Val | His | Arg | Val | Trp | Gln | Pro | Val | Asp | Glu | Ser | Pro | Gly | Leu | Ala | |
| | | | | 245 | | | | | 250 | | | | | 255 | | |
| atg | tca | aga | gca | ttc | gga | gac | tat | tgt | atc | aaa | gat | tac | gga | ttg | gtc | 816 |
| Met | Ser | Arg | Ala | Phe | Gly | Asp | Tyr | Cys | Ile | Lys | Asp | Tyr | Gly | Leu | Val | |
| | | | 260 | | | | | 265 | | | | | 270 | | | |

```
tca gtg cct gaa gtc act cag agg cat ata tcc att aga gac cag ttt        864
Ser Val Pro Glu Val Thr Gln Arg His Ile Ser Ile Arg Asp Gln Phe
        275                 280                 285 ata atc ttg gcc act gat ggg gta tgg gat gtg ata tca aac caa gag        912
Ile Ile Leu Ala Thr Asp Gly Val Trp Asp Val Ile Ser Asn Gln Glu
        290                 295                 300 gcc ata gat att gtt tcc tcg acg gcg gag cgg gca aaa gct gcc aag        960
Ala Ile Asp Ile Val Ser Ser Thr Ala Glu Arg Ala Lys Ala Ala Lys
305                 310                 315                 320 cga ctg gta cag caa gca gtt agg gct tgg aat aga aag aga cgc gga       1008
Arg Leu Val Gln Gln Ala Val Arg Ala Trp Asn Arg Lys Arg Arg Gly
                325                 330                 335 atc gcc atg gat gat atc tct gcc gtg tgc ctc ttc ttc cat tct tca       1056
Ile Ala Met Asp Asp Ile Ser Ala Val Cys Leu Phe Phe His Ser Ser
            340                 345                 350 tcg tcg tcg cca tct cta tag                                           1077
Ser Ser Ser Pro Ser Leu
            355
```

<210> SEQ ID NO 5
<211> LENGTH: 358
<212> TYPE: PRT
<213> ORGANISM: Arabidopsis thaliana

<400> SEQUENCE: 5

```
Met Gly His Phe Ser Ser Met Phe Asn Gly Ile Ala Arg Ser Phe Ser
1               5                   10                  15

Ile Lys Lys Ala Lys Asn Ile Asn Ser Ser Lys Ser Tyr Ala Lys Glu
            20                  25                  30

Ala Thr Asp Glu Met Ala Arg Glu Ala Lys Lys Lys Glu Leu Ile Leu
        35                  40                  45

Arg Ser Ser Gly Cys Ile Asn Ala Asp Gly Ser Asn Asn Leu Ala Ser
    50                  55                  60

Val Phe Ser Arg Arg Gly Glu Lys Gly Val Asn Gln Asp Cys Ala Ile
65                  70                  75                  80

Val Trp Glu Gly Tyr Gly Cys Gln Glu Asp Met Ile Phe Cys Gly Ile
                85                  90                  95

Phe Asp Gly His Gly Pro Trp Gly His Phe Val Ser Lys Gln Val Arg
            100                 105                 110

Asn Ser Met Pro Ile Ser Leu Leu Cys Asn Trp Lys Glu Thr Leu Ser
        115                 120                 125

Gln Thr Thr Ile Ala Glu Pro Asp Lys Glu Leu Gln Arg Phe Ala Ile
    130                 135                 140

Trp Lys Tyr Ser Phe Leu Lys Thr Cys Glu Ala Val Asp Leu Glu Leu
145                 150                 155                 160

Glu His His Arg Lys Ile Asp Ser Phe Asn Ser Gly Thr Thr Ala Leu
                165                 170                 175

Thr Ile Val Arg Gln Gly Asp Val Ile Tyr Ile Ala Asn Val Gly Asp
            180                 185                 190

Ser Arg Ala Val Leu Ala Thr Val Ser Asp Glu Gly Ser Leu Val Ala
        195                 200                 205

Val Gln Leu Thr Val Asp Phe Lys Pro Asn Leu Pro Gln Glu Glu Glu
    210                 215                 220

Arg Ile Ile Gly Cys Asn Gly Arg Val Phe Cys Leu Gln Asp Glu Pro
225                 230                 235                 240

Gly Val His Arg Val Trp Gln Pro Val Asp Glu Ser Pro Gly Leu Ala
                245                 250                 255
```

```
Met Ser Arg Ala Phe Gly Asp Tyr Cys Ile Lys Asp Tyr Gly Leu Val
            260                 265                 270

Ser Val Pro Glu Val Thr Gln Arg His Ile Ser Ile Arg Asp Gln Phe
        275                 280                 285

Ile Ile Leu Ala Thr Asp Gly Val Trp Asp Val Ile Ser Asn Gln Glu
    290                 295                 300

Ala Ile Asp Ile Val Ser Ser Thr Ala Glu Arg Ala Lys Ala Ala Lys
305                 310                 315                 320

Arg Leu Val Gln Gln Ala Val Arg Ala Trp Asn Arg Lys Arg Arg Gly
                325                 330                 335

Ile Ala Met Asp Asp Ile Ser Ala Val Cys Leu Phe Phe His Ser Ser
            340                 345                 350

Ser Ser Ser Pro Ser Leu
            355

<210> SEQ ID NO 6
<211> LENGTH: 1176
<212> TYPE: DNA
<213> ORGANISM: Oryza sativa
<220> FEATURE:
<221> NAME/KEY: CDS
<222> LOCATION: (1)..(1176)

<400> SEQUENCE: 6 atg cgg cac atc tcg tcg ctg ctg cag ggg ctg gcg cgc tcg ctg tcg    48
Met Arg His Ile Ser Ser Leu Leu Gln Gly Leu Ala Arg Ser Leu Ser
1               5                   10                  15 gtg ggg aag gag agg aag ggc ggc gac ggc gac gac ggg aag gcg gcg    96
Val Gly Lys Glu Arg Lys Gly Gly Asp Gly Asp Asp Gly Lys Ala Ala
            20                  25                  30 gcg gcg acg gcg acg gcg gtg ctg agg aca tcg ggg acg ctg tgg ggc   144
Ala Ala Thr Ala Thr Ala Val Leu Arg Thr Ser Gly Thr Leu Trp Gly
        35                  40                  45 gag ggc tct gag acg ttc gcc gcc gtc tgc tcc cgc cgc ggc gag aag   192
Glu Gly Ser Glu Thr Phe Ala Ala Val Cys Ser Arg Arg Gly Glu Lys
    50                  55                  60 ggc atc aac cag gac tgc tcc atc gtc tgc gag gga ttc ggg tgc gag   240
Gly Ile Asn Gln Asp Cys Ser Ile Val Cys Glu Gly Phe Gly Cys Glu
65                  70                  75                  80 gag ggg agc gtg ttg tgc ggc atc ttc gac ggg cac ggg cag tgg ggc   288
Glu Gly Ser Val Leu Cys Gly Ile Phe Asp Gly His Gly Gln Trp Gly
                85                  90                  95 cac tac gtg gcg aag gcg gtg agg gag tcg ctg ccg ccg gcg ctg ctc   336
His Tyr Val Ala Lys Ala Val Arg Glu Ser Leu Pro Pro Ala Leu Leu
            100                 105                 110 cgg cgg tgg cgg gag gcc gtg acg ctg gcg gcg ctc atc gac ggc ggc   384
Arg Arg Trp Arg Glu Ala Val Thr Leu Ala Ala Leu Ile Asp Gly Gly
        115                 120                 125 gag aag cgg ctc tgc gag tgc cgg ccc gac ctg tgg cgc cag tcc tac   432
Glu Lys Arg Leu Cys Glu Cys Arg Pro Asp Leu Trp Arg Gln Ser Tyr
    130                 135                 140 ctg gcc gcc tgc gcc gcc gtc gac gcc gag ctc cgc gcc agc cgc cgc   480
Leu Ala Ala Cys Ala Ala Val Asp Ala Glu Leu Arg Ala Ser Arg Arg
145                 150                 155                 160 ctc gac gcc gtc cac agc ggc tgc acc gcg ctg tcc ctc gtc aag cac   528
Leu Asp Ala Val His Ser Gly Cys Thr Ala Leu Ser Leu Val Lys His
                165                 170                 175 ggc gac ctc ctc gtc gtc gcc aac gtc ggc gac tcg cgc gcc gtc ctg   576
Gly Asp Leu Leu Val Val Ala Asn Val Gly Asp Ser Arg Ala Val Leu
            180                 185                 190
```

```
gcc acc gcc tcc ccc gac gac ggt ggc ggc gcc cgc ctc gcc gcc gtg      624
Ala Thr Ala Ser Pro Asp Asp Gly Gly Gly Ala Arg Leu Ala Ala Val
            195                 200                 205 cag ctc acc gtc gac ttc aag ccc aac ctg ccc cag gag agg gag agg      672
Gln Leu Thr Val Asp Phe Lys Pro Asn Leu Pro Gln Glu Arg Glu Arg
210                 215                 220 atc atg gag tgc aac ggg agg gtg cag tgc ctc gcc gac gag ccc ggg      720
Ile Met Glu Cys Asn Gly Arg Val Gln Cys Leu Ala Asp Glu Pro Gly
225                 230                 235                 240 gtg cac cgg gtg tgg cgg ccg gac agg gag ggc cca ggc ctc gcc atg      768
Val His Arg Val Trp Arg Pro Asp Arg Glu Gly Pro Gly Leu Ala Met
                245                 250                 255 tcg cgc gcc ttc ggc gac tac tgc gtc aag gat tac ggc gtc atc tcg      816
Ser Arg Ala Phe Gly Asp Tyr Cys Val Lys Asp Tyr Gly Val Ile Ser
            260                 265                 270 gcg ccg gag gtg acg cac cgc cgg atc acc gcc cag gac cac ttc gtc      864
Ala Pro Glu Val Thr His Arg Arg Ile Thr Ala Gln Asp His Phe Val
        275                 280                 285 atc ctc gcc acc gac ggg gac aaa cat ctc aac ttg ttc gtc ttc gtc      912
Ile Leu Ala Thr Asp Gly Asp Lys His Leu Asn Leu Phe Val Phe Val
290                 295                 300 tgc gcg gca ggt gtg gga cgt ggt gtc gaa cga gga ggc ggt gca gat      960
Cys Ala Ala Gly Val Gly Arg Gly Val Glu Arg Gly Gly Gly Ala Asp
305                 310                 315                 320 cgt ggc gtc ggc gcc gga gag gga gaa ggc ggc gaa gcg gct cgt cga     1008
Arg Gly Val Gly Ala Gly Glu Gly Glu Gly Gly Glu Ala Ala Arg Arg
                325                 330                 335 gtt cgc cgt ccg ggc atg gag gcg caa gcg ccg ggg cat cgc cgt cga     1056
Val Arg Arg Pro Gly Met Glu Ala Gln Ala Pro Gly His Arg Arg Arg
            340                 345                 350 cga ctg ctc ggc gat ctg cct ctt ctt cca ctc gcc gcc gtc cta aac     1104
Arg Leu Leu Gly Asp Leu Pro Leu Leu Pro Leu Ala Ala Val Leu Asn
        355                 360                 365 aac aca cac gct gac acg cac gca gcc aac aaa aac cgc aca cgc cga     1152
Asn Thr His Ala Asp Thr His Ala Ala Asn Lys Asn Arg Thr Arg Arg
370                 375                 380 cga caa tgt cgc cgt cgt cgt tga                                     1176
Arg Gln Cys Arg Arg Arg Arg
385                 390
```

<210> SEQ ID NO 7
<211> LENGTH: 391
<212> TYPE: PRT
<213> ORGANISM: Oryza sativa

<400> SEQUENCE: 7

```
Met Arg His Ile Ser Ser Leu Leu Gln Gly Leu Ala Arg Ser Leu Ser
1               5                   10                  15

Val Gly Lys Glu Arg Lys Gly Gly Asp Gly Asp Gly Lys Ala Ala
            20                  25                  30

Ala Ala Thr Ala Thr Ala Val Leu Arg Thr Ser Gly Thr Leu Trp Gly
        35                  40                  45

Glu Gly Ser Glu Thr Phe Ala Ala Val Cys Ser Arg Arg Gly Glu Lys
    50                  55                  60

Gly Ile Asn Gln Asp Cys Ser Ile Val Cys Glu Gly Phe Gly Cys Glu
65                  70                  75                  80

Glu Gly Ser Val Leu Cys Gly Ile Phe Asp Gly His Gly Gln Trp Gly
                85                  90                  95

His Tyr Val Ala Lys Ala Val Arg Glu Ser Leu Pro Pro Ala Leu Leu
```

```
                    100                 105                 110
Arg Arg Trp Arg Glu Ala Val Thr Leu Ala Ala Leu Ile Asp Gly Gly
            115                 120                 125

Glu Lys Arg Leu Cys Glu Cys Arg Pro Asp Leu Trp Arg Gln Ser Tyr
        130                 135                 140

Leu Ala Ala Cys Ala Ala Val Asp Ala Glu Leu Arg Ala Ser Arg Arg
145                 150                 155                 160

Leu Asp Ala Val His Ser Gly Cys Thr Ala Leu Ser Leu Val Lys His
                165                 170                 175

Gly Asp Leu Leu Val Val Ala Asn Val Gly Asp Ser Arg Ala Val Leu
            180                 185                 190

Ala Thr Ala Ser Pro Asp Asp Gly Gly Ala Arg Leu Ala Ala Val
        195                 200                 205

Gln Leu Thr Val Asp Phe Lys Pro Asn Leu Pro Gln Glu Arg Glu Arg
    210                 215                 220

Ile Met Glu Cys Asn Gly Arg Val Gln Cys Leu Ala Asp Glu Pro Gly
225                 230                 235                 240

Val His Arg Val Trp Arg Pro Asp Arg Glu Gly Pro Gly Leu Ala Met
                245                 250                 255

Ser Arg Ala Phe Gly Asp Tyr Cys Val Lys Asp Tyr Gly Val Ile Ser
            260                 265                 270

Ala Pro Glu Val Thr His Arg Arg Ile Thr Ala Gln Asp His Phe Val
        275                 280                 285

Ile Leu Ala Thr Asp Gly Asp Lys His Leu Asn Leu Phe Val Phe Val
    290                 295                 300

Cys Ala Ala Gly Val Gly Arg Gly Val Glu Arg Gly Gly Gly Ala Asp
305                 310                 315                 320

Arg Gly Val Gly Ala Gly Glu Gly Glu Gly Glu Ala Ala Arg Arg
                325                 330                 335

Val Arg Arg Pro Gly Met Glu Ala Gln Ala Pro Gly His Arg Arg
            340                 345                 350

Arg Leu Leu Gly Asp Leu Pro Leu Leu Pro Leu Ala Ala Val Leu Asn
        355                 360                 365

Asn Thr His Ala Asp Thr His Ala Ala Asn Lys Asn Arg Thr Arg Arg
    370                 375                 380

Arg Gln Cys Arg Arg Arg
385                 390

<210> SEQ ID NO 8
<211> LENGTH: 1263
<212> TYPE: DNA
<213> ORGANISM: Oryza sativa
<220> FEATURE:
<221> NAME/KEY: CDS
<222> LOCATION: (1)..(1263)

<400> SEQUENCE: 8 atg ggg ata tgc tgc agc aag ggg aag gag gag ctt gag gag gag gga      48
Met Gly Ile Cys Cys Ser Lys Gly Lys Glu Glu Leu Glu Glu Glu Gly
1               5                   10                  15 ttt cca tgg aag cac gac gcc ttc ttc cac gac cag ctt tgg agc gct      96
Phe Pro Trp Lys His Asp Ala Phe Phe His Asp Gln Leu Trp Ser Ala
                20                  25                  30 ggc gtc tcc atg cac acc aag caa ggc tgg aag ggc gcc aac cag gac     144
Gly Val Ser Met His Thr Lys Gln Gly Trp Lys Gly Ala Asn Gln Asp
            35                  40                  45 gcc atg act acc tgc cag gac ttt gcg ggg cac aag ggc cag ata ttt     192
Ala Met Thr Thr Cys Gln Asp Phe Ala Gly His Lys Gly Gln Ile Phe
```

```
Ala Met Thr Thr Cys Gln Asp Phe Ala Gly His Lys Gly Gln Ile Phe
    50                  55                  60 tgt gga gtt ttt gat ggg cat ggc cct ctc gga agg gaa gtt gct cgc       240
Cys Gly Val Phe Asp Gly His Gly Pro Leu Gly Arg Glu Val Ala Arg
65                      70                  75                  80 cat gtc cgc gac gtc ctt cca gtg aaa cta tcc tcc tct ttg gca ctg       288
His Val Arg Asp Val Leu Pro Val Lys Leu Ser Ser Ser Leu Ala Leu
                    85                  90                  95 aag act gaa caa gat cca tcc agc aac aca gat aag gaa acc ttg gaa       336
Lys Thr Glu Gln Asp Pro Ser Ser Asn Thr Asp Lys Glu Thr Leu Glu
                100                 105                 110 aag tca gat tgc acc tca ttg agc gat aca agc aat gag aag caa ttg       384
Lys Ser Asp Cys Thr Ser Leu Ser Asp Thr Ser Asn Glu Lys Gln Leu
            115                 120                 125 tta tcc acc tgg aag aac ata ttt gtc aag aca ttt gag gat gtt gat       432
Leu Ser Thr Trp Lys Asn Ile Phe Val Lys Thr Phe Glu Asp Val Asp
130                 135                 140 gag gat ctg agg caa cat tct gga att gac tgc att tgt agt ggc aca       480
Glu Asp Leu Arg Gln His Ser Gly Ile Asp Cys Ile Cys Ser Gly Thr
145                 150                 155                 160 act gct gtc act gtc gtt agg cag ggt gat cac ctg atc att gca aat       528
Thr Ala Val Thr Val Val Arg Gln Gly Asp His Leu Ile Ile Ala Asn
                    165                 170                 175 ttg ggc gat tca cgt gcg gtt ctt tgc acc cga gac agc aag gac cgc       576
Leu Gly Asp Ser Arg Ala Val Leu Cys Thr Arg Asp Ser Lys Asp Arg
                180                 185                 190 cca att tca gtc caa cta acc act gac ctg aaa cca aat ctt cca agc       624
Pro Ile Ser Val Gln Leu Thr Thr Asp Leu Lys Pro Asn Leu Pro Ser
            195                 200                 205 gaa gct gag aga atc ctg aat tcc aag ggg cgg gtt ttc gcc atg gac       672
Glu Ala Glu Arg Ile Leu Asn Ser Lys Gly Arg Val Phe Ala Met Asp
210                 215                 220 gat gag ccg gac gtg cct agg atg tgg cta cca gac caa gac gcg ccg       720
Asp Glu Pro Asp Val Pro Arg Met Trp Leu Pro Asp Gln Asp Ala Pro
225                 230                 235                 240 ggc ctc gcc atg gca agg gca ttt gga gat ttc tgc ttg aag agt cat       768
Gly Leu Ala Met Ala Arg Ala Phe Gly Asp Phe Cys Leu Lys Ser His
                    245                 250                 255 gga cta atc tgt aca cca gaa gtc tac tac agg aag cta tct gca aaa       816
Gly Leu Ile Cys Thr Pro Glu Val Tyr Tyr Arg Lys Leu Ser Ala Lys
                260                 265                 270 gat gac ttc ttg gta ctt gct act gac ggg ata tgg gac gtg ctg tcg       864
Asp Asp Phe Leu Val Leu Ala Thr Asp Gly Ile Trp Asp Val Leu Ser
            275                 280                 285 aac aag gag gtg atc aag atc gta tcg tcg gct act gac cat tcc aag       912
Asn Lys Glu Val Ile Lys Ile Val Ser Ser Ala Thr Asp His Ser Lys
290                 295                 300 gcc gcc aag cag ctc gtc gag cgg gcg gtg cgc acg tgg cgg cgc aag       960
Ala Ala Lys Gln Leu Val Glu Arg Ala Val Arg Thr Trp Arg Arg Lys
305                 310                 315                 320 ttc ccg acg tcg atg gtc gac gac tgc gcc gtg gtg tgc ctc ttc ttg      1008
Phe Pro Thr Ser Met Val Asp Asp Cys Ala Val Val Cys Leu Phe Leu
                    325                 330                 335 aag cct tca ccg tcg tcg tcg gag agc acc ccc ggg gac gcg aaa cct      1056
Lys Pro Ser Pro Ser Ser Ser Glu Ser Thr Pro Gly Asp Ala Lys Pro
                340                 345                 350 cct cag gcc gtg tcg ttc acg ggc agc ttc cga aag gtc ctg ggc ggc      1104
Pro Gln Ala Val Ser Phe Thr Gly Ser Phe Arg Lys Val Leu Gly Gly
            355                 360                 365 ggc ggc ggc gag gcg gag gag ggg acg aat gta tgg aga gct ctg gag      1152
```

-continued

```
Gly Gly Gly Glu Ala Glu Gly Thr Asn Val Trp Arg Ala Leu Glu
    370             375                 380 ggg gtg gct cgg gtg aac tcg gtg gtg agg ctg ccg cgg atg ggc gcc    1200
Gly Val Ala Arg Val Asn Ser Val Val Arg Leu Pro Arg Met Gly Ala
385             390                 395                 400 gtg ctg agc tgg cgg cgg cgg tcg acg tcg ctg gag gaa gac gac gag    1248
Val Leu Ser Trp Arg Arg Arg Ser Thr Ser Leu Glu Glu Asp Asp Glu
                405                 410                 415 gcg agg att gat tga                                                 1263
Ala Arg Ile Asp
            420

<210> SEQ ID NO 9
<211> LENGTH: 420
<212> TYPE: PRT
<213> ORGANISM: Oryza sativa

<400> SEQUENCE: 9

Met Gly Ile Cys Cys Ser Lys Gly Lys Glu Glu Leu Glu Glu Glu Gly
1               5                   10                  15

Phe Pro Trp Lys His Asp Ala Phe Phe His Asp Gln Leu Trp Ser Ala
            20                  25                  30

Gly Val Ser Met His Thr Lys Gln Gly Trp Lys Gly Ala Asn Gln Asp
        35                  40                  45

Ala Met Thr Thr Cys Gln Asp Phe Ala Gly His Lys Gly Gln Ile Phe
    50                  55                  60

Cys Gly Val Phe Asp Gly His Gly Pro Leu Gly Arg Glu Val Ala Arg
65                  70                  75                  80

His Val Arg Asp Val Leu Pro Val Lys Leu Ser Ser Ser Leu Ala Leu
                85                  90                  95

Lys Thr Glu Gln Asp Pro Ser Ser Asn Thr Asp Lys Glu Thr Leu Glu
            100                 105                 110

Lys Ser Asp Cys Thr Ser Leu Ser Asp Thr Ser Asn Glu Lys Gln Leu
        115                 120                 125

Leu Ser Thr Trp Lys Asn Ile Phe Val Lys Thr Phe Glu Asp Val Asp
130                 135                 140

Glu Asp Leu Arg Gln His Ser Gly Ile Asp Cys Ile Cys Ser Gly Thr
145                 150                 155                 160

Thr Ala Val Thr Val Arg Gln Gly Asp His Leu Ile Ile Ala Asn
                165                 170                 175

Leu Gly Asp Ser Arg Ala Val Leu Cys Thr Arg Asp Ser Lys Asp Arg
            180                 185                 190

Pro Ile Ser Val Gln Leu Thr Thr Asp Leu Lys Pro Asn Leu Pro Ser
        195                 200                 205

Glu Ala Glu Arg Ile Leu Asn Ser Lys Gly Arg Val Phe Ala Met Asp
    210                 215                 220

Asp Glu Pro Asp Val Pro Arg Met Trp Leu Pro Asp Gln Asp Ala Pro
225                 230                 235                 240

Gly Leu Ala Met Ala Arg Ala Phe Gly Asp Phe Cys Leu Lys Ser His
                245                 250                 255

Gly Leu Ile Cys Thr Pro Glu Val Tyr Tyr Arg Lys Leu Ser Ala Lys
            260                 265                 270

Asp Asp Phe Leu Val Leu Ala Thr Asp Gly Ile Trp Asp Val Leu Ser
        275                 280                 285

Asn Lys Glu Val Ile Lys Ile Val Ser Ser Ala Thr Asp His Ser Lys
    290                 295                 300
```

```
Ala Ala Lys Gln Leu Val Glu Arg Ala Val Arg Thr Trp Arg Arg Lys
305                 310                 315                 320

Phe Pro Thr Ser Met Val Asp Asp Cys Ala Val Val Cys Leu Phe Leu
                325                 330                 335

Lys Pro Ser Pro Ser Ser Ser Glu Ser Thr Pro Gly Asp Ala Lys Pro
            340                 345                 350

Pro Gln Ala Val Ser Phe Thr Gly Ser Phe Arg Lys Val Leu Gly Gly
        355                 360                 365

Gly Gly Gly Glu Ala Glu Gly Thr Asn Val Trp Arg Ala Leu Glu
370                 375                 380

Gly Val Ala Arg Val Asn Ser Val Val Arg Leu Pro Arg Met Gly Ala
385                 390                 395                 400

Val Leu Ser Trp Arg Arg Arg Ser Thr Ser Leu Glu Glu Asp Asp Glu
                405                 410                 415

Ala Arg Ile Asp
            420

<210> SEQ ID NO 10
<211> LENGTH: 1632
<212> TYPE: DNA
<213> ORGANISM: Oryza sativa
<220> FEATURE:
<221> NAME/KEY: CDS
<222> LOCATION: (1)..(1632)

<400> SEQUENCE: 10 atg gat ggg gtg cct gat gcc caa cgc aca aca tca cca tca atg ata    48
Met Asp Gly Val Pro Asp Ala Gln Arg Thr Thr Ser Pro Ser Met Ile
1               5                   10                  15 aaa caa caa aac tac ttc aac tac ccc tac gca ttc aac tcc att cta    96
Lys Gln Gln Asn Tyr Phe Asn Tyr Pro Tyr Ala Phe Asn Ser Ile Leu
            20                  25                  30 ctc tct acc ccc tcc ttc ctt cct tcc ttc ctt cct agc tac ctc tac   144
Leu Ser Thr Pro Ser Phe Leu Pro Ser Phe Leu Pro Ser Tyr Leu Tyr
        35                  40                  45 gaa gta cca gca gca gaa gaa gca atg ggg atc tgc tgc agc aag ggg   192
Glu Val Pro Ala Ala Glu Glu Ala Met Gly Ile Cys Cys Ser Lys Gly
    50                  55                  60 aag gag gag ctt gag gag gga ttt cca tgg aag cac gac gcc ttc ttc   240
Lys Glu Glu Leu Glu Glu Gly Phe Pro Trp Lys His Asp Ala Phe Phe
65                  70                  75                  80 cac gac cag ctt tgg agc gct ggc gtc tcc atg cac acc aag caa ggc   288
His Asp Gln Leu Trp Ser Ala Gly Val Ser Met His Thr Lys Gln Gly
                85                  90                  95 tgg aag ggc gct aac cag gat gcc atg act acc tgc cag gac ttt gcg   336
Trp Lys Gly Ala Asn Gln Asp Ala Met Thr Thr Cys Gln Asp Phe Ala
            100                 105                 110 ggg cac aag ggc cag ata ttt tgt gga gtt ttt gat ggg cat ggc cct   384
Gly His Lys Gly Gln Ile Phe Cys Gly Val Phe Asp Gly His Gly Pro
        115                 120                 125 ctc gga agg gaa gtt gct cgc cat gtc cgc gac gtc ctt cca atg aaa   432
Leu Gly Arg Glu Val Ala Arg His Val Arg Asp Val Leu Pro Met Lys
    130                 135                 140 cta tcc tcc tct ttg gca ctg aaa act gaa caa gat cca tcc agc aac   480
Leu Ser Ser Ser Leu Ala Leu Lys Thr Glu Gln Asp Pro Ser Ser Asn
145                 150                 155                 160 aca gat aag gaa gcc ttg gaa aaa tca gat tgc acc tca ttg agc gat   528
Thr Asp Lys Glu Ala Leu Glu Lys Ser Asp Cys Thr Ser Leu Ser Asp
                165                 170                 175 aca agc aat gag aag caa ttg tta tcc acc tgg aag aac ata ttt gtc   576
```

```
              Thr Ser Asn Glu Lys Gln Leu Leu Ser Thr Trp Lys Asn Ile Phe Val
                          180                 185                 190 aag aca ttt gag gat gta gat gat gat ctg aga caa aat tct gga att         624
Lys Thr Phe Glu Asp Val Asp Asp Asp Leu Arg Gln Asn Ser Gly Ile
            195                 200                 205 gac tgc att tgt agt ggc aca act gct gtc act gtc gtc agg cag ggt         672
Asp Cys Ile Cys Ser Gly Thr Thr Ala Val Thr Val Val Arg Gln Gly
        210                 215                 220 gat cac ctg atc att gca aat ttg ggc gat tca cgt gcg gtt ctt tgc         720
Asp His Leu Ile Ile Ala Asn Leu Gly Asp Ser Arg Ala Val Leu Cys
225                 230                 235                 240 acc cga gat agc aag gac cgc cca att cca gtt caa cta acc act gac         768
Thr Arg Asp Ser Lys Asp Arg Pro Ile Pro Val Gln Leu Thr Thr Asp
                245                 250                 255 ctg aaa cca aat ctt cca agc gaa gct gag aga atc ctg aat tgt aag         816
Leu Lys Pro Asn Leu Pro Ser Glu Ala Glu Arg Ile Leu Asn Cys Lys
            260                 265                 270 ggg cgg gtt ttt gcc atg gac gac gag ccg gac gtg tct agg atg tgg         864
Gly Arg Val Phe Ala Met Asp Asp Glu Pro Asp Val Ser Arg Met Trp
        275                 280                 285 cta cca gac caa gac gcg ccg ggc ctc gcc atg gca agg gca ttt gga         912
Leu Pro Asp Gln Asp Ala Pro Gly Leu Ala Met Ala Arg Ala Phe Gly
290                 295                 300 gat ttc tgc ttg aag agt cat gga ctt atc tgt aca cca gaa gtc tat         960
Asp Phe Cys Leu Lys Ser His Gly Leu Ile Cys Thr Pro Glu Val Tyr
305                 310                 315                 320 tac agg aag cta tcc gaa aaa gat gaa ttc ttg gta ctt gct act gac        1008
Tyr Arg Lys Leu Ser Glu Lys Asp Glu Phe Leu Val Leu Ala Thr Asp
                325                 330                 335 ggg ata tgg gac gtg cta tcg aac aag gaa gtg atc aag atc gta tcg        1056
Gly Ile Trp Asp Val Leu Ser Asn Lys Glu Val Ile Lys Ile Val Ser
            340                 345                 350 tcg gct act gac cat tcc aag gcc gcc aag cag ctg gtc gag cgg gcg        1104
Ser Ala Thr Asp His Ser Lys Ala Ala Lys Gln Leu Val Glu Arg Ala
        355                 360                 365 gtg cgc gcg tgg cgg cgc aag ttc ccg acg tca atg gtc gac gac tgc        1152
Val Arg Ala Trp Arg Arg Lys Phe Pro Thr Ser Met Val Asp Asp Cys
370                 375                 380 gcc gtc gtc tgc ctc ttc ttg aag cct tct ccg tcg tcg gag gag agc        1200
Ala Val Val Cys Leu Phe Leu Lys Pro Ser Pro Ser Ser Glu Glu Ser
385                 390                 395                 400 acc cat gta gac gcg aag gcg cct cag gtc gtg tcg ttc acg ggc agc        1248
Thr His Val Asp Ala Lys Ala Pro Gln Val Val Ser Phe Thr Gly Ser
                405                 410                 415 ttc cgc aag gcc ctg ggt ggt ggc ggc ggc gag gcg gag gag gtg            1296
Phe Arg Lys Ala Leu Gly Gly Gly Gly Gly Glu Ala Glu Glu Val
            420                 425                 430 gaa aag att tat cga cga agt atc cgc act gtc aca cgg gac att tgg        1344
Glu Lys Ile Tyr Arg Arg Ser Ile Arg Thr Val Thr Arg Asp Ile Trp
        435                 440                 445 gac aaa gta tct gca aga ctc gac tgt gat cac ata tcc acg acg cac        1392
Asp Lys Val Ser Ala Arg Leu Asp Cys Asp His Ile Ser Thr Thr His
450                 455                 460 aac cca gat gaa acg ctg ctt gat tgg tgg gaa aga aga aca gag caa        1440
Asn Pro Asp Glu Thr Leu Leu Asp Trp Trp Glu Arg Arg Thr Glu Gln
465                 470                 475                 480 aat gac aag gac aag acg aag gga acg cgc tcc att cac atg ctc ctt        1488
Asn Asp Lys Asp Lys Thr Lys Gly Thr Arg Ser Ile His Met Leu Leu
                485                 490                 495 agc tgg gaa atc tgg tgt gaa agg aat agg cgc gtt ttc agg aat aag        1536
```

```
Ser Trp Glu Ile Trp Cys Glu Arg Asn Arg Arg Val Phe Arg Asn Lys
            500                 505                 510 gag ctc gct atc tca caa ttg gtg acc aaa atc ctt gat gaa atc aat    1584
Glu Leu Ala Ile Ser Gln Leu Val Thr Lys Ile Leu Asp Glu Ile Asn
            515                 520                 525 gtc tgg att gca tgc ggg gcg aag aat tta gcg aga ata gtg ttg taa    1632
Val Trp Ile Ala Cys Gly Ala Lys Asn Leu Ala Arg Ile Val Leu
    530                 535                 540

<210> SEQ ID NO 11
<211> LENGTH: 543
<212> TYPE: PRT
<213> ORGANISM: Oryza sativa

<400> SEQUENCE: 11

Met Asp Gly Val Pro Asp Ala Gln Arg Thr Thr Ser Pro Ser Met Ile
1               5                   10                  15

Lys Gln Gln Asn Tyr Phe Asn Tyr Pro Tyr Ala Phe Asn Ser Ile Leu
            20                  25                  30

Leu Ser Thr Pro Ser Phe Leu Pro Ser Phe Leu Pro Ser Tyr Leu Tyr
        35                  40                  45

Glu Val Pro Ala Ala Glu Glu Ala Met Gly Ile Cys Cys Ser Lys Gly
    50                  55                  60

Lys Glu Glu Leu Glu Gly Phe Pro Trp Lys His Asp Ala Phe Phe
65                  70                  75                  80

His Asp Gln Leu Trp Ser Ala Gly Val Ser Met His Thr Lys Gln Gly
                85                  90                  95

Trp Lys Gly Ala Asn Gln Asp Ala Met Thr Thr Cys Gln Asp Phe Ala
            100                 105                 110

Gly His Lys Gly Gln Ile Phe Cys Gly Val Phe Asp Gly His Gly Pro
        115                 120                 125

Leu Gly Arg Glu Val Ala Arg His Val Arg Asp Val Leu Pro Met Lys
    130                 135                 140

Leu Ser Ser Ser Leu Ala Leu Lys Thr Glu Gln Asp Pro Ser Ser Asn
145                 150                 155                 160

Thr Asp Lys Glu Ala Leu Glu Lys Ser Asp Cys Thr Ser Leu Ser Asp
                165                 170                 175

Thr Ser Asn Glu Lys Gln Leu Leu Ser Thr Trp Lys Asn Ile Phe Val
            180                 185                 190

Lys Thr Phe Glu Asp Val Asp Asp Leu Arg Gln Asn Ser Gly Ile
        195                 200                 205

Asp Cys Ile Cys Ser Gly Thr Thr Ala Val Thr Val Arg Gln Gly
    210                 215                 220

Asp His Leu Ile Ile Ala Asn Leu Gly Asp Ser Arg Ala Val Leu Cys
225                 230                 235                 240

Thr Arg Asp Ser Lys Asp Arg Pro Ile Pro Val Gln Leu Thr Thr Asp
                245                 250                 255

Leu Lys Pro Asn Leu Pro Ser Glu Ala Glu Arg Ile Leu Asn Cys Lys
            260                 265                 270

Gly Arg Val Phe Ala Met Asp Asp Glu Pro Asp Val Ser Arg Met Trp
        275                 280                 285

Leu Pro Asp Gln Asp Ala Pro Gly Leu Ala Met Ala Arg Ala Phe Gly
    290                 295                 300

Asp Phe Cys Leu Lys Ser His Gly Leu Ile Cys Thr Pro Glu Val Tyr
305                 310                 315                 320

Tyr Arg Lys Leu Ser Glu Lys Asp Glu Phe Leu Val Leu Ala Thr Asp
```

```
                    325                 330                 335
Gly Ile Trp Asp Val Leu Ser Asn Lys Glu Val Ile Lys Ile Val Ser
            340                 345                 350

Ser Ala Thr Asp His Ser Lys Ala Ala Lys Gln Leu Val Glu Arg Ala
            355                 360                 365

Val Arg Ala Trp Arg Arg Lys Phe Pro Thr Ser Met Val Asp Asp Cys
        370                 375                 380

Ala Val Val Cys Leu Phe Leu Lys Pro Ser Pro Ser Glu Glu Ser
385                 390                 395                 400

Thr His Val Asp Ala Lys Ala Pro Gln Val Val Ser Phe Thr Gly Ser
                405                 410                 415

Phe Arg Lys Ala Leu Gly Gly Gly Gly Gly Glu Ala Glu Glu Val
            420                 425                 430

Glu Lys Ile Tyr Arg Arg Ser Ile Arg Thr Val Thr Arg Asp Ile Trp
            435                 440                 445

Asp Lys Val Ser Ala Arg Leu Asp Cys Asp His Ile Ser Thr Thr His
        450                 455                 460

Asn Pro Asp Glu Thr Leu Leu Asp Trp Trp Glu Arg Arg Thr Glu Gln
465                 470                 475                 480

Asn Asp Lys Asp Lys Thr Lys Gly Thr Arg Ser Ile His Met Leu Leu
                485                 490                 495

Ser Trp Glu Ile Trp Cys Glu Arg Asn Arg Arg Val Phe Arg Asn Lys
            500                 505                 510

Glu Leu Ala Ile Ser Gln Leu Val Thr Lys Ile Leu Asp Glu Ile Asn
            515                 520                 525

Val Trp Ile Ala Cys Gly Ala Lys Asn Leu Ala Arg Ile Val Leu
        530                 535                 540

<210> SEQ ID NO 12
<211> LENGTH: 1557
<212> TYPE: DNA
<213> ORGANISM: Oryza sativa
<220> FEATURE:
<221> NAME/KEY: CDS
<222> LOCATION: (1)..(1557)

<400> SEQUENCE: 12 atg gtg gag gcc gcc gcg ggg cgc cgg tcg ggg gcc aac cgt cgg cgg      48
Met Val Glu Ala Ala Ala Gly Arg Arg Ser Gly Ala Asn Arg Arg Arg
1               5                   10                  15 cct agc ggc ggg ggc gag cgg cgg cgg cag cag cag cag cac cag cgc      96
Pro Ser Gly Gly Gly Glu Arg Arg Arg Gln Gln Gln Gln His Gln Arg
            20                  25                  30 ctc gtc gcg gtc gcg gtg gcc gcg cgc gtc gtc atg gtg gcg ccc gcg     144
Leu Val Ala Val Ala Val Ala Ala Arg Val Val Met Val Ala Pro Ala
        35                  40                  45 gcc acg ccc gcg ccc gcg gcg ggg ggt ggc ggg ggc tgc gtc gag gac     192
Ala Thr Pro Ala Pro Ala Ala Gly Gly Gly Gly Gly Cys Val Glu Asp
    50                  55                  60 atc ctc ggg tgc ctc ctc ggc gtg ctg cgc gcg ctc ggc gtc acg tgg     240
Ile Leu Gly Cys Leu Leu Gly Val Leu Arg Ala Leu Gly Val Thr Trp
65                  70                  75                  80 gcg gcg gcg gcg agg ccg cag agg cag cag ccg cgc ctg gcg gcg cag     288
Ala Ala Ala Ala Arg Pro Gln Arg Gln Gln Pro Arg Leu Ala Ala Gln
                85                  90                  95 acg ccg cga ggg ccc gcg cct ggg gcg gat ggg cgc cgc gcc gcc gcc     336
Thr Pro Arg Gly Pro Ala Pro Gly Ala Asp Gly Arg Arg Ala Ala Ala
            100                 105                 110
```

```
gag ctg agg ggg atc ccc ggc cgg atc gcg ggg aac ggg gcc tgc gcc        384
Glu Leu Arg Gly Ile Pro Gly Arg Ile Ala Gly Asn Gly Ala Cys Ala
        115                 120                 125 gtc gcg tcg ctc tac acg ctg cag ggg aag aaa ggc gtc aac caa gac        432
Val Ala Ser Leu Tyr Thr Leu Gln Gly Lys Lys Gly Val Asn Gln Asp
130                 135                 140 gcc atg atc gtc tgg gag aat ttc tgt tca aga gag gat acc att ttt        480
Ala Met Ile Val Trp Glu Asn Phe Cys Ser Arg Glu Asp Thr Ile Phe
145                 150                 155                 160 tgt ggt gtt ttt gat ggc cat gga cca aac ggc cat ttg gtt gct aag        528
Cys Gly Val Phe Asp Gly His Gly Pro Asn Gly His Leu Val Ala Lys
                165                 170                 175 agg gtg aga gat ctt ctg ccc att aag ctt ggt gcg gat ttg ggg acg        576
Arg Val Arg Asp Leu Leu Pro Ile Lys Leu Gly Ala Asp Leu Gly Thr
        180                 185                 190 gat gaa gga cga cag aca tcc act agc agc atc aaa agc aat gga gat        624
Asp Glu Gly Arg Gln Thr Ser Thr Ser Ser Ile Lys Ser Asn Gly Asp
        195                 200                 205 gaa aca gga tcc cct gga aac atg ggc aga gat gct gag cag aac gga        672
Glu Thr Gly Ser Pro Gly Asn Met Gly Arg Asp Ala Glu Gln Asn Gly
210                 215                 220 gag tac cca gag atc ttc aca gca ttg aga act tca ttt ttg agg gcg        720
Glu Tyr Pro Glu Ile Phe Thr Ala Leu Arg Thr Ser Phe Leu Arg Ala
225                 230                 235                 240 ttc aat gtc atg gat aga gat ctc aag tta cat aaa agt ata gat tgt        768
Phe Asn Val Met Asp Arg Asp Leu Lys Leu His Lys Ser Ile Asp Cys
                245                 250                 255 ttt ttc agt gga aca aca gca gtg gca gtg ctc aag cag gga cgg aat        816
Phe Phe Ser Gly Thr Thr Ala Val Ala Val Leu Lys Gln Gly Arg Asn
                260                 265                 270 ctt ata att ggt aac ctc ggg gac tcg cgg gcc atc tta ggc aca aga        864
Leu Ile Ile Gly Asn Leu Gly Asp Ser Arg Ala Ile Leu Gly Thr Arg
        275                 280                 285 gat aaa gat aat cag ctt atg gct gtc caa ttg aca gtt gat ctc aaa        912
Asp Lys Asp Asn Gln Leu Met Ala Val Gln Leu Thr Val Asp Leu Lys
        290                 295                 300 cct aac att cca agt gaa gca cag cga atc agg caa cgc agg ggc agg        960
Pro Asn Ile Pro Ser Glu Ala Gln Arg Ile Arg Gln Arg Arg Gly Arg
305                 310                 315                 320 ata ttt gca ctt cct gag gag cca gag gtt gct cgt gtt tgg ctt ccg       1008
Ile Phe Ala Leu Pro Glu Glu Pro Glu Val Ala Arg Val Trp Leu Pro
                325                 330                 335 aag tac aac tcc cct gga ctg gcc atg gct agg gca ttt gga gac ttc       1056
Lys Tyr Asn Ser Pro Gly Leu Ala Met Ala Arg Ala Phe Gly Asp Phe
                340                 345                 350 tgt ctc aag gat tat ggt cta atc tct atg cct gaa gtc tcg tac cac       1104
Cys Leu Lys Asp Tyr Gly Leu Ile Ser Met Pro Glu Val Ser Tyr His
        355                 360                 365 cgt atc aca gaa aag gat gag ttt gtt gta ttg gct act gat ggg gtt       1152
Arg Ile Thr Glu Lys Asp Glu Phe Val Val Leu Ala Thr Asp Gly Val
        370                 375                 380 tgg gat gtg ctg tca aac act gaa gtt gtt agt att gtc aac aga gct       1200
Trp Asp Val Leu Ser Asn Thr Glu Val Val Ser Ile Val Asn Arg Ala
385                 390                 395                 400 act tct cgg gcc tct gca gca cga ttg cta gtc gaa tca gct cac cgt       1248
Thr Ser Arg Ala Ser Ala Ala Arg Leu Leu Val Glu Ser Ala His Arg
                405                 410                 415 gcc tgg cgt gca cgt ttc ccc act tct aaa att gat gat tgt gct gtg       1296
Ala Trp Arg Ala Arg Phe Pro Thr Ser Lys Ile Asp Asp Cys Ala Val
                420                 425                 430
```

```
gtc tgc cta ttc ctg gat aca gac gaa tta agt gaa aca tcc agt tct   1344
Val Cys Leu Phe Leu Asp Thr Asp Glu Leu Ser Glu Thr Ser Ser Ser
        435                 440                 445 atg gcc cgc gat atg aca aat gct gta gaa gtt agc agt ggg cag cac   1392
Met Ala Arg Asp Met Thr Asn Ala Val Glu Val Ser Ser Gly Gln His
    450                 455                 460 tcc aat act atc caa ttg agc act gga gta tct tca gat gtt gtt act   1440
Ser Asn Thr Ile Gln Leu Ser Thr Gly Val Ser Ser Asp Val Val Thr
465                 470                 475                 480 gca gtt cta aca gat ggt gat gat ctg tct gct gtt gat gca gtt gca   1488
Ala Val Leu Thr Asp Gly Asp Asp Leu Ser Ala Val Asp Ala Val Ala
                485                 490                 495 aag ctg gtt act ctc acg gat ttg ccg aac aat gct tca ggc gca acg   1536
Lys Leu Val Thr Leu Thr Asp Leu Pro Asn Asn Ala Ser Gly Ala Thr
            500                 505                 510 caa agc atc acc acc aag tga                                        1557
Gln Ser Ile Thr Thr Lys
            515

<210> SEQ ID NO 13
<211> LENGTH: 518
<212> TYPE: PRT
<213> ORGANISM: Oryza sativa

<400> SEQUENCE: 13

Met Val Glu Ala Ala Ala Gly Arg Arg Ser Gly Ala Asn Arg Arg Arg
1               5                   10                  15

Pro Ser Gly Gly Gly Glu Arg Arg Arg Gln Gln Gln His Gln Arg
            20                  25                  30

Leu Val Ala Val Ala Val Ala Ala Arg Val Val Met Val Ala Pro Ala
        35                  40                  45

Ala Thr Pro Ala Pro Ala Ala Gly Gly Gly Gly Cys Val Glu Asp
    50                  55                  60

Ile Leu Gly Cys Leu Leu Gly Val Leu Arg Ala Leu Gly Val Thr Trp
65                  70                  75                  80

Ala Ala Ala Ala Arg Pro Gln Arg Gln Gln Pro Arg Leu Ala Ala Gln
                85                  90                  95

Thr Pro Arg Gly Pro Ala Pro Gly Ala Asp Gly Arg Ala Ala Ala
            100                 105                 110

Glu Leu Arg Gly Ile Pro Gly Arg Ile Ala Gly Asn Gly Ala Cys Ala
        115                 120                 125

Val Ala Ser Leu Tyr Thr Leu Gln Gly Lys Lys Gly Val Asn Gln Asp
    130                 135                 140

Ala Met Ile Val Trp Glu Asn Phe Cys Ser Arg Glu Asp Thr Ile Phe
145                 150                 155                 160

Cys Gly Val Phe Asp Gly His Gly Pro Asn Gly His Leu Val Ala Lys
                165                 170                 175

Arg Val Arg Asp Leu Leu Pro Ile Lys Leu Gly Ala Asp Leu Gly Thr
            180                 185                 190

Asp Glu Gly Arg Gln Thr Ser Thr Ser Ser Ile Lys Ser Asn Gly Asp
        195                 200                 205

Glu Thr Gly Ser Pro Gly Asn Met Gly Arg Asp Ala Glu Gln Asn Gly
    210                 215                 220

Glu Tyr Pro Glu Ile Phe Thr Ala Leu Arg Thr Ser Phe Leu Arg Ala
225                 230                 235                 240

Phe Asn Val Met Asp Arg Asp Leu Lys Leu His Lys Ser Ile Asp Cys
                245                 250                 255
```

```
Phe Phe Ser Gly Thr Thr Ala Val Ala Val Leu Lys Gln Gly Arg Asn
            260                 265                 270

Leu Ile Ile Gly Asn Leu Gly Asp Ser Arg Ala Ile Leu Gly Thr Arg
        275                 280                 285

Asp Lys Asp Asn Gln Leu Met Ala Val Gln Leu Thr Val Asp Leu Lys
    290                 295                 300

Pro Asn Ile Pro Ser Glu Ala Gln Arg Ile Arg Gln Arg Gly Arg
305                 310                 315                 320

Ile Phe Ala Leu Pro Glu Glu Pro Glu Val Ala Arg Val Trp Leu Pro
                325                 330                 335

Lys Tyr Asn Ser Pro Gly Leu Ala Met Ala Arg Ala Phe Gly Asp Phe
            340                 345                 350

Cys Leu Lys Asp Tyr Gly Leu Ile Ser Met Pro Glu Val Ser Tyr His
        355                 360                 365

Arg Ile Thr Glu Lys Asp Glu Phe Val Val Leu Ala Thr Asp Gly Val
    370                 375                 380

Trp Asp Val Leu Ser Asn Thr Glu Val Val Ser Ile Val Asn Arg Ala
385                 390                 395                 400

Thr Ser Arg Ala Ser Ala Arg Leu Leu Val Glu Ser Ala His Arg
                405                 410                 415

Ala Trp Arg Ala Arg Phe Pro Thr Ser Lys Ile Asp Asp Cys Ala Val
            420                 425                 430

Val Cys Leu Phe Leu Asp Thr Asp Glu Leu Ser Glu Thr Ser Ser Ser
        435                 440                 445

Met Ala Arg Asp Met Thr Asn Ala Val Glu Val Ser Ser Gly Gln His
    450                 455                 460

Ser Asn Thr Ile Gln Leu Ser Thr Gly Val Ser Ser Asp Val Val Thr
465                 470                 475                 480

Ala Val Leu Thr Asp Gly Asp Leu Ser Ala Val Asp Ala Val Ala
                485                 490                 495

Lys Leu Val Thr Leu Thr Asp Leu Pro Asn Asn Ala Ser Gly Ala Thr
            500                 505                 510

Gln Ser Ile Thr Thr Lys
        515

<210> SEQ ID NO 14
<211> LENGTH: 1383
<212> TYPE: DNA
<213> ORGANISM: Oryza sativa
<220> FEATURE:
<221> NAME/KEY: CDS
<222> LOCATION: (1)..(1383)

<400> SEQUENCE: 14 atg gtg gcg gtg acc ggg ggc agg ccc ccc ggc ctg cag gat gcg ccg      48
Met Val Ala Val Thr Gly Gly Arg Pro Pro Gly Leu Gln Asp Ala Pro
1               5                   10                  15 ggg gca cca cca cca gca cca gca gca gag gct gtg ccg tcg cgc ccg      96
Gly Ala Pro Pro Pro Ala Pro Ala Ala Glu Ala Val Pro Ser Arg Pro
            20                  25                  30 ctc gcg cgg gac gcg act tac gga ggc cgc gtg tac ggt ggc gta gga     144
Leu Ala Arg Asp Ala Thr Tyr Gly Gly Arg Val Tyr Gly Gly Val Gly
        35                  40                  45 gga gga gga tgc tgc ctc gag ttc ctc gac tgc gtg ctc cgg gcg atg     192
Gly Gly Gly Cys Cys Leu Glu Phe Leu Asp Cys Val Leu Arg Ala Met
    50                  55                  60 ggc gtc gcc acc ccg gcc gag atc atg ccc ccc gcg gac ttc agg tgg     240
Gly Val Ala Thr Pro Ala Glu Ile Met Pro Pro Ala Asp Phe Arg Trp
```

```
                    65                  70                  75                  80
gcc gcg cgc ccg atg cgg cgg cgc cgc ggg ggc tcc tcg tcc tcc        288
Ala Ala Arg Pro Met Arg Arg Arg Arg Gly Gly Ser Ser Ser Ser
                            85                  90                  95 tcc tcc tcg ccg cgc gac cgc gag ccg agg gac ggc cgg atc gcc gcc    336
Ser Ser Ser Pro Arg Asp Arg Glu Pro Arg Asp Gly Arg Ile Ala Ala
            100                 105                 110 aac ggc gcc tcc gct gcc gcc tcg ctc tac acg atg cgg ggc aac aag    384
Asn Gly Ala Ser Ala Ala Ala Ser Leu Tyr Thr Met Arg Gly Asn Lys
                115                 120                 125 ggc gtc aac cag gac gcc atg ctt gtc tgg gag aat ttc tgt tca aag    432
Gly Val Asn Gln Asp Ala Met Leu Val Trp Glu Asn Phe Cys Ser Lys
        130                 135                 140 gaa gat aca att ttt tgt ggt gtt ttt gat ggc cat gga cca tat ggc    480
Glu Asp Thr Ile Phe Cys Gly Val Phe Asp Gly His Gly Pro Tyr Gly
145                 150                 155                 160 cat ttg gtg tcc aag agg gtc aga gat ctc ctc cct ata aag ttg agt    528
His Leu Val Ser Lys Arg Val Arg Asp Leu Leu Pro Ile Lys Leu Ser
                    165                 170                 175 gca aat tta gga aga gat gga cac aaa gaa act tca act aac att gtc    576
Ala Asn Leu Gly Arg Asp Gly His Lys Glu Thr Ser Thr Asn Ile Val
                180                 185                 190 aca agc agc atg act gaa ggt ggt ggc acc gaa cgc atg gat aga gat    624
Thr Ser Ser Met Thr Glu Gly Gly Gly Thr Glu Arg Met Asp Arg Asp
            195                 200                 205 act gaa act ccc ctg gga acg gag gag aat gga gac tac ccc gag atg    672
Thr Glu Thr Pro Leu Gly Thr Glu Glu Asn Gly Asp Tyr Pro Glu Met
        210                 215                 220 ttt gct gca tta aga act tca tta tta agg gca ttt tat gta atg gac    720
Phe Ala Ala Leu Arg Thr Ser Leu Leu Arg Ala Phe Tyr Val Met Asp
225                 230                 235                 240 agg gat ctt aag ttt cat aaa acc att gac tct gtg ttc agt ggt act    768
Arg Asp Leu Lys Phe His Lys Thr Ile Asp Ser Val Phe Ser Gly Thr
                    245                 250                 255 aca gca gtc aca gtg atc aag cag gga cat gat ctc ctg att gga aac    816
Thr Ala Val Thr Val Ile Lys Gln Gly His Asp Leu Leu Ile Gly Asn
                260                 265                 270 ttg ggg gat tct aga gct gtc ttg gga act aga gat gaa tat gac cag    864
Leu Gly Asp Ser Arg Ala Val Leu Gly Thr Arg Asp Glu Tyr Asp Gln
            275                 280                 285 ttt ttt gct gta caa ttg aca gtt gac ctg aag cct acc att cca agt    912
Phe Phe Ala Val Gln Leu Thr Val Asp Leu Lys Pro Thr Ile Pro Ser
        290                 295                 300 gaa gct gca cga att agg gaa cga agt ggc aga ata ttc tct ctg cca    960
Glu Ala Ala Arg Ile Arg Glu Arg Ser Gly Arg Ile Phe Ser Leu Pro
305                 310                 315                 320 gat gag cca gat gtt gct cgt gtt tgg ctt ccg aag tac aac atg cca    1008
Asp Glu Pro Asp Val Ala Arg Val Trp Leu Pro Lys Tyr Asn Met Pro
                    325                 330                 335 ggg ttg gcc atg gca aga gca ttt gga gac ttt tgt cta aag gat tat    1056
Gly Leu Ala Met Ala Arg Ala Phe Gly Asp Phe Cys Leu Lys Asp Tyr
                340                 345                 350 ggt cta att tct atg cct gat gtt tcc tac cac cgc atc act gaa aag    1104
Gly Leu Ile Ser Met Pro Asp Val Ser Tyr His Arg Ile Thr Glu Lys
            355                 360                 365 gat gaa ttt gtt gtg ttg gca act gat ggg gtg tgg gat gta ctt tcc    1152
Asp Glu Phe Val Val Leu Ala Thr Asp Gly Val Trp Asp Val Leu Ser
        370                 375                 380 aac tca gaa gtt gtt agc att gtc agc caa gcc aag tca gaa gcc tca    1200
Asn Ser Glu Val Val Ser Ile Val Ser Gln Ala Lys Ser Glu Ala Ser
```

```
                                                                              1248
gcg gca cga ttt gtt gtt gaa tcg gct caa cgt gca tgg aga aca cgg
Ala Ala Arg Phe Val Val Glu Ser Ala Gln Arg Ala Trp Arg Thr Arg
            405                 410                 415

1296
ttc ccc aca tca aaa att gat gac tgc gct gtt gtc tgc ctg ttc ttg
Phe Pro Thr Ser Lys Ile Asp Asp Cys Ala Val Val Cys Leu Phe Leu
            420                 425                 430

1344
aat aca gat gct aga aat aaa ccc ccc ggt tca gga atc aaa gat ttg
Asn Thr Asp Ala Arg Asn Lys Pro Pro Gly Ser Gly Ile Lys Asp Leu
            435                 440                 445

1383
gcc aat gcc ata gaa ctg ggt ggt ggt aat ctt tct tga
Ala Asn Ala Ile Glu Leu Gly Gly Gly Asn Leu Ser
            450                 455                 460

<210> SEQ ID NO 15
<211> LENGTH: 460
<212> TYPE: PRT
<213> ORGANISM: Oryza sativa

<400> SEQUENCE: 15

Met Val Ala Val Thr Gly Gly Arg Pro Pro Gly Leu Gln Asp Ala Pro
1               5                   10                  15

Gly Ala Pro Pro Ala Pro Ala Ala Glu Ala Val Pro Ser Arg Pro
            20                  25                  30

Leu Ala Arg Asp Ala Thr Tyr Gly Gly Arg Val Tyr Gly Gly Val Gly
            35                  40                  45

Gly Gly Gly Cys Cys Leu Glu Phe Leu Asp Cys Val Leu Arg Ala Met
        50                  55                  60

Gly Val Ala Thr Pro Ala Glu Ile Met Pro Pro Ala Asp Phe Arg Trp
65              70                  75                  80

Ala Ala Arg Pro Met Arg Arg Arg Arg Gly Gly Ser Ser Ser Ser
            85                  90                  95

Ser Ser Ser Pro Arg Asp Arg Glu Pro Arg Asp Gly Arg Ile Ala Ala
            100                 105                 110

Asn Gly Ala Ser Ala Ala Ala Ser Leu Tyr Thr Met Arg Gly Asn Lys
            115                 120                 125

Gly Val Asn Gln Asp Ala Met Leu Val Trp Glu Asn Phe Cys Ser Lys
    130                 135                 140

Glu Asp Thr Ile Phe Cys Gly Val Phe Asp Gly His Gly Pro Tyr Gly
145                 150                 155                 160

His Leu Val Ser Lys Arg Val Arg Asp Leu Leu Pro Ile Lys Leu Ser
                165                 170                 175

Ala Asn Leu Gly Arg Asp Gly His Lys Glu Thr Ser Thr Asn Ile Val
            180                 185                 190

Thr Ser Ser Met Thr Glu Gly Gly Thr Glu Arg Met Asp Arg Asp
        195                 200                 205

Thr Glu Thr Pro Leu Gly Thr Glu Glu Asn Gly Asp Tyr Pro Glu Met
    210                 215                 220

Phe Ala Ala Leu Arg Thr Ser Leu Leu Arg Ala Phe Tyr Val Met Asp
225                 230                 235                 240

Arg Asp Leu Lys Phe His Lys Thr Ile Asp Ser Val Phe Ser Gly Thr
                245                 250                 255

Thr Ala Val Thr Val Ile Lys Gln Gly His Asp Leu Leu Ile Gly Asn
            260                 265                 270

Leu Gly Asp Ser Arg Ala Val Leu Gly Thr Arg Asp Glu Tyr Asp Gln
            275                 280                 285
```

```
Phe Phe Ala Val Gln Leu Thr Val Asp Leu Lys Pro Thr Ile Pro Ser
    290                 295                 300

Glu Ala Ala Arg Ile Arg Glu Arg Ser Gly Arg Ile Phe Ser Leu Pro
305                 310                 315                 320

Asp Glu Pro Asp Val Ala Arg Val Trp Leu Pro Lys Tyr Asn Met Pro
                325                 330                 335

Gly Leu Ala Met Ala Arg Ala Phe Gly Asp Phe Cys Leu Lys Asp Tyr
            340                 345                 350

Gly Leu Ile Ser Met Pro Asp Val Ser Tyr His Arg Ile Thr Glu Lys
        355                 360                 365

Asp Glu Phe Val Val Leu Ala Thr Asp Gly Val Trp Asp Val Leu Ser
    370                 375                 380

Asn Ser Glu Val Val Ser Ile Val Ser Gln Ala Lys Ser Glu Ala Ser
385                 390                 395                 400

Ala Ala Arg Phe Val Val Glu Ser Ala Gln Arg Ala Trp Arg Thr Arg
                405                 410                 415

Phe Pro Thr Ser Lys Ile Asp Asp Cys Ala Val Val Cys Leu Phe Leu
            420                 425                 430

Asn Thr Asp Ala Arg Asn Lys Pro Pro Gly Ser Gly Ile Lys Asp Leu
        435                 440                 445

Ala Asn Ala Ile Glu Leu Gly Gly Asn Leu Ser
    450                 455                 460

<210> SEQ ID NO 16
<211> LENGTH: 1299
<212> TYPE: DNA
<213> ORGANISM: Oryza sativa
<220> FEATURE:
<221> NAME/KEY: CDS
<222> LOCATION: (1)..(1299)

<400> SEQUENCE: 16 atg ggg aca tgc ctt acg acg gcg gag cag cgg gcc atg gag gtg ccg        48
Met Gly Thr Cys Leu Thr Thr Ala Glu Gln Arg Ala Met Glu Val Pro
1               5                   10                  15 gct gcg tcg gtg aag gga gga ggg ggc agg agg agt gac gag gag gcg        96
Ala Ala Ser Val Lys Gly Gly Gly Gly Arg Arg Ser Asp Glu Glu Ala
            20                  25                  30 ccc ggc agg atc gcg ggt aac ggc gcg ggg aat gtg gcc tgc ctg ttc       144
Pro Gly Arg Ile Ala Gly Asn Gly Ala Gly Asn Val Ala Cys Leu Phe
        35                  40                  45 act cgg cag ggg aag aag ggc acc aac cag gat gcc atg gtc gcg tgg       192
Thr Arg Gln Gly Lys Lys Gly Thr Asn Gln Asp Ala Met Val Ala Trp
    50                  55                  60 gag aac tat aac gga aga tca gac acg gta ttt tgt gga gtt ttt gat       240
Glu Asn Tyr Asn Gly Arg Ser Asp Thr Val Phe Cys Gly Val Phe Asp
65                  70                  75                  80 ggc cac ggt cca cat ggc cat ctc att gct agg aaa gta aga gat att       288
Gly His Gly Pro His Gly His Leu Ile Ala Arg Lys Val Arg Asp Ile
                85                  90                  95 ctc cct tcg aga ctc tgt gat ttg ata tat gaa gac tgt ggg gat agt       336
Leu Pro Ser Arg Leu Cys Asp Leu Ile Tyr Glu Asp Cys Gly Asp Ser
            100                 105                 110 cca acc agc aat tca gat gtc tca act ctg gaa gag aat tta tct ccg       384
Pro Thr Ser Asn Ser Asp Val Ser Thr Leu Glu Glu Asn Leu Ser Pro
        115                 120                 125 tat gca gat gca gag tgc aga tct ccc aca ttg gct gga caa aaa gaa       432
Tyr Ala Asp Ala Glu Cys Arg Ser Pro Thr Leu Ala Gly Gln Lys Glu
    130                 135                 140
```

| | | |
|---|---|---|
| cat caa gaa ttc ttc aac gca atg aaa gaa tct ttc aga aag gct ttt | 480 | |
| His Gln Glu Phe Phe Asn Ala Met Lys Glu Ser Phe Arg Lys Ala Phe | | |
| 145 150 155 160 | | |
| aaa aat gtg gat aag gag ctc aaa tta caa cgg aac att gat agc att | 528 | |
| Lys Asn Val Asp Lys Glu Leu Lys Leu Gln Arg Asn Ile Asp Ser Ile | | |
| 165 170 175 | | |
| tgc agt gga act act gca gtt act tta atc aag caa ggt cat gat ctt | 576 | |
| Cys Ser Gly Thr Thr Ala Val Thr Leu Ile Lys Gln Gly His Asp Leu | | |
| 180 185 190 | | |
| att gtt ggg aat cta ggt gac tct aga gct gta tta ggc acc aga gat | 624 | |
| Ile Val Gly Asn Leu Gly Asp Ser Arg Ala Val Leu Gly Thr Arg Asp | | |
| 195 200 205 | | |
| cag aac gat aag ttg gtt gct cat cag ttg act gtt gac ctg aaa cct | 672 | |
| Gln Asn Asp Lys Leu Val Ala His Gln Leu Thr Val Asp Leu Lys Pro | | |
| 210 215 220 | | |
| gat cat cca agg gag gct agg agg atc aga cgg tgt aat ggg agg gtc | 720 | |
| Asp His Pro Arg Glu Ala Arg Arg Ile Arg Arg Cys Asn Gly Arg Val | | |
| 225 230 235 240 | | |
| ttt gct cat cag gat gaa cca gat gtg gct cgc ctt tgg ctt cct aat | 768 | |
| Phe Ala His Gln Asp Glu Pro Asp Val Ala Arg Leu Trp Leu Pro Asn | | |
| 245 250 255 | | |
| tgc aac tct cct gga ctg gca atg gcc cga gct ttt ggt gac ttt tgt | 816 | |
| Cys Asn Ser Pro Gly Leu Ala Met Ala Arg Ala Phe Gly Asp Phe Cys | | |
| 260 265 270 | | |
| cta aag gat ttt ggg ttg atc tca gta cct gat gtc acc tat agg caa | 864 | |
| Leu Lys Asp Phe Gly Leu Ile Ser Val Pro Asp Val Thr Tyr Arg Gln | | |
| 275 280 285 | | |
| att act gaa aaa gac gag ttt att gtc ctg gcg aca gat ggg gtg tgg | 912 | |
| Ile Thr Glu Lys Asp Glu Phe Ile Val Leu Ala Thr Asp Gly Val Trp | | |
| 290 295 300 | | |
| gat gtt ctc tcc aac cag gaa gtg gtg gat gtt gtt gcc tca tgc tct | 960 | |
| Asp Val Leu Ser Asn Gln Glu Val Val Asp Val Val Ala Ser Cys Ser | | |
| 305 310 315 320 | | |
| ggt cgt ttc gct gca gct cgt tct gtt gtt gat tta gca aat gag act | 1008 | |
| Gly Arg Phe Ala Ala Ala Arg Ser Val Val Asp Leu Ala Asn Glu Thr | | |
| 325 330 335 | | |
| tgg agg ttc aaa tac cca acc tca aaa act gat gat tgt gca gtg gtc | 1056 | |
| Trp Arg Phe Lys Tyr Pro Thr Ser Lys Thr Asp Asp Cys Ala Val Val | | |
| 340 345 350 | | |
| tgt ctt ttc ctg aac aag tat gaa gtt acc ggt ggt tta tca ggg caa | 1104 | |
| Cys Leu Phe Leu Asn Lys Tyr Glu Val Thr Gly Gly Leu Ser Gly Gln | | |
| 355 360 365 | | |
| cct gga tat agt cca agg atg cct gcc cta tca ggt att acc cgg ccc | 1152 | |
| Pro Gly Tyr Ser Pro Arg Met Pro Ala Leu Ser Gly Ile Thr Arg Pro | | |
| 370 375 380 | | |
| aat agt aaa agg gtt act cct gac gac gtc gat gat ggt agt gac tca | 1200 | |
| Asn Ser Lys Arg Val Thr Pro Asp Asp Val Asp Asp Gly Ser Asp Ser | | |
| 385 390 395 400 | | |
| aac gta agc gga gat gag agg tcc ttg gat ggt ttc act cga ttg aac | 1248 | |
| Asn Val Ser Gly Asp Glu Arg Ser Leu Asp Gly Phe Thr Arg Leu Asn | | |
| 405 410 415 | | |
| aca ttg ttg gca cta cca aag ttt ggt gac aca agt cca act aag aaa | 1296 | |
| Thr Leu Leu Ala Leu Pro Lys Phe Gly Asp Thr Ser Pro Thr Lys Lys | | |
| 420 425 430 | | |
| tga | 1299 | |

<210> SEQ ID NO 17
<211> LENGTH: 432
<212> TYPE: PRT
<213> ORGANISM: Oryza sativa

<400> SEQUENCE: 17

```
Met Gly Thr Cys Leu Thr Thr Ala Glu Gln Arg Ala Met Glu Val Pro
1               5                   10                  15

Ala Ala Ser Val Lys Gly Gly Gly Arg Ser Asp Glu Glu Ala
            20                  25                  30

Pro Gly Arg Ile Ala Gly Asn Gly Ala Gly Asn Val Ala Cys Leu Phe
                35                  40                  45

Thr Arg Gln Gly Lys Lys Gly Thr Asn Gln Asp Ala Met Val Ala Trp
        50                  55                  60

Glu Asn Tyr Asn Gly Arg Ser Asp Thr Val Phe Cys Gly Val Phe Asp
65                  70                  75                  80

Gly His Gly Pro His Gly His Leu Ile Ala Arg Lys Val Arg Asp Ile
                85                  90                  95

Leu Pro Ser Arg Leu Cys Asp Leu Ile Tyr Glu Asp Cys Gly Asp Ser
            100                 105                 110

Pro Thr Ser Asn Ser Asp Val Ser Thr Leu Glu Asn Leu Ser Pro
        115                 120                 125

Tyr Ala Asp Ala Glu Cys Arg Ser Pro Thr Leu Ala Gly Gln Lys Glu
130                 135                 140

His Gln Glu Phe Phe Asn Ala Met Lys Glu Ser Phe Arg Lys Ala Phe
145                 150                 155                 160

Lys Asn Val Asp Lys Glu Leu Lys Leu Gln Arg Asn Ile Asp Ser Ile
                165                 170                 175

Cys Ser Gly Thr Thr Ala Val Thr Leu Ile Lys Gln Gly His Asp Leu
            180                 185                 190

Ile Val Gly Asn Leu Gly Asp Ser Arg Ala Val Leu Gly Thr Arg Asp
        195                 200                 205

Gln Asn Asp Lys Leu Val Ala His Gln Leu Thr Val Asp Leu Lys Pro
210                 215                 220

Asp His Pro Arg Glu Ala Arg Arg Ile Arg Arg Cys Asn Gly Arg Val
225                 230                 235                 240

Phe Ala His Gln Asp Glu Pro Asp Val Ala Arg Leu Trp Leu Pro Asn
                245                 250                 255

Cys Asn Ser Pro Gly Leu Ala Met Ala Arg Ala Phe Gly Asp Phe Cys
            260                 265                 270

Leu Lys Asp Phe Gly Leu Ile Ser Val Pro Asp Val Thr Tyr Arg Gln
        275                 280                 285

Ile Thr Glu Lys Asp Glu Phe Ile Val Leu Ala Thr Asp Gly Val Trp
290                 295                 300

Asp Val Leu Ser Asn Gln Glu Val Val Asp Val Ala Ser Cys Ser
305                 310                 315                 320

Gly Arg Phe Ala Ala Ala Arg Ser Val Val Asp Leu Ala Asn Glu Thr
                325                 330                 335

Trp Arg Phe Lys Tyr Pro Thr Ser Lys Thr Asp Asp Cys Ala Val Val
            340                 345                 350

Cys Leu Phe Leu Asn Lys Tyr Glu Val Thr Gly Gly Leu Ser Gly Gln
        355                 360                 365

Pro Gly Tyr Ser Pro Arg Met Pro Ala Leu Ser Gly Ile Thr Arg Pro
370                 375                 380

Asn Ser Lys Arg Val Thr Pro Asp Asp Val Asp Asp Gly Ser Asp Ser
385                 390                 395                 400

Asn Val Ser Gly Asp Glu Arg Ser Leu Asp Gly Phe Thr Arg Leu Asn
                405                 410                 415
```

```
             Thr Leu Leu Ala Leu Pro Lys Phe Gly Asp Thr Ser Pro Thr Lys Lys
                             420                 425                 430

<210> SEQ ID NO 18
<211> LENGTH: 1284
<212> TYPE: DNA
<213> ORGANISM: Oryza sativa
<220> FEATURE:
<221> NAME/KEY: CDS
<222> LOCATION: (1)..(1284)

<400> SEQUENCE: 18 atg ggg aac tgc gtg gcg agg agc ggg acg gcg gtg gat gcg ggt ggt      48
Met Gly Asn Cys Val Ala Arg Ser Gly Thr Ala Val Asp Ala Gly Gly
1               5                   10                  15 gat gga ggg gag gat ggg aag agg cgg agg agg tgg aag gcg ccg           96
Asp Gly Gly Glu Asp Gly Lys Arg Arg Arg Arg Trp Lys Ala Pro
            20                  25                  30 cgg gaa gat cag ctc ggg atg gtg ccc ggc cgg atc ttc tcc aac gac     144
Arg Glu Asp Gln Leu Gly Met Val Pro Gly Arg Ile Phe Ser Asn Asp
        35                  40                  45 ggc cgc agc cgg acg gcg acg gtg tac acg cag caa ggg cgc aag ggg     192
Gly Arg Ser Arg Thr Ala Thr Val Tyr Thr Gln Gln Gly Arg Lys Gly
50                  55                  60 atc aac cag gac gcc atg ctc gtc tgg gat ggg ttc ggc ggc gag gac     240
Ile Asn Gln Asp Ala Met Leu Val Trp Asp Gly Phe Gly Gly Glu Asp
65                  70                  75                  80 gac ggc gtg ctg tgc ggg gtg ttc gac ggg cac ggg ccg cac ggg cac     288
Asp Gly Val Leu Cys Gly Val Phe Asp Gly His Gly Pro His Gly His
                85                  90                  95 gtg gtg gcg cgg agg gtc cgc gac tcg ctg ccg ctg agg ctc atg tcc     336
Val Val Ala Arg Arg Val Arg Asp Ser Leu Pro Leu Arg Leu Met Ser
            100                 105                 110 gcg gcg cgc gac agc ggg gcg gac atg ccg gcc gcc gca tgg agg aag     384
Ala Ala Arg Asp Ser Gly Ala Asp Met Pro Ala Ala Ala Trp Arg Lys
        115                 120                 125 gcc ttc gcg cgc gcc tac aag gcc atg gac aag gac ctc cgg tcg cac     432
Ala Phe Ala Arg Ala Tyr Lys Ala Met Asp Lys Asp Leu Arg Ser His
    130                 135                 140 cct tcc ctc gat tgc ttc tgc agc gga agc act gcc gtc acc gtc ctc     480
Pro Ser Leu Asp Cys Phe Cys Ser Gly Ser Thr Ala Val Thr Val Leu
145                 150                 155                 160 aag ctc ggc tcg gat ctc tac atg gcc aac att ggg gac tcg cgc gcc     528
Lys Leu Gly Ser Asp Leu Tyr Met Ala Asn Ile Gly Asp Ser Arg Ala
                165                 170                 175 gtg ctc ggc tcc agg gag gcc acc ggc ggc ggc atg gtc gcc gtg cag     576
Val Leu Gly Ser Arg Glu Ala Thr Gly Gly Gly Met Val Ala Val Gln
            180                 185                 190 ctc acc gtt gat ctc aag ccg gat gtc ccc agc gaa gcg gag agg atc     624
Leu Thr Val Asp Leu Lys Pro Asp Val Pro Ser Glu Ala Glu Arg Ile
        195                 200                 205 aag aag tgc agg ggc agg gtg ttc gcg ctg cag gac gag ccg gag gtg     672
Lys Lys Cys Arg Gly Arg Val Phe Ala Leu Gln Asp Glu Pro Glu Val
    210                 215                 220 cca agg gtc tgg ctg ccg ttc gac gac gcg ccg ggc ctc gcg atg gcg     720
Pro Arg Val Trp Leu Pro Phe Asp Asp Ala Pro Gly Leu Ala Met Ala
225                 230                 235                 240 cga gcg ttc ggg gac ttc tgc ctg aaa gat tac ggg gtc atc tcg gtg     768
Arg Ala Phe Gly Asp Phe Cys Leu Lys Asp Tyr Gly Val Ile Ser Val
                245                 250                 255 ccg gaa ttc ttc cac tgg tct ctc aca gaa aag gac cag ttc gtc att     816
Pro Glu Phe Phe His Trp Ser Leu Thr Glu Lys Asp Gln Phe Val Ile
```

```
                        260                 265                 270
ctt gca tcg gat ggg gta tgg gat gtc ctc agc aat caa gag gct gtt        864
Leu Ala Ser Asp Gly Val Trp Asp Val Leu Ser Asn Gln Glu Ala Val
            275                 280                 285 gat ata gtg tcc gcg tcc cca agc aga tca aag gct gca aaa tcc ctt        912
Asp Ile Val Ser Ala Ser Pro Ser Arg Ser Lys Ala Ala Lys Ser Leu
290                 295                 300 gtt gag gca gcc act cgt gaa tgg aaa acc aaa tat cca aca tcc aaa        960
Val Glu Ala Ala Thr Arg Glu Trp Lys Thr Lys Tyr Pro Thr Ser Lys
305                 310                 315                 320 atc gat gat tgc gcg gtt gtt tgc tta tat ttg gat gga aaa atg gac       1008
Ile Asp Asp Cys Ala Val Val Cys Leu Tyr Leu Asp Gly Lys Met Asp
                325                 330                 335 cat gag cgt gac tca act gcc tca ttg gac aac atc agt att gaa gag       1056
His Glu Arg Asp Ser Thr Ala Ser Leu Asp Asn Ile Ser Ile Glu Glu
            340                 345                 350 ggt tca gtt gca gat cct aat gaa cct cag gag cag gag ccc acc tta       1104
Gly Ser Val Ala Asp Pro Asn Glu Pro Gln Glu Gln Glu Pro Thr Leu
        355                 360                 365 act cgg aat ttc aca gtt agg aca gtt gca ggc agc acg caa gag aag       1152
Thr Arg Asn Phe Thr Val Arg Thr Val Ala Gly Ser Thr Gln Glu Lys
370                 375                 380 acc tta gca ggg gtg gat gcg agg att gct ggt gta gcg aac gac caa       1200
Thr Leu Ala Gly Val Asp Ala Arg Ile Ala Gly Val Ala Asn Asp Gln
385                 390                 395                 400 aat tgg tca ggt ctc gat gga gtg aca cgg gta aac tca ctt gtt cag       1248
Asn Trp Ser Gly Leu Asp Gly Val Thr Arg Val Asn Ser Leu Val Gln
                405                 410                 415 ctt cct agg ttt tct gaa gag agg gca att ggc tga                       1284
Leu Pro Arg Phe Ser Glu Glu Arg Ala Ile Gly
            420                 425

<210> SEQ ID NO 19
<211> LENGTH: 427
<212> TYPE: PRT
<213> ORGANISM: Oryza sativa

<400> SEQUENCE: 19

Met Gly Asn Cys Val Ala Arg Ser Gly Thr Ala Val Asp Ala Gly Gly
1               5                   10                  15

Asp Gly Gly Glu Asp Gly Lys Arg Arg Arg Arg Trp Lys Ala Pro
            20                  25                  30

Arg Glu Asp Gln Leu Gly Met Val Pro Gly Arg Ile Phe Ser Asn Asp
        35                  40                  45

Gly Arg Ser Arg Thr Ala Thr Val Tyr Thr Gln Gln Gly Arg Lys Gly
    50                  55                  60

Ile Asn Gln Asp Ala Met Leu Val Trp Asp Gly Phe Gly Gly Glu Asp
65              70                  75                  80

Asp Gly Val Leu Cys Gly Val Phe Asp Gly His Gly Pro His Gly His
                85                  90                  95

Val Val Ala Arg Arg Val Arg Asp Ser Leu Pro Leu Arg Leu Met Ser
            100                 105                 110

Ala Ala Arg Asp Ser Gly Ala Asp Met Pro Ala Ala Trp Arg Lys
        115                 120                 125

Ala Phe Ala Arg Ala Tyr Lys Ala Met Asp Lys Asp Leu Arg Ser His
    130                 135                 140

Pro Ser Leu Asp Cys Phe Cys Ser Gly Ser Thr Ala Val Thr Val Leu
145                 150                 155                 160
```

```
Lys Leu Gly Ser Asp Leu Tyr Met Ala Asn Ile Gly Asp Ser Arg Ala
            165                 170                 175

Val Leu Gly Ser Arg Glu Ala Thr Gly Gly Met Val Ala Val Gln
        180                 185                 190

Leu Thr Val Asp Leu Lys Pro Asp Val Pro Ser Glu Ala Glu Arg Ile
        195                 200                 205

Lys Lys Cys Arg Gly Arg Val Phe Ala Leu Gln Asp Glu Pro Glu Val
    210                 215                 220

Pro Arg Val Trp Leu Pro Phe Asp Ala Pro Gly Leu Ala Met Ala
225                 230                 235                 240

Arg Ala Phe Gly Asp Phe Cys Leu Lys Asp Tyr Gly Val Ile Ser Val
                245                 250                 255

Pro Glu Phe Phe His Trp Ser Leu Thr Glu Lys Asp Gln Phe Val Ile
            260                 265                 270

Leu Ala Ser Asp Gly Val Trp Asp Val Leu Ser Asn Gln Glu Ala Val
        275                 280                 285

Asp Ile Val Ser Ala Ser Pro Ser Arg Ser Lys Ala Ala Lys Ser Leu
    290                 295                 300

Val Glu Ala Ala Thr Arg Glu Trp Lys Thr Lys Tyr Pro Thr Ser Lys
305                 310                 315                 320

Ile Asp Asp Cys Ala Val Val Cys Leu Tyr Leu Asp Gly Lys Met Asp
                325                 330                 335

His Glu Arg Asp Ser Thr Ala Ser Leu Asp Asn Ile Ser Ile Glu Glu
            340                 345                 350

Gly Ser Val Ala Asp Pro Asn Glu Pro Gln Glu Gln Pro Thr Leu
        355                 360                 365

Thr Arg Asn Phe Thr Val Arg Thr Val Ala Gly Ser Thr Gln Glu Lys
370                 375                 380

Thr Leu Ala Gly Val Asp Ala Arg Ile Ala Gly Val Ala Asn Asp Gln
385                 390                 395                 400

Asn Trp Ser Gly Leu Asp Gly Val Thr Arg Val Asn Ser Leu Val Gln
                405                 410                 415

Leu Pro Arg Phe Ser Glu Glu Arg Ala Ile Gly
            420                 425

<210> SEQ ID NO 20
<211> LENGTH: 1596
<212> TYPE: DNA
<213> ORGANISM: Oryza sativa
<220> FEATURE:
<221> NAME/KEY: CDS
<222> LOCATION: (1)..(1596)

<400> SEQUENCE: 20 atg ggc tcc tgc ctc tcc tcc gac ctg cct ccc cgc gcc ggc gcc ggc    48
Met Gly Ser Cys Leu Ser Ser Asp Leu Pro Pro Arg Ala Gly Ala Gly
1               5                   10                  15 gcg gga gcg tca ccc ggg tgg ccg cag cgg tgg cgg agg agg agg cag    96
Ala Gly Ala Ser Pro Gly Trp Pro Gln Arg Trp Arg Arg Arg Arg Gln
            20                  25                  30 cgg ggg gtg gag cgg ggc ggg gct gtt tcc ggc ggc ggc ggc ggc gtc   144
Arg Gly Val Glu Arg Gly Gly Ala Val Ser Gly Gly Gly Gly Gly Val
        35                  40                  45 ttc tcc atc ggc gtc ggc ggc aag aag ctg cac cac ggc ggc gga gga   192
Phe Ser Ile Gly Val Gly Gly Lys Lys Leu His His Gly Gly Gly Gly
    50                  55                  60 gga ggg gag atg acg gag gag gag ctc gcg aag gtc gag ggg agg gtg   240
Gly Gly Glu Met Thr Glu Glu Glu Leu Ala Lys Val Glu Gly Arg Val
```

```
                 65                 70                  75                  80
tgc gtc aac ggc gcg agc gcg gcg gcg tgc ctg cac acg cag cag ggg      288
Cys Val Asn Gly Ala Ser Ala Ala Ala Cys Leu His Thr Gln Gln Gly
                     85                  90                  95 cgg aag ggc acc aac cag gac gcc atg gtc gtg tgg gag aac ttt aat      336
Arg Lys Gly Thr Asn Gln Asp Ala Met Val Val Trp Glu Asn Phe Asn
                100                 105                 110 aca agt gat agt gtc ttc tgt ggt gtg ttt gat ggt cat ggt cca tat      384
Thr Ser Asp Ser Val Phe Cys Gly Val Phe Asp Gly His Gly Pro Tyr
            115                 120                 125 ggt cat ttt gtt gcc aag aag gtc aga gat tct ctt cct gtc aaa ata      432
Gly His Phe Val Ala Lys Lys Val Arg Asp Ser Leu Pro Val Lys Ile
        130                 135                 140 cgc aca cta tgg aaa acc agt gcc aac gag gac act agt tcc cac caa      480
Arg Thr Leu Trp Lys Thr Ser Ala Asn Glu Asp Thr Ser Ser His Gln
145                 150                 155                 160 aat gga agc att tct gga agt gtt aat tca gaa gag tca cct gtt gtt      528
Asn Gly Ser Ile Ser Gly Ser Val Asn Ser Glu Glu Ser Pro Val Val
                    165                 170                 175 gat gat gaa tgg ggt gaa tat gct gat gac agc gag aag ctt cct gag      576
Asp Asp Glu Trp Gly Glu Tyr Ala Asp Asp Ser Glu Lys Leu Pro Glu
                180                 185                 190 atg ttt ctt cca ctt aag cag tct tat ttt aag gct ttc aaa ttg atg      624
Met Phe Leu Pro Leu Lys Gln Ser Tyr Phe Lys Ala Phe Lys Leu Met
            195                 200                 205 gac aag gaa ctc aaa atg cac cct aca gtt gat tgc ttt tgc agt gga      672
Asp Lys Glu Leu Lys Met His Pro Thr Val Asp Cys Phe Cys Ser Gly
        210                 215                 220 tca aca gca gtc acg tta gta aaa cag gga ttg gat ctt gtg gtt ggg      720
Ser Thr Ala Val Thr Leu Val Lys Gln Gly Leu Asp Leu Val Val Gly
225                 230                 235                 240 aac ctt ggg gac tcg aga gca ata atg ggg aca cga gat gct gcc aat      768
Asn Leu Gly Asp Ser Arg Ala Ile Met Gly Thr Arg Asp Ala Ala Asn
                    245                 250                 255 aat cta act gct gta caa ctc aca gtt gat ttg aag cct aac ctt cca      816
Asn Leu Thr Ala Val Gln Leu Thr Val Asp Leu Lys Pro Asn Leu Pro
                260                 265                 270 agg gaa gct gcg agg atc cag cag tgt agg gga aga gtt ttt gct ctt      864
Arg Glu Ala Ala Arg Ile Gln Gln Cys Arg Gly Arg Val Phe Ala Leu
            275                 280                 285 cag gat gaa cca gaa gtt gcc aga gta tgg ttg cca aat aat gac tct      912
Gln Asp Glu Pro Glu Val Ala Arg Val Trp Leu Pro Asn Asn Asp Ser
        290                 295                 300 cct gga ttg gca atg gca aga gct ttt gga gac ttc tgc ctt aaa gat      960
Pro Gly Leu Ala Met Ala Arg Ala Phe Gly Asp Phe Cys Leu Lys Asp
305                 310                 315                 320 tat ggt tta ata tct gtt cca cag ata tcc tat cgt cgt ctt act gaa     1008
Tyr Gly Leu Ile Ser Val Pro Gln Ile Ser Tyr Arg Arg Leu Thr Glu
                    325                 330                 335 aag gat gag ttc ata ata ctg gcc act gat ggg gtt tgg gac gtc ctc     1056
Lys Asp Glu Phe Ile Ile Leu Ala Thr Asp Gly Val Trp Asp Val Leu
                340                 345                 350 tca aac aag gag gct gtt gac ata gta gcc gca gct cca tct cgt gca     1104
Ser Asn Lys Glu Ala Val Asp Ile Val Ala Ala Ala Pro Ser Arg Ala
            355                 360                 365 acg gct gcc agg gct ctt gtc gac tgt gct gtc aga tca tgg aga ttg     1152
Thr Ala Ala Arg Ala Leu Val Asp Cys Ala Val Arg Ser Trp Arg Leu
        370                 375                 380 aag ttc cca aca tcc aag agc gat gac tgc gct gtt gtg tgc cta ttc     1200
Lys Phe Pro Thr Ser Lys Ser Asp Asp Cys Ala Val Val Cys Leu Phe
```

```
                385                 390                 395                 400
tta gac cat gca aag tca cct gac ttg att caa gag aac gag agc gag          1248
Leu Asp His Ala Lys Ser Pro Asp Leu Ile Gln Glu Asn Glu Ser Glu
                405                 410                 415 gaa gaa act aca gag gat gtt gca atc cca gac acc gtt gct aag gtt          1296
Glu Glu Thr Thr Glu Asp Val Ala Ile Pro Asp Thr Val Ala Lys Val
        420                 425                 430 gac caa gac att gca caa gga gat gca cat atc tcc agt gaa gag caa          1344
Asp Gln Asp Ile Ala Gln Gly Asp Ala His Ile Ser Ser Glu Glu Gln
    435                 440                 445 atc acc gag cca gca ttg cag cac tcc tac aca tta agg gat gtt gat          1392
Ile Thr Glu Pro Ala Leu Gln His Ser Tyr Thr Leu Arg Asp Val Asp
450                 455                 460 gag att gta ccg gta gag gag cct cca gtc tca aag gaa cct gaa aga          1440
Glu Ile Val Pro Val Glu Glu Pro Pro Val Ser Lys Glu Pro Glu Arg
465                 470                 475                 480 tgt gga tct gcc cgc agc ctt gct gat tgt ata tcc aca aac gag gag          1488
Cys Gly Ser Ala Arg Ser Leu Ala Asp Cys Ile Ser Thr Asn Glu Glu
                485                 490                 495 gag gaa tgg tca gca ctc gaa ggt gtg acg cgg gtc aat tcc ctc ttg          1536
Glu Glu Trp Ser Ala Leu Glu Gly Val Thr Arg Val Asn Ser Leu Leu
        500                 505                 510 aac ctt ccc aga ata ctt tca ggc gag aag aga tca acc agc tgg agg          1584
Asn Leu Pro Arg Ile Leu Ser Gly Glu Lys Arg Ser Thr Ser Trp Arg
    515                 520                 525 aag cgg cga tga                                                          1596
Lys Arg Arg
    530

<210> SEQ ID NO 21
<211> LENGTH: 531
<212> TYPE: PRT
<213> ORGANISM: Oryza sativa

<400> SEQUENCE: 21

Met Gly Ser Cys Leu Ser Ser Asp Leu Pro Pro Arg Ala Gly Ala Gly
1               5                   10                  15

Ala Gly Ala Ser Pro Gly Trp Pro Gln Arg Trp Arg Arg Arg Gln
            20                  25                  30

Arg Gly Val Glu Arg Gly Ala Val Ser Gly Gly Gly Gly Val
        35                  40                  45

Phe Ser Ile Gly Val Gly Lys Lys Leu His Gly Gly Gly
    50                  55                  60

Gly Gly Glu Met Thr Glu Glu Leu Ala Lys Val Glu Gly Arg Val
65                  70                  75                  80

Cys Val Asn Gly Ala Ser Ala Ala Cys Leu His Thr Gln Gln Gly
                85                  90                  95

Arg Lys Gly Thr Asn Gln Asp Ala Met Val Val Trp Glu Asn Phe Asn
            100                 105                 110

Thr Ser Asp Ser Val Phe Cys Gly Val Phe Asp Gly His Gly Pro Tyr
        115                 120                 125

Gly His Phe Val Ala Lys Lys Val Arg Asp Ser Leu Pro Val Lys Ile
    130                 135                 140

Arg Thr Leu Trp Lys Thr Ser Ala Asn Glu Asp Thr Ser Ser His Gln
145                 150                 155                 160

Asn Gly Ser Ile Ser Gly Ser Val Asn Ser Glu Glu Ser Pro Val Val
                165                 170                 175

Asp Asp Glu Trp Gly Glu Tyr Ala Asp Asp Ser Glu Lys Leu Pro Glu
```

```
                    180                 185                 190
Met Phe Leu Pro Leu Lys Gln Ser Tyr Phe Lys Ala Phe Lys Leu Met
            195                 200                 205

Asp Lys Glu Leu Lys Met His Pro Thr Val Asp Cys Phe Cys Ser Gly
        210                 215                 220

Ser Thr Ala Val Thr Leu Val Lys Gln Gly Leu Asp Leu Val Val Gly
225                 230                 235                 240

Asn Leu Gly Asp Ser Arg Ala Ile Met Gly Thr Arg Asp Ala Ala Asn
                245                 250                 255

Asn Leu Thr Ala Val Gln Leu Thr Val Asp Leu Lys Pro Asn Leu Pro
            260                 265                 270

Arg Glu Ala Ala Arg Ile Gln Gln Cys Arg Gly Arg Val Phe Ala Leu
        275                 280                 285

Gln Asp Glu Pro Glu Val Ala Arg Val Trp Leu Pro Asn Asn Asp Ser
        290                 295                 300

Pro Gly Leu Ala Met Ala Arg Ala Phe Gly Asp Phe Cys Leu Lys Asp
305                 310                 315                 320

Tyr Gly Leu Ile Ser Val Pro Gln Ile Ser Tyr Arg Arg Leu Thr Glu
                325                 330                 335

Lys Asp Glu Phe Ile Ile Leu Ala Thr Asp Gly Val Trp Asp Val Leu
            340                 345                 350

Ser Asn Lys Glu Ala Val Asp Ile Val Ala Ala Pro Ser Arg Ala
                355                 360                 365

Thr Ala Arg Ala Leu Val Asp Cys Ala Val Arg Ser Trp Arg Leu
        370                 375                 380

Lys Phe Pro Thr Ser Lys Ser Asp Asp Cys Ala Val Val Cys Leu Phe
385                 390                 395                 400

Leu Asp His Ala Lys Ser Pro Asp Leu Ile Gln Glu Asn Glu Ser Glu
                405                 410                 415

Glu Glu Thr Thr Glu Asp Val Ala Ile Pro Asp Thr Val Ala Lys Val
            420                 425                 430

Asp Gln Asp Ile Ala Gln Gly Asp Ala His Ile Ser Ser Glu Glu Gln
        435                 440                 445

Ile Thr Glu Pro Ala Leu Gln His Ser Tyr Thr Leu Arg Asp Val Asp
        450                 455                 460

Glu Ile Val Pro Val Glu Pro Pro Val Ser Lys Glu Pro Glu Arg
465                 470                 475                 480

Cys Gly Ser Ala Arg Ser Leu Ala Asp Cys Ile Ser Thr Asn Glu Glu
                485                 490                 495

Glu Glu Trp Ser Ala Leu Glu Gly Val Thr Arg Val Asn Ser Leu Leu
            500                 505                 510

Asn Leu Pro Arg Ile Leu Ser Gly Glu Lys Arg Ser Thr Ser Trp Arg
        515                 520                 525

Lys Arg Arg
        530

<210> SEQ ID NO 22
<211> LENGTH: 1170
<212> TYPE: DNA
<213> ORGANISM: Oryza sativa
<220> FEATURE:
<221> NAME/KEY: CDS
<222> LOCATION: (1)..(1170)

<400> SEQUENCE: 22 atg ggg atc tgt gca tct tca gag cag ctg gag cat gtt cat gag aca          48
```

```
                Met Gly Ile Cys Ala Ser Ser Glu Gln Leu Glu His Val His Glu Thr
                 1               5                  10                  15 gat gag agc att gtg tat gtg aag gat gag caa gga agg ggg ggt agg           96
Asp Glu Ser Ile Val Tyr Val Lys Asp Glu Gln Gly Arg Gly Gly Arg
                 20                  25                  30 ggg gtg gag agt ggg ggg gct agg aag gtg gcc tcc ctc ttc tcc cag          144
Gly Val Glu Ser Gly Gly Ala Arg Lys Val Ala Ser Leu Phe Ser Gln
         35                  40                  45 agg ggc aag aaa ggc ccc aac cag gac tct gtc atc ctc tgc cag gga          192
Arg Gly Lys Lys Gly Pro Asn Gln Asp Ser Val Ile Leu Cys Gln Gly
         50                  55                  60 ttc ggc atg gag gac ggc gtg ttc tgc ggc gtg ttc gac ggc cat ggc          240
Phe Gly Met Glu Asp Gly Val Phe Cys Gly Val Phe Asp Gly His Gly
 65              70                  75                  80 cgg tgc ggg caa ttc atc agc aag ctg gtg cgg gac tac ctc ccg ttc          288
Arg Cys Gly Gln Phe Ile Ser Lys Leu Val Arg Asp Tyr Leu Pro Phe
                 85                  90                  95 atg atc ctg agc cac cgg aac gcg ctc ctc ctg gcc gac gcc gcc gcc          336
Met Ile Leu Ser His Arg Asn Ala Leu Leu Leu Ala Asp Ala Ala Ala
                100                 105                 110 gac gac gac gac gac gcc gcg ttc agc gac gac gcg gcg gcg tcg tcg          384
Asp Asp Asp Asp Asp Ala Ala Phe Ser Asp Asp Ala Ala Ala Ser Ser
            115                 120                 125 tcc gcg gac agc agc ggc aac tcg tcg ccg cag ccg tcg gcg tcg gcg          432
Ser Ala Asp Ser Ser Gly Asn Ser Ser Pro Gln Pro Ser Ala Ser Ala
    130                 135                 140 tcg gcg cag atg ctg gag gag tgg agg cag gcg tgc gcc agc gcg ttc          480
Ser Ala Gln Met Leu Glu Glu Trp Arg Gln Ala Cys Ala Ser Ala Phe
145                 150                 155                 160 gcc gcc atg gac ggc gag ctc aag ctc cag ccg aac ctc gac tgc gcg          528
Ala Ala Met Asp Gly Glu Leu Lys Leu Gln Pro Asn Leu Asp Cys Ala
                165                 170                 175 ttc agc ggc acg acg gcg gtg tgc gcc atc aag cag ggc agg gac ctc          576
Phe Ser Gly Thr Thr Ala Val Cys Ala Ile Lys Gln Gly Arg Asp Leu
                180                 185                 190 atc atc gcc aac ctc ggc gac tcg agg gcg gtg ctc gcc acc atg tcg          624
Ile Ile Ala Asn Leu Gly Asp Ser Arg Ala Val Leu Ala Thr Met Ser
            195                 200                 205 gac acc ggc tac ctc cag gcg gtg cag ctg acg gtg gac cac aag ccg          672
Asp Thr Gly Tyr Leu Gln Ala Val Gln Leu Thr Val Asp His Lys Pro
    210                 215                 220 agc gtg ccg gag gag gcg gcg agg atc aag cgg agc ggg ggg agg gtg          720
Ser Val Pro Glu Glu Ala Ala Arg Ile Lys Arg Ser Gly Gly Arg Val
225                 230                 235                 240 ttc ggg ctg aag gac gag ccg ggg gtg atg cgg gtg tgg ctc ccc ggc          768
Phe Gly Leu Lys Asp Glu Pro Gly Val Met Arg Val Trp Leu Pro Gly
                245                 250                 255 gag aac tcg ccg ggg ctc gcc atg gcg agg tcg ctg ggc gac atg agg          816
Glu Asn Ser Pro Gly Leu Ala Met Ala Arg Ser Leu Gly Asp Met Arg
                260                 265                 270 ctg aag cgg cac ggc gtg atc ccg gcg ccg gag gtg acg tcg cgg cgc          864
Leu Lys Arg His Gly Val Ile Pro Ala Pro Glu Val Thr Ser Arg Arg
            275                 280                 285 gtg acg ggc gcc gac ctg ttc atg gtg ctc gcc acg gac ggg gtg tgg          912
Val Thr Gly Ala Asp Leu Phe Met Val Leu Ala Thr Asp Gly Val Trp
    290                 295                 300 gac gtg ctg agc aac gag gag gtg gtg tcc atc gtg tgc gcg acg ccg          960
Asp Val Leu Ser Asn Glu Glu Val Val Ser Ile Val Cys Ala Thr Pro
305                 310                 315                 320 cgg aag cag cac gcg tcg aag gcg gtg gtg gag gcc gcc gtg cag cgg         1008
```

```
Arg Lys Gln His Ala Ser Lys Ala Val Val Glu Ala Val Gln Arg
                325                 330                 335 tgg cgg gcc aag ttc ccg acg tcc agg gtg gac gac tgc tcc gcc gtc      1056
Trp Arg Ala Lys Phe Pro Thr Ser Arg Val Asp Asp Cys Ser Ala Val
            340                 345                 350 tgc ctc ttc ctc cac gac cac acc ctc ggc acg gcc gcc gcc gcc tcc      1104
Cys Leu Phe Leu His Asp His Thr Leu Gly Thr Ala Ala Ala Ala Ser
        355                 360                 365 gcc gca gcc gcc gcg gcc gcc aga aag gcg cgc agg gcc tcc acc gcc      1152
Ala Ala Ala Ala Ala Ala Ala Arg Lys Ala Arg Arg Ala Ser Thr Ala
370                 375                 380 acg ccg ccg gcg agc tga                                               1170
Thr Pro Pro Ala Ser
385

<210> SEQ ID NO 23
<211> LENGTH: 389
<212> TYPE: PRT
<213> ORGANISM: Oryza sativa

<400> SEQUENCE: 23

Met Gly Ile Cys Ala Ser Ser Glu Gln Leu Glu His Val His Glu Thr
1               5                   10                  15

Asp Glu Ser Ile Val Tyr Val Lys Asp Glu Gln Gly Arg Gly Gly Arg
            20                  25                  30

Gly Val Glu Ser Gly Gly Ala Arg Lys Val Ala Ser Leu Phe Ser Gln
        35                  40                  45

Arg Gly Lys Lys Gly Pro Asn Gln Asp Ser Val Ile Leu Cys Gln Gly
    50                  55                  60

Phe Gly Met Glu Asp Gly Val Phe Cys Gly Val Phe Asp Gly His Gly
65                  70                  75                  80

Arg Cys Gly Gln Phe Ile Ser Lys Leu Val Arg Asp Tyr Leu Pro Phe
                85                  90                  95

Met Ile Leu Ser His Arg Asn Ala Leu Leu Leu Ala Asp Ala Ala Ala
            100                 105                 110

Asp Asp Asp Asp Ala Ala Phe Ser Asp Ala Ala Ala Ser Ser
        115                 120                 125

Ser Ala Asp Ser Ser Gly Asn Ser Ser Pro Gln Pro Ser Ala Ser Ala
    130                 135                 140

Ser Ala Gln Met Leu Glu Glu Trp Arg Gln Ala Cys Ala Ser Ala Phe
145                 150                 155                 160

Ala Ala Met Asp Gly Glu Leu Lys Leu Gln Pro Asn Leu Asp Cys Ala
                165                 170                 175

Phe Ser Gly Thr Thr Ala Val Cys Ala Ile Lys Gln Gly Arg Asp Leu
            180                 185                 190

Ile Ile Ala Asn Leu Gly Asp Ser Arg Ala Val Leu Ala Thr Met Ser
        195                 200                 205

Asp Thr Gly Tyr Leu Gln Ala Val Gln Leu Thr Val Asp His Lys Pro
    210                 215                 220

Ser Val Pro Glu Glu Ala Ala Arg Ile Lys Arg Ser Gly Gly Arg Val
225                 230                 235                 240

Phe Gly Leu Lys Asp Glu Pro Gly Val Met Arg Val Trp Leu Pro Gly
                245                 250                 255

Glu Asn Ser Pro Gly Leu Ala Met Ala Arg Ser Leu Gly Asp Met Arg
            260                 265                 270

Leu Lys Arg His Gly Val Ile Pro Ala Pro Glu Val Thr Ser Arg Arg
        275                 280                 285
```

-continued

```
Val Thr Gly Ala Asp Leu Phe Met Val Leu Ala Thr Asp Gly Val Trp
    290                 295                 300

Asp Val Leu Ser Asn Glu Glu Val Val Ser Ile Val Cys Ala Thr Pro
305                 310                 315                 320

Arg Lys Gln His Ala Ser Lys Ala Val Val Glu Ala Ala Val Gln Arg
                325                 330                 335

Trp Arg Ala Lys Phe Pro Thr Ser Arg Val Asp Asp Cys Ser Ala Val
            340                 345                 350

Cys Leu Phe Leu His Asp His Thr Leu Gly Thr Ala Ala Ala Ala Ser
        355                 360                 365

Ala Ala Ala Ala Ala Ala Arg Lys Ala Arg Arg Ala Ser Thr Ala
    370                 375                 380

Thr Pro Pro Ala Ser
385

<210> SEQ ID NO 24
<211> LENGTH: 25
<212> TYPE: DNA
<213> ORGANISM: Artificial
<220> FEATURE:
<223> OTHER INFORMATION: Synthetic DNA

<400> SEQUENCE: 24
tgctttcgcc attaaatagc gacgg                                           25

<210> SEQ ID NO 25
<211> LENGTH: 23
<212> TYPE: DNA
<213> ORGANISM: Artificial
<220> FEATURE:
<223> OTHER INFORMATION: Synthetic DNA

<400> SEQUENCE: 25
cgctgcggac atctacattt ttg                                             23

<210> SEQ ID NO 26
<211> LENGTH: 22
<212> TYPE: DNA
<213> ORGANISM: Artificial
<220> FEATURE:
<223> OTHER INFORMATION: Synthetic DNA

<400> SEQUENCE: 26
tcccggacat gaagccattt ac                                              22

<210> SEQ ID NO 27
<211> LENGTH: 16
<212> TYPE: DNA
<213> ORGANISM: Artificial
<220> FEATURE:
<223> OTHER INFORMATION: Synthetic DNA
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 27
ngtcgaswga nawgaa                                                     16

<210> SEQ ID NO 28
```

```
<211> LENGTH: 498
<212> TYPE: DNA
<213> ORGANISM: Arabidopsis thaliana
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t

<400> SEQUENCE: 28
taaccttacg ctttgctcgg tcccagacgc aagattacat ctctttctat ggnttgagat      60
cgnacggacg gctgtttgag gacggtccaa ttgccactag ccagatttac gtgcatagca    120
agttaatgat tgttgatgac cggatcgcag tgatcggatc ttctaatata aacgatagga    180
gcttactagg ttcacgagac tctgaggtac tttcaaaaat ccaattcatt ctttattgca    240
gcaaaacaga gttatgtatt catttgaatc aatcatgttt cagatcggtg ttgtgattga    300
agacaaagaa ttcgtggaat cttcgatgaa cggaatgaag tggatggccg ggaagttctc    360
ttacagtctt agatgttcct tgtggtcaga gcatctcggc cttcacgccg gagaggtaat    420
tttaaaaaat ttctagaaac gcctactact atacattttt gacttcagaa acctttattt    480
tcatctcact cgaccaaa                                                  498

<210> SEQ ID NO 29
<211> LENGTH: 39
<212> TYPE: DNA
<213> ORGANISM: Artificial
<220> FEATURE:
<223> OTHER INFORMATION: Synthetic DNA

<400> SEQUENCE: 29
acgcgtcgac atgggacatt tctcttccat gttcaacgg                             39

<210> SEQ ID NO 30
<211> LENGTH: 43
<212> TYPE: DNA
<213> ORGANISM: Artificial
<220> FEATURE:
<223> OTHER INFORMATION: Synthetic DNA

<400> SEQUENCE: 30
tgtacatgta cactatagag atggcgacga cgatgaagaa tgg                        43

<210> SEQ ID NO 31
<211> LENGTH: 19
<212> TYPE: PRT
<213> ORGANISM: Artificial
<220> FEATURE:
<223> OTHER INFORMATION: A consensus sequence in a protein phosphatase
<220> FEATURE:
<221> NAME/KEY: misc_feature
<222> LOCATION: (1)..(1)
<223> OTHER INFORMATION: Xaa can be any naturally occurring amino acid,
      or preferably L or F
<220> FEATURE:
<221> NAME/KEY: misc_feature
<222> LOCATION: (4)..(4)
<223> OTHER INFORMATION: Xaa can be any naturally occurring amino acid,
      or preferably V, I or M
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(14)
```

```
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid,
      or preferably V or I
<220> FEATURE:
<221> NAME/KEY: misc_feature
<222> LOCATION: (16)..(16)
<223> OTHER INFORMATION: Xaa can be any naturally occurring amino acid,
      or preferably S or A
<220> FEATURE:
<221> NAME/KEY: misc_feature
<222> LOCATION: (17)..(17)
<223> OTHER INFORMATION: Xaa can be any naturally occurring amino acid,
      or preferably K or R
<220> FEATURE:
<221> NAME/KEY: misc_feature
<222> LOCATION: (18)..(18)
<223> OTHER INFORMATION: Xaa can be any naturally occurring amino acid

<400> SEQUENCE: 31

Xaa Cys Gly Xaa Phe Asp Gly His Gly Xaa Xaa Gly Xaa Xaa Xaa Xaa
1               5                   10                  15

Xaa Xaa Val

<210> SEQ ID NO 32
<211> LENGTH: 27
<212> TYPE: PRT
<213> ORGANISM: Artificial
<220> FEATURE:
<223> OTHER INFORMATION: A consensus sequence in a protein phosphatase
<220> FEATURE:
<221> NAME/KEY: misc_feature
<222> LOCATION: (3)..(3)
<223> OTHER INFORMATION: Xaa can be any naturally occurring amino acid,
      or preferably T, C or S
<220> FEATURE:
<221> NAME/KEY: misc_feature
<222> LOCATION: (5)..(5)
<223> OTHER INFORMATION: Xaa can be any naturally occurring amino acid,
      or preferably G, A or S
<220> FEATURE:
<221> NAME/KEY: misc_feature
<222> LOCATION: (6)..(6)
<223> OTHER INFORMATION: Xaa can be any naturally occurring amino acid,
      or preferably V or L
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid,
      or preferably I, V, F or L
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid,
      or preferably G or A
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid,
      or preferably L, V or I
<220> FEATURE:
<221> NAME/KEY: misc_feature
<222> LOCATION: (16)..(16)
```

```
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid,
      or preferably I, V or M
<220> FEATURE:
<221> NAME/KEY: misc_feature
<222> LOCATION: (18)..(18)
<223> OTHER INFORMATION: Xaa can be any naturally occurring amino acid,
      or preferably A or G
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid,
      or preferably D or H
<220> FEATURE:
<221> NAME/KEY: misc_feature
<222> LOCATION: (26)..(26)
<223> OTHER INFORMATION: Xaa can be any naturally occurring amino acid,
      or preferably V or I
<220> FEATURE:
<221> NAME/KEY: misc_feature
<222> LOCATION: (27)..(27)
<223> OTHER INFORMATION: Xaa can be any naturally occurring amino acid,
      or preferably L, M or I

<400> SEQUENCE: 32

Ser Gly Xaa Thr Xaa Xaa Xaa Xaa Xaa Xaa Xaa Xaa Xaa Xaa Xaa
1               5                   10                  15

Xaa Xaa Asn Xaa Gly Xaa Ser Arg Ala Xaa Xaa
            20                  25

<210> SEQ ID NO 33
<211> LENGTH: 56
<212> TYPE: PRT
<213> ORGANISM: Artificial
<220> FEATURE:
<223> OTHER INFORMATION: A consensus sequence in a protein phosphatase
<220> FEATURE:
<221> NAME/KEY: misc_feature
<222> LOCATION: (4)..(4)
<223> OTHER INFORMATION: Xaa can be any naturally occurring amino acid,
      or preferably M or V
<220> FEATURE:
<221> NAME/KEY: misc_feature
<222> LOCATION: (5)..(5)
<223> OTHER INFORMATION: Xaa can be any naturally occurring amino acid,
      or preferably S or A
<220> FEATURE:
<221> NAME/KEY: misc_feature
<222> LOCATION: (7)..(7)
<223> OTHER INFORMATION: Xaa can be any naturally occurring amino acid,
      or preferably A or S
<220> FEATURE:
<221> NAME/KEY: misc_feature
<222> LOCATION: (8)..(8)
<223> OTHER INFORMATION: Xaa can be any naturally occurring amino acid,
      or preferably F or L
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid,
      or preferably L, I or V
<220> FEATURE:
<221> NAME/KEY: misc_feature
<222> LOCATION: (15)..(15)
<223> OTHER INFORMATION: Xaa can be any naturally occurring amino acid
<220> FEATURE:
```

-continued

```
<221> NAME/KEY: misc_feature
<222> LOCATION: (16)..(16)
<223> OTHER INFORMATION: Xaa can be any naturally occurring amino acid,
      or preferably Y, F or H
<220> FEATURE:
<221> NAME/KEY: misc_feature
<222> LOCATION: (18)..(18)
<223> OTHER INFORMATION: Xaa can be any naturally occurring amino acid,
      or preferably V or L
<220> FEATURE:
<221> NAME/KEY: misc_feature
<222> LOCATION: (19)..(19)
<223> OTHER INFORMATION: Xaa can be any naturally occurring amino acid,
      or preferably I or V
<220> FEATURE:
<221> NAME/KEY: misc_feature
<222> LOCATION: (20)..(21)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid,
      or preferably E, Q or D
<220> FEATURE:
<221> NAME/KEY: misc_feature
<222> LOCATION: (24)..(24)
<223> OTHER INFORMATION: Xaa can be any naturally occurring amino acid,
      or preferably I, V or F
<220> FEATURE:
<221> NAME/KEY: misc_feature
<222> LOCATION: (25)..(28)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid,
      or preferably I, L or V
<220> FEATURE:
<221> NAME/KEY: misc_feature
<222> LOCATION: (30)..(30)
<223> OTHER INFORMATION: Xaa can be any naturally occurring amino acid,
      or preferably T or S
<220> FEATURE:
<221> NAME/KEY: misc_feature
<222> LOCATION: (31)..(32)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid,
      or preferably F or Y
<220> FEATURE:
<221> NAME/KEY: misc_feature
<222> LOCATION: (36)..(36)
<223> OTHER INFORMATION: Xaa can be any naturally occurring amino acid,
      or preferably L, I, V or M
<220> FEATURE:
<221> NAME/KEY: misc_feature
<222> LOCATION: (37)..(37)
<223> OTHER INFORMATION: Xaa can be any naturally occurring amino acid,
      or preferably V, L or I
<220> FEATURE:
<221> NAME/KEY: misc_feature
<222> LOCATION: (40)..(40)
<223> OTHER INFORMATION: Xaa can be any naturally occurring amino acid,
      or preferably T or S
<220> FEATURE:
<221> NAME/KEY: misc_feature
<222> LOCATION: (43)..(43)
<223> OTHER INFORMATION: Xaa can be any naturally occurring amino acid,
      or preferably V, I or M
<220> FEATURE:
<221> NAME/KEY: misc_feature
<222> LOCATION: (46)..(46)
<223> OTHER INFORMATION: Xaa can be any naturally occurring amino acid
<220> FEATURE:
```

```
<221> NAME/KEY: misc_feature
<222> LOCATION: (47)..(47)
<223> OTHER INFORMATION: Xaa can be any naturally occurring amino acid,
      or preferably L, I, V or M
<220> FEATURE:
<221> NAME/KEY: misc_feature
<222> LOCATION: (48)..(48)
<223> OTHER INFORMATION: Xaa can be any naturally occurring amino acid,
      or preferably S or T
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid,
      or preferably E or D
<220> FEATURE:
<221> NAME/KEY: misc_feature
<222> LOCATION: (52)..(52)
<223> OTHER INFORMATION: Xaa can be any naturally occurring amino acid,
      or preferably V or A
<220> FEATURE:
<221> NAME/KEY: misc_feature
<222> LOCATION: (53)..(54)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid,
      or preferably L, V or I
<220> FEATURE:
<221> NAME/KEY: misc_feature
<222> LOCATION: (56)..(56)
<223> OTHER INFORMATION: Xaa can be any naturally occurring amino acid,
      or preferably I or V

<400> SEQUENCE: 33

Gly Leu Ala Xaa Xaa Arg Xaa Xaa Gly Asp Xaa Xaa Lys Xaa Xaa
1               5                   10                  15

Gly Xaa Xaa Xaa Xaa Pro Xaa Xaa Xaa Xaa Xaa Xaa Xaa Xaa Xaa
            20                  25                  30

Asp Xaa Xaa Xaa Xaa Leu Ala Xaa Asp Gly Xaa Trp Asp Xaa Xaa Xaa
        35                  40                  45

Asn Xaa Xaa Xaa Xaa Xaa Xaa Xaa
    50                  55

<210> SEQ ID NO 34
<211> LENGTH: 1122
<212> TYPE: DNA
<213> ORGANISM: Arabidopsis thaliana
<220> FEATURE:
<221> NAME/KEY: CDS
<222> LOCATION: (1)..(1122)

<400> SEQUENCE: 34 atg gga cat ttc tca tcg atg ttc aat gga tta gct cga tca ttt tct        48
Met Gly His Phe Ser Ser Met Phe Asn Gly Leu Ala Arg Ser Phe Ser
1               5                   10                  15 ata aag aaa gtg aag aac aac aat gga aac tgc gac gca aag gaa gct        96
Ile Lys Lys Val Lys Asn Asn Asn Gly Asn Cys Asp Ala Lys Glu Ala
            20                  25                  30 gct gat gag atg gca agc gag gct aag aaa aaa gaa ttg att ctg aaa       144
Ala Asp Glu Met Ala Ser Glu Ala Lys Lys Lys Glu Leu Ile Leu Lys
        35                  40                  45 tcc tct ggt tat gtt aat gta caa gga tct aat aat tta gcc tct ctt       192
Ser Ser Gly Tyr Val Asn Val Gln Gly Ser Asn Asn Leu Ala Ser Leu
    50                  55                  60 ttc tcc aaa cgc ggc gaa aaa ggc gtt aat cag gat tgt gca ctc gtt       240
```

```
Phe Ser Lys Arg Gly Glu Lys Gly Val Asn Gln Asp Cys Ala Leu Val
 65                  70                  75                  80 tgg gag gga ttt ggg tgc caa gaa gac atg atc ttc tgc ggg ata ttc    288
Trp Glu Gly Phe Gly Cys Gln Glu Asp Met Ile Phe Cys Gly Ile Phe
                 85                  90                  95 gat gga cac ggt cca tgg ggt cac tat gta gcc aaa caa gta aga aac    336
Asp Gly His Gly Pro Trp Gly His Tyr Val Ala Lys Gln Val Arg Asn
            100                 105                 110 tca atg cct ttg tcg ctt ctt tgc aac tgg caa aag att ctt gct cag    384
Ser Met Pro Leu Ser Leu Leu Cys Asn Trp Gln Lys Ile Leu Ala Gln
        115                 120                 125 gcc act cta gaa ccc gag ctc gac ctc gaa ggc tct aat aaa aaa atc    432
Ala Thr Leu Glu Pro Glu Leu Asp Leu Glu Gly Ser Asn Lys Lys Ile
    130                 135                 140 tca aga ttc gac ata tgg aag caa tcc tat cta aaa acg tgt gca acg    480
Ser Arg Phe Asp Ile Trp Lys Gln Ser Tyr Leu Lys Thr Cys Ala Thr
145                 150                 155                 160 gtt gat caa gag ctt gaa cat cac cgc aag atc gat tct tac tat agc    528
Val Asp Gln Glu Leu Glu His His Arg Lys Ile Asp Ser Tyr Tyr Ser
                165                 170                 175 ggc aca aca gct cta acc att gtg aga cag ggt gaa gtt att tat gta    576
Gly Thr Thr Ala Leu Thr Ile Val Arg Gln Gly Glu Val Ile Tyr Val
            180                 185                 190 gca aat gta ggc gat tca aga gcg gta cta gcc atg gag tcg gat gag    624
Ala Asn Val Gly Asp Ser Arg Ala Val Leu Ala Met Glu Ser Asp Glu
        195                 200                 205 gga agc ttg gtt gcg gtt cag ctc acc ctc gat ttc aaa ccg aat cta    672
Gly Ser Leu Val Ala Val Gln Leu Thr Leu Asp Phe Lys Pro Asn Leu
    210                 215                 220 cca cag gag aag gag cgg ata att ggc tgc aaa ggg cgg gtt ttc tgt    720
Pro Gln Glu Lys Glu Arg Ile Ile Gly Cys Lys Gly Arg Val Phe Cys
225                 230                 235                 240 cta gat gat gag ccg gga gtc cat cgt gtg tgg cag cca gac gca gaa    768
Leu Asp Asp Glu Pro Gly Val His Arg Val Trp Gln Pro Asp Ala Glu
                245                 250                 255 aca ccg ggg ctc gca atg tca aga gca ttc gga gac tac tgt att aaa    816
Thr Pro Gly Leu Ala Met Ser Arg Ala Phe Gly Asp Tyr Cys Ile Lys
            260                 265                 270 gag tat gga ttg gtc tca gtc cct gaa gtc act caa aga cac atc tct    864
Glu Tyr Gly Leu Val Ser Val Pro Glu Val Thr Gln Arg His Ile Ser
        275                 280                 285 act aaa gac cac ttc ata atc ttg gcc agt gat ggg ata tgg gat gtg    912
Thr Lys Asp His Phe Ile Ile Leu Ala Ser Asp Gly Ile Trp Asp Val
    290                 295                 300 atc tct aac caa gag gct ata gag att gtc tcc tca acg gct gag cgg    960
Ile Ser Asn Gln Glu Ala Ile Glu Ile Val Ser Ser Thr Ala Glu Arg
305                 310                 315                 320 cct aag gcg gct aag cga tta gta gag caa gcg gtt cgg gct tgg aag   1008
Pro Lys Ala Ala Lys Arg Leu Val Glu Gln Ala Val Arg Ala Trp Lys
                325                 330                 335 aaa aag aga cga gga tac tcc atg gat gat atg tca gtc gtc tgc ctc   1056
Lys Lys Arg Arg Gly Tyr Ser Met Asp Asp Met Ser Val Val Cys Leu
            340                 345                 350 ttc ctc cat tct tct tca tcg tca tct cta tca caa cat cat cat gcc   1104
Phe Leu His Ser Ser Ser Ser Ser Ser Leu Ser Gln His His His Ala
        355                 360                 365 atg acg att tta aag taa                                           1122
Met Thr Ile Leu Lys
    370
```

```
<210> SEQ ID NO 35
<211> LENGTH: 373
<212> TYPE: PRT
<213> ORGANISM: Arabidopsis thaliana

<400> SEQUENCE: 35

Met Gly His Phe Ser Ser Met Phe Asn Gly Leu Ala Arg Ser Phe Ser
1               5                   10                  15

Ile Lys Lys Val Lys Asn Asn Gly Asn Cys Asp Ala Lys Glu Ala
            20                  25                  30

Ala Asp Glu Met Ala Ser Glu Ala Lys Lys Glu Leu Ile Leu Lys
        35                  40                  45

Ser Ser Gly Tyr Val Asn Val Gln Gly Ser Asn Asn Leu Ala Ser Leu
    50                  55                  60

Phe Ser Lys Arg Gly Glu Lys Gly Val Asn Gln Asp Cys Ala Leu Val
65                  70                  75                  80

Trp Glu Gly Phe Gly Cys Gln Glu Asp Met Ile Phe Cys Gly Ile Phe
                85                  90                  95

Asp Gly His Gly Pro Trp Gly His Tyr Val Ala Lys Gln Val Arg Asn
            100                 105                 110

Ser Met Pro Leu Ser Leu Leu Cys Asn Trp Gln Lys Ile Leu Ala Gln
        115                 120                 125

Ala Thr Leu Glu Pro Glu Leu Asp Leu Glu Gly Ser Asn Lys Lys Ile
    130                 135                 140

Ser Arg Phe Asp Ile Trp Lys Gln Ser Tyr Leu Lys Thr Cys Ala Thr
145                 150                 155                 160

Val Asp Gln Glu Leu Glu His His Arg Lys Ile Asp Ser Tyr Tyr Ser
                165                 170                 175

Gly Thr Thr Ala Leu Thr Ile Val Arg Gln Gly Glu Val Ile Tyr Val
            180                 185                 190

Ala Asn Val Gly Asp Ser Arg Ala Val Leu Ala Met Glu Ser Asp Glu
        195                 200                 205

Gly Ser Leu Val Ala Val Gln Leu Thr Leu Asp Phe Lys Pro Asn Leu
    210                 215                 220

Pro Gln Glu Lys Glu Arg Ile Ile Gly Cys Lys Gly Arg Val Phe Cys
225                 230                 235                 240

Leu Asp Asp Glu Pro Gly Val His Arg Val Trp Gln Pro Asp Ala Glu
                245                 250                 255

Thr Pro Gly Leu Ala Met Ser Arg Ala Phe Gly Asp Tyr Cys Ile Lys
            260                 265                 270

Glu Tyr Gly Leu Val Ser Val Pro Glu Val Thr Gln Arg His Ile Ser
        275                 280                 285

Thr Lys Asp His Phe Ile Ile Leu Ala Ser Asp Gly Ile Trp Asp Val
    290                 295                 300

Ile Ser Asn Gln Glu Ala Ile Glu Ile Val Ser Ser Thr Ala Glu Arg
305                 310                 315                 320

Pro Lys Ala Ala Lys Arg Leu Val Glu Gln Ala Val Arg Ala Trp Lys
                325                 330                 335

Lys Lys Arg Arg Gly Tyr Ser Met Asp Asp Met Ser Val Val Cys Leu
            340                 345                 350

Phe Leu His Ser Ser Ser Ser Ser Leu Ser Gln His His His Ala
        355                 360                 365

Met Thr Ile Leu Lys
    370
```

<210> SEQ ID NO 36
<211> LENGTH: 1584
<212> TYPE: DNA
<213> ORGANISM: Arabidopsis thaliana
<220> FEATURE:
<221> NAME/KEY: CDS
<222> LOCATION: (1)..(1584)

<400> SEQUENCE: 36

| | | | | | | | | | | | | | | | | |
|---|---|---|---|---|---|---|---|---|---|---|---|---|---|---|---|---|
| atg | ggg | tcc | tgt | tta | tct | gca | gag | agc | agg | agc | cct | aga | ccg | ggc | tct | 48 |
| Met | Gly | Ser | Cys | Leu | Ser | Ala | Glu | Ser | Arg | Ser | Pro | Arg | Pro | Gly | Ser | |
| 1 | | | | 5 | | | | | 10 | | | | | 15 | | |
| cct | tgc | tct | cct | gct | ttt | agt | gtg | agg | aag | agg | aag | aac | tct | aag | aag | 96 |
| Pro | Cys | Ser | Pro | Ala | Phe | Ser | Val | Arg | Lys | Arg | Lys | Asn | Ser | Lys | Lys | |
| | | | 20 | | | | | 25 | | | | | 30 | | | |
| cga | cct | ggt | tct | agg | aac | tct | tcc | ttt | gat | tac | cgg | aga | gaa | gaa | ccg | 144 |
| Arg | Pro | Gly | Ser | Arg | Asn | Ser | Ser | Phe | Asp | Tyr | Arg | Arg | Glu | Glu | Pro | |
| | | 35 | | | | | 40 | | | | | 45 | | | | |
| ttg | aat | cag | gtt | ccg | ggc | cgg | atg | ttc | ttg | aat | gga | tca | act | gag | gtt | 192 |
| Leu | Asn | Gln | Val | Pro | Gly | Arg | Met | Phe | Leu | Asn | Gly | Ser | Thr | Glu | Val | |
| | 50 | | | | | 55 | | | | | 60 | | | | | |
| gct | tgt | atc | tac | act | caa | caa | ggc | aag | aaa | ggg | cct | aat | caa | gat | gcc | 240 |
| Ala | Cys | Ile | Tyr | Thr | Gln | Gln | Gly | Lys | Lys | Gly | Pro | Asn | Gln | Asp | Ala | |
| 65 | | | | | 70 | | | | | 75 | | | | | 80 | |
| atg | gtt | gtt | tgg | gag | aat | ttt | ggt | tcg | agg | aca | gat | aca | atc | ttc | tgt | 288 |
| Met | Val | Val | Trp | Glu | Asn | Phe | Gly | Ser | Arg | Thr | Asp | Thr | Ile | Phe | Cys | |
| | | | | 85 | | | | | 90 | | | | | 95 | | |
| gga | gtg | ttt | gat | gga | cat | ggt | cca | tat | ggt | cat | atg | gtt | gca | aag | aga | 336 |
| Gly | Val | Phe | Asp | Gly | His | Gly | Pro | Tyr | Gly | His | Met | Val | Ala | Lys | Arg | |
| | | | 100 | | | | | 105 | | | | | 110 | | | |
| gtc | aga | gac | aat | ctt | cct | ctc | aaa | tta | agt | gct | tat | tgg | gaa | gca | aaa | 384 |
| Val | Arg | Asp | Asn | Leu | Pro | Leu | Lys | Leu | Ser | Ala | Tyr | Trp | Glu | Ala | Lys | |
| | | 115 | | | | | 120 | | | | | 125 | | | | |
| gta | cca | gtt | gaa | ggt | gtt | ctt | aag | gca | atc | acc | acc | gac | act | gtc | aat | 432 |
| Val | Pro | Val | Glu | Gly | Val | Leu | Lys | Ala | Ile | Thr | Thr | Asp | Thr | Val | Asn | |
| | 130 | | | | | 135 | | | | | 140 | | | | | |
| aat | gta | acc | aac | att | aac | aac | cct | gaa | gat | gct | gct | gct | gct | gct | gct | 480 |
| Asn | Val | Thr | Asn | Ile | Asn | Asn | Pro | Glu | Asp | Ala | Ala | Ala | Ala | Ala | Ala | |
| 145 | | | | | 150 | | | | | 155 | | | | | 160 | |
| ttt | gtc | act | gct | gaa | gaa | gaa | cct | agg | aca | tct | gct | gac | atg | gag | gag | 528 |
| Phe | Val | Thr | Ala | Glu | Glu | Glu | Pro | Arg | Thr | Ser | Ala | Asp | Met | Glu | Glu | |
| | | | | 165 | | | | | 170 | | | | | 175 | | |
| gag | aac | aca | gaa | acc | caa | ccg | gaa | ttg | ttt | caa | acg | ctg | aaa | gag | tcg | 576 |
| Glu | Asn | Thr | Glu | Thr | Gln | Pro | Glu | Leu | Phe | Gln | Thr | Leu | Lys | Glu | Ser | |
| | | | 180 | | | | | 185 | | | | | 190 | | | |
| ttt | ctt | aag | gct | ttt | aaa | gtt | atg | gat | aga | gag | ctt | aaa | ttc | cat | gga | 624 |
| Phe | Leu | Lys | Ala | Phe | Lys | Val | Met | Asp | Arg | Glu | Leu | Lys | Phe | His | Gly | |
| | | 195 | | | | | 200 | | | | | 205 | | | | |
| agt | gtt | gac | tgt | ttc | tgc | agt | ggg | aca | aca | gct | gta | acc | ttg | atc | aag | 672 |
| Ser | Val | Asp | Cys | Phe | Cys | Ser | Gly | Thr | Thr | Ala | Val | Thr | Leu | Ile | Lys | |
| | 210 | | | | | 215 | | | | | 220 | | | | | |
| cag | ggt | cag | tat | ctc | gtt | gtt | gga | aat | gtt | ggg | gat | tcc | aga | gct | gta | 720 |
| Gln | Gly | Gln | Tyr | Leu | Val | Val | Gly | Asn | Val | Gly | Asp | Ser | Arg | Ala | Val | |
| 225 | | | | | 230 | | | | | 235 | | | | | 240 | |
| atg | ggt | aca | aga | gac | agt | gaa | aat | act | ctt | gtc | gct | gtt | caa | cta | act | 768 |
| Met | Gly | Thr | Arg | Asp | Ser | Glu | Asn | Thr | Leu | Val | Ala | Val | Gln | Leu | Thr | |
| | | | | 245 | | | | | 250 | | | | | 255 | | |
| gtg | gat | ctt | aag | cca | aat | ctc | cca | ggt | tgg | att | atc | tta | tgt | gaa | tgt | 816 |
| Val | Asp | Leu | Lys | Pro | Asn | Leu | Pro | Gly | Trp | Ile | Ile | Leu | Cys | Glu | Cys | |
| | | | 260 | | | | | 265 | | | | | 270 | | | |
| atg | atg | ttg | tcc | tgt | gga | tgt | atg | atg | gat | cca | tta | atc | atg | ttt | att | 864 |
| Met | Met | Leu | Ser | Cys | Gly | Cys | Met | Met | Asp | Pro | Leu | Ile | Met | Phe | Ile | |

```
                 275                 280                 285
ggg ttt ttt ttt att ccc tca att gaa ctt gca gct gag gca gag aga        912
Gly Phe Phe Phe Ile Pro Ser Ile Glu Leu Ala Ala Glu Ala Glu Arg
            290                 295                 300 ata aga aag tgt cga gga cga gtg ttt gct ctt aga gat gaa cct gaa        960
Ile Arg Lys Cys Arg Gly Arg Val Phe Ala Leu Arg Asp Glu Pro Glu
305                 310                 315                 320 gtt tgt aga gtt tgg ctg cca aat tgt gac tca cct gga ctt gct atg       1008
Val Cys Arg Val Trp Leu Pro Asn Cys Asp Ser Pro Gly Leu Ala Met
                325                 330                 335 gca cgt gct ttt ggt gac ttt tgc ctt aaa gat ttt ggc cta atc tct       1056
Ala Arg Ala Phe Gly Asp Phe Cys Leu Lys Asp Phe Gly Leu Ile Ser
            340                 345                 350 gtg cct gat gta tct ttc cgt cag tta acc gaa aaa gat gag ttt ata       1104
Val Pro Asp Val Ser Phe Arg Gln Leu Thr Glu Lys Asp Glu Phe Ile
        355                 360                 365 gtg ttg gct aca gat ggg att tgg gat gtt ctc tca aat gaa gat gta       1152
Val Leu Ala Thr Asp Gly Ile Trp Asp Val Leu Ser Asn Glu Asp Val
    370                 375                 380 gtg gcg att gta gct tca gct cca tcg cgc tcc tct gca gca aga gct       1200
Val Ala Ile Val Ala Ser Ala Pro Ser Arg Ser Ser Ala Ala Arg Ala
385                 390                 395                 400 tta gtc gag tct gcg gtc aga gct tgg aga tac aaa tac ccg act tcc       1248
Leu Val Glu Ser Ala Val Arg Ala Trp Arg Tyr Lys Tyr Pro Thr Ser
                405                 410                 415 aaa gtc gat gac tgt gcc gct gtt tgc ttg tat cta gac tcc agc aac       1296
Lys Val Asp Asp Cys Ala Ala Val Cys Leu Tyr Leu Asp Ser Ser Asn
            420                 425                 430 aca aac gcc ata tct aca gct tct tcc atc tcc aaa ctt gaa gat gga       1344
Thr Asn Ala Ile Ser Thr Ala Ser Ser Ile Ser Lys Leu Glu Asp Gly
        435                 440                 445 gaa gaa gaa gaa cta aaa gcc acg act gag gat gat gat gca tca gga       1392
Glu Glu Glu Glu Leu Lys Ala Thr Thr Glu Asp Asp Asp Ala Ser Gly
    450                 455                 460 cca agc ggt cta ggc cgt tcg agt act gtc agg tcg ggg aaa gag att       1440
Pro Ser Gly Leu Gly Arg Ser Ser Thr Val Arg Ser Gly Lys Glu Ile
465                 470                 475                 480 gct ctc gac gaa agt gaa act gag aag ctg ata aaa gaa gcg gat aac       1488
Ala Leu Asp Glu Ser Glu Thr Glu Lys Leu Ile Lys Glu Ala Asp Asn
                485                 490                 495 ttg gat tca gaa cct gga aca gag tat tct gca ctt gaa ggt gtt gca       1536
Leu Asp Ser Glu Pro Gly Thr Glu Tyr Ser Ala Leu Glu Gly Val Ala
            500                 505                 510 aga gtt aat aca ctt tta aac tta cca aga ttt gtg cct gga aag tga       1584
Arg Val Asn Thr Leu Leu Asn Leu Pro Arg Phe Val Pro Gly Lys
        515                 520                 525

<210> SEQ ID NO 37
<211> LENGTH: 527
<212> TYPE: PRT
<213> ORGANISM: Arabidopsis thaliana

<400> SEQUENCE: 37

Met Gly Ser Cys Leu Ser Ala Glu Ser Arg Ser Pro Arg Pro Gly Ser
1               5                   10                  15

Pro Cys Ser Pro Ala Phe Ser Val Arg Lys Arg Lys Asn Ser Lys Lys
            20                  25                  30

Arg Pro Gly Ser Arg Asn Ser Ser Phe Asp Tyr Arg Arg Glu Glu Pro
        35                  40                  45

Leu Asn Gln Val Pro Gly Arg Met Phe Leu Asn Gly Ser Thr Glu Val
```

```
            50                  55                  60
Ala Cys Ile Tyr Thr Gln Gln Gly Lys Lys Gly Pro Asn Gln Asp Ala
 65                  70                  75                  80

Met Val Val Trp Glu Asn Phe Gly Ser Arg Thr Asp Thr Ile Phe Cys
                     85                  90                  95

Gly Val Phe Asp Gly His Gly Pro Tyr Gly His Met Val Ala Lys Arg
                    100                 105                 110

Val Arg Asp Asn Leu Pro Leu Lys Leu Ser Ala Tyr Trp Glu Ala Lys
                    115                 120                 125

Val Pro Val Glu Gly Val Leu Lys Ala Ile Thr Thr Asp Thr Val Asn
                    130                 135                 140

Asn Val Thr Asn Ile Asn Asn Pro Glu Asp Ala Ala Ala Ala Ala Ala
145                 150                 155                 160

Phe Val Thr Ala Glu Glu Pro Arg Thr Ser Ala Asp Met Glu Glu
                    165                 170                 175

Glu Asn Thr Glu Thr Gln Pro Glu Leu Phe Gln Thr Leu Lys Glu Ser
                    180                 185                 190

Phe Leu Lys Ala Phe Lys Val Met Asp Arg Glu Leu Lys Phe His Gly
                    195                 200                 205

Ser Val Asp Cys Phe Cys Ser Gly Thr Thr Ala Val Thr Leu Ile Lys
210                 215                 220

Gln Gly Gln Tyr Leu Val Val Gly Asn Val Gly Asp Ser Arg Ala Val
225                 230                 235                 240

Met Gly Thr Arg Asp Ser Glu Asn Thr Leu Val Ala Val Gln Leu Thr
                    245                 250                 255

Val Asp Leu Lys Pro Asn Leu Pro Gly Trp Ile Ile Leu Cys Glu Cys
                    260                 265                 270

Met Met Leu Ser Cys Gly Cys Met Met Asp Pro Leu Ile Met Phe Ile
                    275                 280                 285

Gly Phe Phe Phe Ile Pro Ser Ile Glu Leu Ala Ala Glu Ala Glu Arg
                    290                 295                 300

Ile Arg Lys Cys Arg Gly Arg Val Phe Ala Leu Arg Asp Glu Pro Glu
305                 310                 315                 320

Val Cys Arg Val Trp Leu Pro Asn Cys Asp Ser Pro Gly Leu Ala Met
                    325                 330                 335

Ala Arg Ala Phe Gly Asp Phe Cys Leu Lys Asp Phe Gly Leu Ile Ser
                    340                 345                 350

Val Pro Asp Val Ser Phe Arg Gln Leu Thr Glu Lys Asp Glu Phe Ile
                    355                 360                 365

Val Leu Ala Thr Asp Gly Ile Trp Asp Val Leu Ser Asn Glu Asp Val
370                 375                 380

Val Ala Ile Val Ala Ser Ala Pro Ser Arg Ser Ser Ala Ala Arg Ala
385                 390                 395                 400

Leu Val Glu Ser Ala Val Arg Ala Trp Arg Tyr Lys Tyr Pro Thr Ser
                    405                 410                 415

Lys Val Asp Asp Cys Ala Ala Val Cys Leu Tyr Leu Asp Ser Ser Asn
                    420                 425                 430

Thr Asn Ala Ile Ser Thr Ala Ser Ile Ser Lys Leu Glu Asp Gly
                    435                 440                 445

Glu Glu Glu Glu Leu Lys Ala Thr Thr Glu Asp Asp Ala Ser Gly
                    450                 455                 460

Pro Ser Gly Leu Gly Arg Ser Thr Val Arg Ser Gly Lys Glu Ile
465                 470                 475                 480
```

```
Ala Leu Asp Glu Ser Glu Thr Glu Lys Leu Ile Lys Glu Ala Asp Asn
            485                 490                 495

Leu Asp Ser Glu Pro Gly Thr Glu Tyr Ser Ala Leu Glu Gly Val Ala
            500                 505                 510

Arg Val Asn Thr Leu Leu Asn Leu Pro Arg Phe Val Pro Gly Lys
            515                 520                 525

<210> SEQ ID NO 38
<211> LENGTH: 1056
<212> TYPE: DNA
<213> ORGANISM: Arabidopsis thaliana
<220> FEATURE:
<221> NAME/KEY: CDS
<222> LOCATION: (1)..(1056)

<400> SEQUENCE: 38 atg gtg ctt tta cca gcg ttt ttg gac gga tta gcg aga act gta tcg       48
Met Val Leu Leu Pro Ala Phe Leu Asp Gly Leu Ala Arg Thr Val Ser
1               5                   10                  15 acg aag aaa ggt aaa aaa cta tcg gaa gat gaa gat gga ggg aga gag       96
Thr Lys Lys Gly Lys Lys Leu Ser Glu Asp Glu Asp Gly Gly Arg Glu
            20                  25                  30 atc gca aaa tcg atg att aaa gat tcg aag aag aac tcg acg ttg ctc      144
Ile Ala Lys Ser Met Ile Lys Asp Ser Lys Lys Asn Ser Thr Leu Leu
        35                  40                  45 ggt act tca ggc ttt gtt agc tcc gaa agt tct aag agg ttt acc tct      192
Gly Thr Ser Gly Phe Val Ser Ser Glu Ser Ser Lys Arg Phe Thr Ser
    50                  55                  60 att tgt tct aat aga ggt gag aaa gga atc aac caa gat cgt gca att      240
Ile Cys Ser Asn Arg Gly Glu Lys Gly Ile Asn Gln Asp Arg Ala Ile
65                  70                  75                  80 gtt tgg gag gga ttt ggg tgc caa gaa gac ata aca ttt tgt ggg atg      288
Val Trp Glu Gly Phe Gly Cys Gln Glu Asp Ile Thr Phe Cys Gly Met
                85                  90                  95 ttt gat gga cat gga cca tgg gga cat gtg ata gcc aaa aga gta aaa      336
Phe Asp Gly His Gly Pro Trp Gly His Val Ile Ala Lys Arg Val Lys
            100                 105                 110 aaa tca ttt cca tct tct ctg ctt tgc caa tgg caa caa act ctt gcc      384
Lys Ser Phe Pro Ser Ser Leu Leu Cys Gln Trp Gln Gln Thr Leu Ala
        115                 120                 125 tcc tta tca tcc tcg ccg gaa tgt tcc tct ccg ttt gat ctt tgg aag      432
Ser Leu Ser Ser Ser Pro Glu Cys Ser Ser Pro Phe Asp Leu Trp Lys
    130                 135                 140 caa gct tgc ctg aaa aca ttc tcc atc atc gat ctt gat ctc aag atc      480
Gln Ala Cys Leu Lys Thr Phe Ser Ile Ile Asp Leu Asp Leu Lys Ile
145                 150                 155                 160 agt cct tcc att gat tct tac tgt agc ggc tgc acc gct ctc acc gct      528
Ser Pro Ser Ile Asp Ser Tyr Cys Ser Gly Cys Thr Ala Leu Thr Ala
                165                 170                 175 gtt ttg cag ggt gat cat ctc gtt ata gca aat gcg ggt gac tca cga      576
Val Leu Gln Gly Asp His Leu Val Ile Ala Asn Ala Gly Asp Ser Arg
            180                 185                 190 gca gta ata gca aca act tct gat gat gga aac ggt tta gtc ccg gtt      624
Ala Val Ile Ala Thr Thr Ser Asp Asp Gly Asn Gly Leu Val Pro Val
        195                 200                 205 cag ctc tcg gta gac ttt aaa cca aac att ccc gag gaa gca gaa cgg      672
Gln Leu Ser Val Asp Phe Lys Pro Asn Ile Pro Glu Glu Ala Glu Arg
    210                 215                 220 ata aaa caa tcg gat gga cga ttg ttc tgc cta gac gat gaa ccg gga      720
Ile Lys Gln Ser Asp Gly Arg Leu Phe Cys Leu Asp Asp Glu Pro Gly
225                 230                 235                 240
```

```
gtg tac cgg gtg ggt atg cct aat gga gga tca ctc ggt tta gct gtt    768
Val Tyr Arg Val Gly Met Pro Asn Gly Gly Ser Leu Gly Leu Ala Val
                245                 250                 255 tca aga gcg ttt gga gat tac tgc ctt aaa gac ttc ggt tta gtc tct    816
Ser Arg Ala Phe Gly Asp Tyr Cys Leu Lys Asp Phe Gly Leu Val Ser
            260                 265                 270 gaa ccg gaa gta aca tac cga aag ata acc gac aag gac cag ttt cta    864
Glu Pro Glu Val Thr Tyr Arg Lys Ile Thr Asp Lys Asp Gln Phe Leu
        275                 280                 285 atc ttg gcc acc gat ggg atg tgg gat gtg atg acg aat aat gag gca    912
Ile Leu Ala Thr Asp Gly Met Trp Asp Val Met Thr Asn Asn Glu Ala
    290                 295                 300 gtg gag ata gta aga gga gtt aaa gag aga aga aag agc gca aag aga    960
Val Glu Ile Val Arg Gly Val Lys Glu Arg Arg Lys Ser Ala Lys Arg
305                 310                 315                 320 ttg gta gag aga gct gtg acg ctt tgg cgt agg aag aga aga agc atc   1008
Leu Val Glu Arg Ala Val Thr Leu Trp Arg Arg Lys Arg Arg Ser Ile
                325                 330                 335 gcc atg gat gat att tct gtt ctc tgt ctc ttt cgt cct tct tag       1056
Ala Met Asp Asp Ile Ser Val Leu Cys Leu Phe Arg Pro Ser
            340                 345                 350
```

<210> SEQ ID NO 39
<211> LENGTH: 351
<212> TYPE: PRT
<213> ORGANISM: Arabidopsis thaliana

<400> SEQUENCE: 39

```
Met Val Leu Leu Pro Ala Phe Leu Asp Gly Leu Ala Arg Thr Val Ser
1               5                   10                  15

Thr Lys Lys Gly Lys Lys Leu Ser Glu Asp Glu Asp Gly Gly Arg Glu
            20                  25                  30

Ile Ala Lys Ser Met Ile Lys Asp Ser Lys Lys Asn Ser Thr Leu Leu
        35                  40                  45

Gly Thr Ser Gly Phe Val Ser Ser Glu Ser Ser Lys Arg Phe Thr Ser
    50                  55                  60

Ile Cys Ser Asn Arg Gly Glu Lys Gly Ile Asn Gln Asp Arg Ala Ile
65                  70                  75                  80

Val Trp Glu Gly Phe Gly Cys Gln Glu Asp Ile Thr Phe Cys Gly Met
                85                  90                  95

Phe Asp Gly His Gly Pro Trp Gly His Val Ile Ala Lys Arg Val Lys
            100                 105                 110

Lys Ser Phe Pro Ser Ser Leu Leu Cys Gln Trp Gln Thr Leu Ala
        115                 120                 125

Ser Leu Ser Ser Ser Pro Glu Cys Ser Ser Pro Phe Asp Leu Trp Lys
    130                 135                 140

Gln Ala Cys Leu Lys Thr Phe Ser Ile Ile Asp Leu Asp Leu Lys Ile
145                 150                 155                 160

Ser Pro Ser Ile Asp Ser Tyr Cys Ser Gly Cys Thr Ala Leu Thr Ala
                165                 170                 175

Val Leu Gln Gly Asp His Leu Val Ile Ala Asn Ala Gly Asp Ser Arg
            180                 185                 190

Ala Val Ile Ala Thr Thr Ser Asp Asp Gly Asn Gly Leu Val Pro Val
        195                 200                 205

Gln Leu Ser Val Asp Phe Lys Pro Asn Ile Pro Glu Glu Ala Glu Arg
    210                 215                 220

Ile Lys Gln Ser Asp Gly Arg Leu Phe Cys Leu Asp Asp Glu Pro Gly
225                 230                 235                 240
```

```
Val Tyr Arg Val Gly Met Pro Asn Gly Gly Ser Leu Gly Leu Ala Val
            245                 250                 255

Ser Arg Ala Phe Gly Asp Tyr Cys Leu Lys Asp Phe Gly Leu Val Ser
            260                 265                 270

Glu Pro Glu Val Thr Tyr Arg Lys Ile Thr Asp Lys Asp Gln Phe Leu
            275                 280                 285

Ile Leu Ala Thr Asp Gly Met Trp Asp Val Met Thr Asn Asn Glu Ala
            290                 295                 300

Val Glu Ile Val Arg Gly Val Lys Glu Arg Lys Ser Ala Lys Arg
305                 310                 315                 320

Leu Val Glu Arg Ala Val Thr Leu Trp Arg Arg Lys Arg Arg Ser Ile
            325                 330                 335

Ala Met Asp Asp Ile Ser Val Leu Cys Leu Phe Phe Arg Pro Ser
            340                 345                 350

<210> SEQ ID NO 40
<211> LENGTH: 3261
<212> TYPE: DNA
<213> ORGANISM: Oryza sativa
<220> FEATURE:
<221> NAME/KEY: CDS
<222> LOCATION: (1)..(3261)

<400> SEQUENCE: 40
```

| | | |
|---|---|---|
| atg ggc tgc tca cct tct aag gtg tgt tca tgt cca cat tat aag ggc<br>Met Gly Cys Ser Pro Ser Lys Val Cys Ser Cys Pro His Tyr Lys Gly<br>1               5                   10                  15 | 48 |
| agt ttg tgc ttc tgt gac tgt gga tgc ttt gga caa aca cct gac tcc<br>Ser Leu Cys Phe Cys Asp Cys Gly Cys Phe Gly Gln Thr Pro Asp Ser<br>            20                  25                  30 | 96 |
| cca aga gag tca agg gga aaa tca aac cgg gtt agg gaa aag aca gat<br>Pro Arg Glu Ser Arg Gly Lys Ser Asn Arg Val Arg Gly Lys Thr Asp<br>        35                  40                  45 | 144 |
| tct agt gct tca gat gct tct tct gat gac cta gag gaa gat gat gat<br>Ser Ser Ala Ser Asp Ala Ser Ser Asp Asp Leu Glu Glu Asp Asp Asp<br>    50                  55                  60 | 192 |
| gga ttg cac caa atg aac att aca agg gac tct aat gtt ggt atc aat<br>Gly Leu His Gln Met Asn Ile Thr Arg Asp Ser Asn Val Gly Ile Asn<br>65                  70                  75                  80 | 240 |
| cga ctc tca agg gtc tca tca caa ttt ctt cca cca gaa ggt tca cgt<br>Arg Leu Ser Arg Val Ser Ser Gln Phe Leu Pro Pro Glu Gly Ser Arg<br>                85                  90                  95 | 288 |
| aaa gtt cga atc cca ttg ggg aat tat gac ctg aga tat tcc tac ttg<br>Lys Val Arg Ile Pro Leu Gly Asn Tyr Asp Leu Arg Tyr Ser Tyr Leu<br>            100                 105                 110 | 336 |
| tct caa aga ggc tac tac cca gaa tca ttg gac aag cca aac caa gac<br>Ser Gln Arg Gly Tyr Tyr Pro Glu Ser Leu Asp Lys Pro Asn Gln Asp<br>        115                 120                 125 | 384 |
| agt ttt tgt ata cat act cca ttt gga aca agc cct gat gac cat ttc<br>Ser Phe Cys Ile His Thr Pro Phe Gly Thr Ser Pro Asp Asp His Phe<br>    130                 135                 140 | 432 |
| ttt ggt gta ttt gat ggc cat gga gaa tat gga gct cag tgc tca caa<br>Phe Gly Val Phe Asp Gly His Gly Glu Tyr Gly Ala Gln Cys Ser Gln<br>145                 150                 155                 160 | 480 |
| ttt gta aag cga aga cta tgc gaa aac ctg ctc aga gat gac cgg ttc<br>Phe Val Lys Arg Arg Leu Cys Glu Asn Leu Leu Arg Asp Asp Arg Phe<br>                165                 170                 175 | 528 |
| cgt act gat gtt gtt cag gct ctt cat tct gct ttc ttg gca aca aat<br>Arg Thr Asp Val Val Gln Ala Leu His Ser Ala Phe Leu Ala Thr Asn<br>            180                 185                 190 | 576 |

```
                          -continued tca cag ctt cat gca gac agc tta gat gat tct atg agt ggt act act    624
Ser Gln Leu His Ala Asp Ser Leu Asp Asp Ser Met Ser Gly Thr Thr
        195                 200                 205 gca gtc act gtg ctg gtg agg ggt aaa act att tac att gcg aat acg    672
Ala Val Thr Val Leu Val Arg Gly Lys Thr Ile Tyr Ile Ala Asn Thr
210                 215                 220 ggt gat tca cgt gct gtt att gcc gaa aaa aga ggg gaa gat gtt gtt    720
Gly Asp Ser Arg Ala Val Ile Ala Glu Lys Arg Gly Glu Asp Val Val
225                 230                 235                 240 gct gtt gac ctg tcc ata gat caa aca ccc tac agg act gat gag ctt    768
Ala Val Asp Leu Ser Ile Asp Gln Thr Pro Tyr Arg Thr Asp Glu Leu
                245                 250                 255 gaa agg gtc aag gag tgt ggt gct agg gtt atg acg ttg gat cag ata    816
Glu Arg Val Lys Glu Cys Gly Ala Arg Val Met Thr Leu Asp Gln Ile
        260                 265                 270 gag ggg cta aag aac cca gat gta cag tgt tgg ggc acc gag gaa agt    864
Glu Gly Leu Lys Asn Pro Asp Val Gln Cys Trp Gly Thr Glu Glu Ser
    275                 280                 285 gat gac ggt gat cct cca agg ttg tgg gtg caa aat ggc atg tat cca    912
Asp Asp Gly Asp Pro Pro Arg Leu Trp Val Gln Asn Gly Met Tyr Pro
290                 295                 300 gga act gct ttt act cgc agc att gga gat tct gtc gct gaa tct atc    960
Gly Thr Ala Phe Thr Arg Ser Ile Gly Asp Ser Val Ala Glu Ser Ile
305                 310                 315                 320 ggt gtt gtc gct aat cct gag att ttt atc ctg gag ctc aat gcc aac   1008
Gly Val Val Ala Asn Pro Glu Ile Phe Ile Leu Glu Leu Asn Ala Asn
                325                 330                 335 cat cca ttc ttt gtt ctt gct agt gat gga gtt ttt gag ttt ctt tct   1056
His Pro Phe Phe Val Leu Ala Ser Asp Gly Val Phe Glu Phe Leu Ser
        340                 345                 350 agt caa act gtt gtc gac atg att gct aaa tac aag gat cct cgt gat   1104
Ser Gln Thr Val Val Asp Met Ile Ala Lys Tyr Lys Asp Pro Arg Asp
    355                 360                 365 gcg tgc gct gca att gtt gct gaa tcc tat cgc ctc tgg cta cag tat   1152
Ala Cys Ala Ala Ile Val Ala Glu Ser Tyr Arg Leu Trp Leu Gln Tyr
370                 375                 380 gaa act cgt aca gat gac att aca ata ata gtt gtt cat att aac ggg   1200
Glu Thr Arg Thr Asp Asp Ile Thr Ile Ile Val Val His Ile Asn Gly
385                 390                 395                 400 tta act gat atg gaa tgt act caa act gta atg aaa gta tct tta caa   1248
Leu Thr Asp Met Glu Cys Thr Gln Thr Val Met Lys Val Ser Leu Gln
                405                 410                 415 cct tcc caa caa gtc gta gaa ttg gta ggc tca gaa tca cca tcg aca   1296
Pro Ser Gln Gln Val Val Glu Leu Val Gly Ser Glu Ser Pro Ser Thr
        420                 425                 430 ata agt ttg aat ccc aag aac cag cgt tcc agg caa gat cta tca cgt   1344
Ile Ser Leu Asn Pro Lys Asn Gln Arg Ser Arg Gln Asp Leu Ser Arg
    435                 440                 445 gct cgg ctg aga gca ctt gaa agt tcc ctg gaa aat ggt cga cta tgg   1392
Ala Arg Leu Arg Ala Leu Glu Ser Ser Leu Glu Asn Gly Arg Leu Trp
450                 455                 460 gtc cct cca tcc cca tcg cat cgg aag aca tgg gaa gag caa gca cat   1440
Val Pro Pro Ser Pro Ser His Arg Lys Thr Trp Glu Glu Gln Ala His
465                 470                 475                 480 att gag cga ata cta cac gac cat ttc ctc ttc agg aag ctc act gac   1488
Ile Glu Arg Ile Leu His Asp His Phe Leu Phe Arg Lys Leu Thr Asp
                485                 490                 495 tca cag tgc cat gtt tta ctt gat tgc atg caa aga gtt gag gtg aaa   1536
Ser Gln Cys His Val Leu Leu Asp Cys Met Gln Arg Val Glu Val Lys
        500                 505                 510
```

| | |
|---|---|
| gct ggg gat ata gtg gtg cag cag ggc ggt gaa ggc gag tgc ttc tat<br>Ala Gly Asp Ile Val Val Gln Gln Gly Gly Glu Gly Glu Cys Phe Tyr<br>              515                    520                    525 | 1584 |
| gta gtt ggg agt ggt gag ttt gaa gtg cta gcc att cag gaa gaa gat<br>Val Val Gly Ser Gly Glu Phe Glu Val Leu Ala Ile Gln Glu Glu Asp<br>530                    535                    540 | 1632 |
| gga aag gaa gtt aca aag gtt cta cat cgg tat act gct gac aaa cta<br>Gly Lys Glu Val Thr Lys Val Leu His Arg Tyr Thr Ala Asp Lys Leu<br>545                  550                    555                    560 | 1680 |
| tct tct ttt ggg gag cta gca cta atg tat aat aaa cca ctt caa gct<br>Ser Ser Phe Gly Glu Leu Ala Leu Met Tyr Asn Lys Pro Leu Gln Ala<br>              565                    570                    575 | 1728 |
| tca gtc cgt gct gtg act act gga act tta tgg gct cta aag cga gag<br>Ser Val Arg Ala Val Thr Thr Gly Thr Leu Trp Ala Leu Lys Arg Glu<br>                  580                    585                    590 | 1776 |
| gat ttt cgg gga att ctg atg tca gag ttt tca aat ata cca tca tta<br>Asp Phe Arg Gly Ile Leu Met Ser Glu Phe Ser Asn Ile Pro Ser Leu<br>              595                    600                    605 | 1824 |
| aag ttg ctc cga tca gtg gag ctg ttt acg aga ttg aca atg ctt caa<br>Lys Leu Leu Arg Ser Val Glu Leu Phe Thr Arg Leu Thr Met Leu Gln<br>          610                    615                    620 | 1872 |
| cta agt caa ctt gct gat tct ctt gtt gaa gta act ttt ggg gat ggt<br>Leu Ser Gln Leu Ala Asp Ser Leu Val Glu Val Thr Phe Gly Asp Gly<br>625                    630                    635                    640 | 1920 |
| caa atg ata gta gac aag aat gat gca tct tcc ttg tat att att<br>Gln Met Ile Val Asp Lys Asn Asp Asp Ala Ser Ser Leu Tyr Ile Ile<br>                      645                    650                    655 | 1968 |
| caa aga ggt cgt gtg aaa ctt aaa ttg gct gca gat cag gta aat tca<br>Gln Arg Gly Arg Val Lys Leu Lys Leu Ala Ala Asp Gln Val Asn Ser<br>                  660                    665                    670 | 2016 |
| gat gcc tgg gat ctt ctt agt tct caa aca aag gtg gcc caa tca agt<br>Asp Ala Trp Asp Leu Leu Ser Ser Gln Thr Lys Val Ala Gln Ser Ser<br>              675                    680                    685 | 2064 |
| cga gaa gat ggt aat tac gtg ttt gag ata gat gaa ggg gga cac ttt<br>Arg Glu Asp Gly Asn Tyr Val Phe Glu Ile Asp Glu Gly Gly His Phe<br>          690                    695                    700 | 2112 |
| gga gag tgg gct ctc ttt ggg gag aca att gct ttt act gct atg tca<br>Gly Glu Trp Ala Leu Phe Gly Glu Thr Ile Ala Phe Thr Ala Met Ser<br>705                    710                    715                    720 | 2160 |
| gtt ggt gat gtg act tgt tct act att gca aag gag aag ttt gac tca<br>Val Gly Asp Val Thr Cys Ser Thr Ile Ala Lys Glu Lys Phe Asp Ser<br>                      725                    730                    735 | 2208 |
| att att ggg ccc ttg cca aaa gtt tcc cag tct gat tcc aag ctc aaa<br>Ile Ile Gly Pro Leu Pro Lys Val Ser Gln Ser Asp Ser Lys Leu Lys<br>              740                    745                    750 | 2256 |
| gat tcc ttg gtt cct aaa ggg cat ggt gca gat gat agt tcc ttc agg<br>Asp Ser Leu Val Pro Lys Gly His Gly Ala Asp Asp Ser Ser Phe Arg<br>          755                    760                    765 | 2304 |
| aag gcg cag cta tct gat ttg gaa tgg aaa atg tgc ata tat gcc gct<br>Lys Ala Gln Leu Ser Asp Leu Glu Trp Lys Met Cys Ile Tyr Ala Ala<br>770                    775                    780 | 2352 |
| gat tgc agt gag att ggt ctt gtc caa cta aga ggt tct gac aag atc<br>Asp Cys Ser Glu Ile Gly Leu Val Gln Leu Arg Gly Ser Asp Lys Ile<br>785                    790                    795                    800 | 2400 |
| aaa agc tta aag agg ttt tac atc aag aga gta aaa gac ctt cat aag<br>Lys Ser Leu Lys Arg Phe Tyr Ile Lys Arg Val Lys Asp Leu His Lys<br>                      805                    810                    815 | 2448 |
| gaa aaa cac gta ttt gat gag aag gat ctc atg aaa tct ttg agc caa<br>Glu Lys His Val Phe Asp Glu Lys Asp Leu Met Lys Ser Leu Ser Gln<br>              820                    825                    830 | 2496 |

```
tca act tgt gtg cca gaa gtt cta tgt act tgc gct gat caa tcc tac      2544
Ser Thr Cys Val Pro Glu Val Leu Cys Thr Cys Ala Asp Gln Ser Tyr
        835                 840                 845 cta gga ata ctg ctg aat tgt tgc ctt tgt tgc tca ctg gct tca ata      2592
Leu Gly Ile Leu Leu Asn Cys Cys Leu Cys Cys Ser Leu Ala Ser Ile
850                 855                 860 ctt cat gca cca cta aat gag tcg tct gca cga ttc tat gca gcc tct      2640
Leu His Ala Pro Leu Asn Glu Ser Ser Ala Arg Phe Tyr Ala Ala Ser
865                 870                 875                 880 gtc gtc gta gcg cta gaa aat ctc cat cag agg tcc att ctt tac aga      2688
Val Val Val Ala Leu Glu Asn Leu His Gln Arg Ser Ile Leu Tyr Arg
                885                 890                 895 ggt gtt tct gca gac att ctt atg gtc gac cga tca ggg cat ctt caa      2736
Gly Val Ser Ala Asp Ile Leu Met Val Asp Arg Ser Gly His Leu Gln
        900                 905                 910 cta gtt gac ttc agg ttt gca aag aag ttg caa ggt gaa agg act tac      2784
Leu Val Asp Phe Arg Phe Ala Lys Lys Leu Gln Gly Glu Arg Thr Tyr
        915                 920                 925 aca ata tgt ggg att gcc gac tct cta gct cca gag ata gtt ctt ggt      2832
Thr Ile Cys Gly Ile Ala Asp Ser Leu Ala Pro Glu Ile Val Leu Gly
930                 935                 940 agg ggc cat gga ttt tct gct gac tgg tgg gcg ctg gga gtg ttg att      2880
Arg Gly His Gly Phe Ser Ala Asp Trp Trp Ala Leu Gly Val Leu Ile
945                 950                 955                 960 tat ttc atg ctg caa tca gac atg cca ttt ggc tct tgg agg gag agt      2928
Tyr Phe Met Leu Gln Ser Asp Met Pro Phe Gly Ser Trp Arg Glu Ser
                965                 970                 975 gaa ctg gaa cct ttt gca aag att gcc aag ggt cac ctt gtc atg cca      2976
Glu Leu Glu Pro Phe Ala Lys Ile Ala Lys Gly His Leu Val Met Pro
        980                 985                 990 tca aca ttc agc atc gaa gtt gtt  gac ctt att aca aag  cta ctc gag    3024
Ser Thr Phe Ser Ile Glu Val Val  Asp Leu Ile Thr Lys  Leu Leu Glu
        995                 1000                1005 gta aac  gaa aat gcg cgc ctt  ggg gcc aag gga gcg  gaa tct gtg       3069
Val Asn  Glu Asn Ala Arg Leu  Gly Ala Lys Gly Ala  Glu Ser Val
    1010                1015                1020 aaa aga  cac ccc tgg ttt gat  ggc att gac tgg aaa  caa ata gca       3114
Lys Arg  His Pro Trp Phe Asp  Gly Ile Asp Trp Lys  Gln Ile Ala
    1025                1030                1035 gat ggt  act tat aca gta ccc  caa gaa atc acc gat  cgt gtc gac       3159
Asp Gly  Thr Tyr Thr Val Pro  Gln Glu Ile Thr Asp  Arg Val Asp
    1040                1045                1050 agc tat  gta gaa act ctt aca  gag gac ttg aca gca  tcc cct tcc       3204
Ser Tyr  Val Glu Thr Leu Thr  Glu Asp Leu Thr Ala  Ser Pro Ser
    1055                1060                1065 atg cca  agt gaa gaa aca gct  gat cag gct gct cca  gaa tgg atc       3249
Met Pro  Ser Glu Glu Thr Ala  Asp Gln Ala Ala Pro  Glu Trp Ile
    1070                1075                1080 cag gat tgg tga                                                      3261
Gln Asp Trp
    1085

<210> SEQ ID NO 41
<211> LENGTH: 1086
<212> TYPE: PRT
<213> ORGANISM: Oryza sativa

<400> SEQUENCE: 41

Met Gly Cys Ser Pro Ser Lys Val Cys Ser Cys Pro His Tyr Lys Gly
1               5                   10                  15
```

```
Ser Leu Cys Phe Cys Asp Cys Gly Cys Phe Gly Gln Thr Pro Asp Ser
            20                  25                  30

Pro Arg Glu Ser Arg Gly Lys Ser Asn Arg Val Arg Gly Lys Thr Asp
            35                  40                  45

Ser Ser Ala Ser Asp Ala Ser Ser Asp Leu Glu Glu Asp Asp Asp
 50                      55                  60

Gly Leu His Gln Met Asn Ile Thr Arg Asp Ser Asn Val Gly Ile Asn
 65                  70                  75                  80

Arg Leu Ser Arg Val Ser Ser Gln Phe Leu Pro Pro Glu Gly Ser Arg
                85                  90                  95

Lys Val Arg Ile Pro Leu Gly Asn Tyr Asp Leu Arg Tyr Ser Tyr Leu
            100                 105                 110

Ser Gln Arg Gly Tyr Tyr Pro Glu Ser Leu Asp Lys Pro Asn Gln Asp
            115                 120                 125

Ser Phe Cys Ile His Thr Pro Phe Gly Thr Ser Pro Asp Asp His Phe
            130                 135                 140

Phe Gly Val Phe Asp Gly His Gly Glu Tyr Gly Ala Gln Cys Ser Gln
145                 150                 155                 160

Phe Val Lys Arg Arg Leu Cys Glu Asn Leu Leu Arg Asp Asp Arg Phe
                165                 170                 175

Arg Thr Asp Val Val Gln Ala Leu His Ser Ala Phe Leu Ala Thr Asn
            180                 185                 190

Ser Gln Leu His Ala Asp Ser Leu Asp Asp Ser Met Ser Gly Thr Thr
            195                 200                 205

Ala Val Thr Val Leu Val Arg Gly Lys Thr Ile Tyr Ile Ala Asn Thr
210                 215                 220

Gly Asp Ser Arg Ala Val Ile Ala Glu Lys Arg Gly Glu Asp Val Val
225                 230                 235                 240

Ala Val Asp Leu Ser Ile Asp Gln Thr Pro Tyr Arg Thr Asp Glu Leu
            245                 250                 255

Glu Arg Val Lys Glu Cys Gly Ala Arg Val Met Thr Leu Asp Gln Ile
            260                 265                 270

Glu Gly Leu Lys Asn Pro Asp Val Gln Cys Trp Gly Thr Glu Glu Ser
            275                 280                 285

Asp Asp Gly Asp Pro Pro Arg Leu Trp Val Gln Asn Gly Met Tyr Pro
290                 295                 300

Gly Thr Ala Phe Thr Arg Ser Ile Gly Asp Ser Val Ala Glu Ser Ile
305                 310                 315                 320

Gly Val Val Ala Asn Pro Glu Ile Phe Ile Leu Glu Leu Asn Ala Asn
            325                 330                 335

His Pro Phe Phe Val Leu Ala Ser Asp Gly Val Phe Glu Phe Leu Ser
            340                 345                 350

Ser Gln Thr Val Val Asp Met Ile Ala Lys Tyr Lys Asp Pro Arg Asp
            355                 360                 365

Ala Cys Ala Ala Ile Val Ala Glu Ser Tyr Arg Leu Trp Leu Gln Tyr
            370                 375                 380

Glu Thr Arg Thr Asp Asp Ile Thr Ile Val Val His Ile Asn Gly
385                 390                 395                 400

Leu Thr Asp Met Glu Cys Thr Gln Thr Val Met Lys Val Ser Leu Gln
                405                 410                 415

Pro Ser Gln Gln Val Val Glu Leu Val Gly Ser Glu Pro Ser Thr
            420                 425                 430

Ile Ser Leu Asn Pro Lys Asn Gln Arg Ser Arg Gln Asp Leu Ser Arg
            435                 440                 445
```

```
Ala Arg Leu Arg Ala Leu Glu Ser Ser Leu Glu Asn Gly Arg Leu Trp
    450                 455                 460

Val Pro Ser Pro Ser His Arg Lys Thr Trp Glu Glu Gln Ala His
465                 470                 475                 480

Ile Glu Arg Ile Leu His Asp His Phe Leu Phe Arg Lys Leu Thr Asp
                    485                 490                 495

Ser Gln Cys His Val Leu Leu Asp Cys Met Gln Arg Val Glu Val Lys
                500                 505                 510

Ala Gly Asp Ile Val Val Gln Gln Gly Gly Glu Gly Glu Cys Phe Tyr
                515                 520                 525

Val Val Gly Ser Gly Glu Phe Glu Val Leu Ala Ile Gln Glu Glu Asp
    530                 535                 540

Gly Lys Glu Val Thr Lys Val Leu His Arg Tyr Thr Ala Asp Lys Leu
545                 550                 555                 560

Ser Ser Phe Gly Glu Leu Ala Leu Met Tyr Asn Lys Pro Leu Gln Ala
                565                 570                 575

Ser Val Arg Ala Val Thr Thr Gly Thr Leu Trp Ala Leu Lys Arg Glu
                580                 585                 590

Asp Phe Arg Gly Ile Leu Met Ser Glu Phe Ser Asn Ile Pro Ser Leu
                595                 600                 605

Lys Leu Leu Arg Ser Val Glu Leu Phe Thr Arg Leu Thr Met Leu Gln
610                 615                 620

Leu Ser Gln Leu Ala Asp Ser Leu Val Glu Val Thr Phe Gly Asp Gly
625                 630                 635                 640

Gln Met Ile Val Asp Lys Asn Asp Asp Ala Ser Ser Leu Tyr Ile Ile
                645                 650                 655

Gln Arg Gly Arg Val Lys Leu Lys Leu Ala Ala Asp Gln Val Asn Ser
                660                 665                 670

Asp Ala Trp Asp Leu Leu Ser Ser Gln Thr Lys Val Ala Gln Ser Ser
                675                 680                 685

Arg Glu Asp Gly Asn Tyr Val Phe Glu Ile Asp Glu Gly Gly His Phe
                690                 695                 700

Gly Glu Trp Ala Leu Phe Gly Glu Thr Ile Ala Phe Thr Ala Met Ser
705                 710                 715                 720

Val Gly Asp Val Thr Cys Ser Thr Ile Ala Lys Glu Lys Phe Asp Ser
                725                 730                 735

Ile Ile Gly Pro Leu Pro Lys Val Ser Gln Ser Asp Ser Lys Leu Lys
                740                 745                 750

Asp Ser Leu Val Pro Lys Gly His Gly Ala Asp Asp Ser Ser Phe Arg
                755                 760                 765

Lys Ala Gln Leu Ser Asp Leu Glu Trp Lys Met Cys Ile Tyr Ala Ala
    770                 775                 780

Asp Cys Ser Glu Ile Gly Leu Val Gln Leu Arg Gly Ser Asp Lys Ile
785                 790                 795                 800

Lys Ser Leu Lys Arg Phe Tyr Ile Lys Arg Val Lys Asp Leu His Lys
                805                 810                 815

Glu Lys His Val Phe Asp Glu Lys Asp Leu Met Lys Ser Leu Ser Gln
                820                 825                 830

Ser Thr Cys Val Pro Glu Val Leu Cys Thr Cys Ala Asp Gln Ser Tyr
                835                 840                 845

Leu Gly Ile Leu Leu Asn Cys Cys Leu Cys Cys Ser Leu Ala Ser Ile
    850                 855                 860

Leu His Ala Pro Leu Asn Glu Ser Ser Ala Arg Phe Tyr Ala Ala Ser
```

```
                865                 870                 875                 880
Val Val Val Ala Leu Glu Asn Leu His Gln Arg Ser Ile Leu Tyr Arg
                    885                 890                 895
Gly Val Ser Ala Asp Ile Leu Met Val Asp Arg Ser Gly His Leu Gln
                900                 905                 910
Leu Val Asp Phe Arg Phe Ala Lys Lys Leu Gln Gly Glu Arg Thr Tyr
            915                 920                 925
Thr Ile Cys Gly Ile Ala Asp Ser Leu Ala Pro Glu Ile Val Leu Gly
        930                 935                 940
Arg Gly His Gly Phe Ser Ala Asp Trp Trp Ala Leu Gly Val Leu Ile
945                 950                 955                 960
Tyr Phe Met Leu Gln Ser Asp Met Pro Phe Gly Ser Trp Arg Glu Ser
                965                 970                 975
Glu Leu Glu Pro Phe Ala Lys Ile Ala Lys Gly His Leu Val Met Pro
                980                 985                 990
Ser Thr Phe Ser Ile Glu Val Val  Asp Leu Ile Thr Lys  Leu Leu Glu
                995                 1000                1005
Val Asn  Glu Asn Ala Arg Leu  Gly Ala Lys Gly Ala  Glu Ser Val
    1010                1015                1020
Lys Arg  His Pro Trp Phe Asp  Gly Ile Asp Trp Lys  Gln Ile Ala
    1025                1030                1035
Asp Gly  Thr Tyr Thr Val Pro  Gln Glu Ile Thr Asp  Arg Val Asp
    1040                1045                1050
Ser Tyr  Val Glu Thr Leu Thr  Glu Asp Leu Thr Ala  Ser Pro Ser
    1055                1060                1065
Met Pro  Ser Glu Glu Thr Ala  Asp Gln Ala Ala Pro  Glu Trp Ile
    1070                1075                1080
Gln Asp  Trp
    1085

<210> SEQ ID NO 42
<211> LENGTH: 1176
<212> TYPE: DNA
<213> ORGANISM: Arabidopsis thaliana

<400> SEQUENCE: 42
atggcgtctg ctagcttcgt taagcctaac accctctctt ctccatggat cggccaacgc      60
tcctttgctc acacctctgc ttcttcttct cctcctcctc gagtctcctt cgcgatccgc     120
gccggtgctt actccgacga gcttgttaaa accgccaaaa gcattgcatc ccctgggaga     180
ggtatcttgg cgatcgatga gtccaatgca acctgtggga gaggcttgc ttctatcggc      240 ttggataaca ccgaggacaa ccgtcaggcc tacaggcaac ttctgcttac cactcctggc     300
ctcggcgatt acatctctgg ttccattctc ttcgaggaga ctctttacca gtccaccaag     360
gacggtaaga cctttgtcga ttgcttgcgc gatgccaaca tcgtccctgg catcaaagtt     420
gacaagggct tgtctcccct agccggttcc aacgaagagt cttggtgcca aggcttggat     480
ggattggcct cacgctctgc tgagtactac aagcaaggcg ctcgtttttgc caagtggagg     540 acagtggtga gtgttccctg cggtccttca gcactggctg tgaaggaagc tgcgtggggg     600
ctggctcgct atgcagccat ctctcaggat aatggtcttg tccccattgt ggagccagag     660
atccttctgg acgggaccca cccaatagag aggactctgg aggtggcaga gaaagtgtgg     720
tcagaggtgt tcttctactt ggcacagaac aacgtcatgt ttgagggcat tctgttgaag     780
ccgagcatgg tcaccccagg cgctgagcac aagaacaagg cctctcccga gaccgttgca     840
```

```
gatttcacgc tcaccatgct gaaaaggagg gttcctccgg ctgtcccagg gatcatgttt    900
ctgtcaggag gacaatcaga ggcagaggcc acactgaacc tgaacgccat gaaccagagc    960
ccaaacccat ggcatgtgtc cttctcatac gcacgtgccc tgcagaactc cgtgctcaga   1020
acatggcaag gcaagccgga gaagattgag gcctcgcaga aggcactgtt ggtgagggca   1080
aaggccaact cactggccca gctcggcaaa tactcagccg agggagagaa cgaggatgcc   1140
aagaaaggaa tgtttgtcaa gggttacacc tactga                            1176

<210> SEQ ID NO 43
<211> LENGTH: 21
<212> TYPE: DNA
<213> ORGANISM: Artificial
<220> FEATURE:
<223> OTHER INFORMATION: Synthetic DNA

<400> SEQUENCE: 43
ggatcctatg gcgtctgcta g                                              21

<210> SEQ ID NO 44
<211> LENGTH: 21
<212> TYPE: DNA
<213> ORGANISM: Artificial
<220> FEATURE:
<223> OTHER INFORMATION: Synthetic DNA

<400> SEQUENCE: 44
atctgcaacg gtctcgggag a                                              21

<210> SEQ ID NO 45
<211> LENGTH: 22
<212> TYPE: DNA
<213> ORGANISM: Artificial
<220> FEATURE:
<223> OTHER INFORMATION: Synthetic DNA

<400> SEQUENCE: 45
gtgtggtccg aggtgttctt ct                                             22

<210> SEQ ID NO 46
<211> LENGTH: 24
<212> TYPE: DNA
<213> ORGANISM: Artificial
<220> FEATURE:
<223> OTHER INFORMATION: Synthetic DNA

<400> SEQUENCE: 46
gagctcgagt aggtgtaacc cttg                                           24
```